United States Patent
Qi et al.

(10) Patent No.: US 11,426,090 B2
(45) Date of Patent: Aug. 30, 2022

(54) DEVICE AND METHOD FOR MEASURING A VITAL SIGNAL

(71) Applicant: Xin Qi, Shenzhen (CN)

(72) Inventors: Xin Qi, Shenzhen (CN); Ting Liu, Shenzhen (CN)

(73) Assignee: Xin Qi, Shenzhen (CN)

( * ) Notice: Subject to any disclaimer, the term of this patent is extended or adjusted under 35 U.S.C. 154(b) by 348 days.

(21) Appl. No.: 15/764,363

(22) PCT Filed: Sep. 27, 2016

(86) PCT No.: PCT/CN2016/100425
§ 371 (c)(1),
(2) Date: Mar. 29, 2018

(87) PCT Pub. No.: WO2017/054715
PCT Pub. Date: Apr. 6, 2017

(65) Prior Publication Data
US 2018/0279892 A1    Oct. 4, 2018

(30) Foreign Application Priority Data

Sep. 30, 2015 (CN) .................. 201510651334.X

(51) Int. Cl.
*A61B 5/024* (2006.01)
*A61B 5/1455* (2006.01)
(Continued)

(52) U.S. Cl.
CPC ........ *A61B 5/02427* (2013.01); *A61B 5/1455* (2013.01); *A61B 5/14552* (2013.01);
(Continued)

(58) Field of Classification Search
CPC ............ A61B 5/02427; A61B 5/14552; A61B 5/14558; A61B 5/7214; A61B 5/1455;
(Continued)

(56) References Cited

U.S. PATENT DOCUMENTS

| 6,999,685 B1 | 2/2006 | Kawase |
| 7,376,453 B1 | 5/2008 | Diab et al. |

(Continued)

FOREIGN PATENT DOCUMENTS

| CN | 103027690 A | 4/2013 |
| CN | 104000600 A | 8/2014 |

(Continued)

OTHER PUBLICATIONS

Shimazaki et al. 2014 Conf. Proc. IEEE Eng. Med. Biol. Soc. 2014 pp. 3216-3219 (Year: 2014).*

(Continued)

*Primary Examiner* — Keith M Raymond
*Assistant Examiner* — Patrick M Mehl
(74) *Attorney, Agent, or Firm* — Metis IP LLC

(57) ABSTRACT

The present disclosure provides a vital sign measuring device and method that may measure a heart rate signal of a living body in a motion state. The method comprises detecting two different signals, using an adaptive noise removal algorithm for removing noise from the two signals, and obtaining a more accurate heat rate signal after a certain operation.

17 Claims, 37 Drawing Sheets

(51) Int. Cl.
*A61B 5/00* (2006.01)
*A61B 5/0295* (2006.01)

(52) U.S. Cl.
CPC ........ *A61B 5/14558* (2013.01); *A61B 5/7207* (2013.01); *A61B 5/7214* (2013.01); *A61B 5/0295* (2013.01); *A61B 5/7228* (2013.01)

(58) Field of Classification Search
CPC ... A61B 5/7207; A61B 5/0295; A61B 5/7228; A61B 5/0059; A61B 5/02416; A61B 5/11; A61B 5/7275; A61B 5/0075; A61B 5/0013; A61B 5/14546; A61B 5/145; A61B 5/7203; A61B 5/024; A61B 2562/0242; A61B 2562/0233; G02B 27/283; G01N 21/47; G01N 21/21; G01N 2021/4792
See application file for complete search history.

(56) References Cited

U.S. PATENT DOCUMENTS

| | | | |
|---|---|---|---|
| 7,937,130 B2* | 5/2011 | Diab | A61B 5/14551 600/336 |
| 8,923,941 B2 | 12/2014 | LeBoeuf et al. | |
| 2006/0092418 A1 | 5/2006 | Xu et al. | |
| 2007/0055119 A1 | 3/2007 | Lash et al. | |
| 2008/0298649 A1* | 12/2008 | Ennis | G06K 9/0012 382/125 |
| 2009/0306487 A1 | 12/2009 | Crowe et al. | |
| 2011/0054336 A1 | 3/2011 | Jornod | |
| 2012/0095307 A1 | 4/2012 | Caduff et al. | |
| 2012/0150052 A1 | 6/2012 | Buchheim et al. | |
| 2014/0058217 A1 | 2/2014 | Giovangrandi | |
| 2014/0081153 A1 | 3/2014 | Kuno | |
| 2014/0121471 A1 | 5/2014 | Walker | |
| 2014/0243622 A1 | 8/2014 | Crowe et al. | |
| 2014/0275852 A1* | 9/2014 | Hong et al. | A61B 5/02427 600/301 |
| 2015/0057511 A1* | 2/2015 | Basu | A61B 5/02433 600/323 |
| 2015/0065889 A1 | 3/2015 | Gandelman et al. | |
| 2015/0148623 A1* | 5/2015 | Benaron | A61B 5/4875 600/306 |
| 2015/0190062 A1 | 7/2015 | Han et al. | |
| 2015/0196256 A1 | 7/2015 | Venkatraman et al. | |
| 2015/0201854 A1 | 7/2015 | Hong et al. | |
| 2015/0208933 A1* | 7/2015 | Satomi | A61B 5/02416 600/479 |
| 2015/0374276 A1* | 12/2015 | Farkas | A61B 5/14558 600/407 |
| 2016/0081567 A1* | 3/2016 | Nousiainen | A61B 5/726 600/473 |
| 2016/0242647 A1 | 8/2016 | Ishii et al. | |
| 2016/0249812 A1* | 9/2016 | Wang | G01N 29/0681 600/407 |
| 2016/0270676 A1 | 9/2016 | Yamashita | |
| 2017/0108433 A1 | 4/2017 | Helfmann et al. | |

FOREIGN PATENT DOCUMENTS

| | | | |
|---|---|---|---|
| CN | 104224149 A | 12/2014 | |
| CN | 104392103 A | 3/2015 | |
| CN | 104586370 A | 5/2015 | |
| CN | 104739386 A | 7/2015 | |
| JP | 2003210465 A * | 7/2003 | A61B 10/00 |
| JP | 2003210465 A | 7/2003 | |
| JP | 2008212258 A | 9/2008 | |
| JP | 2009291389 A | 12/2009 | |
| JP | 2011104124 A | 6/2011 | |
| JP | 2012187358 A | 10/2012 | |
| TW | 201206397 A | 2/2012 | |
| WO | 2014184447 A1 | 11/2014 | |
| WO | 2015084376 A1 | 6/2015 | |
| WO | 2015102589 A1 | 7/2015 | |
| WO | 2015105320 A1 | 7/2015 | |
| WO | 2015117829 A1 | 8/2015 | |
| WO | WO2015117829 A1 * | 8/2015 | A61B 5/024 |

OTHER PUBLICATIONS

The Notice of Rejection in Japanese Application No. 2018517208 dated Feb. 18, 2020, 12 pages.
International Search Report in PCT/CN2016/100425 dated Jan. 5, 2017, 10 pages.
The extended European search report in European Application No. 16850339.9 dated Aug. 9, 2018, 9 pages.
Su Yixiong, Research on Non-contact Picking Method of Backscattered Light in Biological Tissue, 2003.
Takunori Shimazaki et al., Design of PPG-Based Heart Rate Sensor Enabling Motion Artifact Cancellation, SASIMI 2015 Proceedings, 283-286.
Takunori Shimazaki et al., Cancellation of Motion Artifact Induced by Exercise for PPG-Based Heart Rate Sensing, 36th Annual International Conference of the IEEE Engineering in Medicine and Biology Society, 3216-3219, 2014.
Wan Wenjun, Designing and Evaluating Physical Activity by Heart Rate Monitoring, Journal of GZIPE, 23(3): 35-37, 2003.
Lv Yufeng et al., Theoretical Discussion on the Evaluation of Exercise Load intensity, Journal of Beijing Teachers College of Physical Education, 9(4): 35-38, 1997.
Zhang Yong, Research on Fat Oxidation Kinetics and Maximal Fat Oxidation in Exercise, 2013.
Zhu Haizhu, The Study on the Energy Consumption and Characterization of Substrate Metabolism of Organisms During Activity, 2009.
Shi Ping et al., Principles of Photoplethysmography and Its Applications in Physiological Measurements, Journal of Biomedical Engineering, 30(4): 899-904, 2013.
Zhang Kun et al., Motion Artifact Cancellation in Photoplethysmography Using Reconstruction of Wavelet Transform Modulus maxima, Chinese Journal of Scientific Instrument, 30(3): 586-589, 2009.
Wang Qian et al., Artifact Reduction based on Empirical Mode Decomposition (EMD) in Photoplethysmography for Pulse Rate Detection, 32nd Annual International Conference of the IEEE EMBS, 959-962, 2010.
K. Ashoka Reddy et al., Motion Artifact Reduction and Data Compression of Photoplethysmo-graphic Signals Utilizing Cycle by Cycle Fourier Series Analysis, I2MTC 2008—IEEE International Instrumentation and Measurement Technology Conference, 2008.
Yadhuraj S.R et al., Motion Artifact Reduction in Photoplethysmographic Signals: A Review, International Journal of Innovative Reserch & Development, 2(3): 626-640, 2013.
M. Raghu Ram et al., A Novel Approach for Motion Artifact Reduction in PPG Signals Based on AS-LMS Adaptive Filter, IEEE Transactions on Instrumentation and Measurement, 61(5): 1445-1457, 2012.
Jianchu Yao et al., A Short Study to Assess the Potential of Independent Component Analysis for Motion Artifact Separation in Wearable Pulse Oximeter Signals, Proceedings of the 2005 IEEE Engineering in Medicine and Biology 27th Annual Conference, 3585-3588, 2005.
Zhang Hong et al., The Study on the Adaptive Filtering Method for Eliminating the Motion Artifact in Pulse Oximetry Measurement, 5(1): 6-11, 2001.
Fan Jinghui, Study on Non-invasive Pulse Monitoring System of Oxygen Saturation of Blood, 2005.
Huang Lan, Study and Application of Absolute Detection Methods on Tissue Oxygenation by Using Near Infrared Spectroscopy, 2004.
Gong Wei et al., Optical Model and Optical Properties of Human Skin, Chinese Journal of Laser Medicine & Surgery, 19(2): 114-117, 2010.
Chen Rong et al., The Optical Model of Human Skin, Acta Laser Biology Sinica, 14(6): 401-404, 2005.
J. M. Schmitt et al., Multilayer Model of Photon Diffusion in Skin, Optical Society of America, 7(11): 2141-2153, 1990.

(56) References Cited

OTHER PUBLICATIONS

Ding Haishu et al., Simulation and Application for Near Infra-Red Light Transport in Biological Tissues, J. Tsinghua Univ. ( Sci. & Tech.), 39(9): 5-8, 1999.
Communication Pursuant to Article 94(3) EPC in European Application No. 16850339.9 dated Mar. 15, 2021, 8 pages.
Notice of Reasons for Refusal in Japanese Application No. 2020184328 dated Nov. 2, 2021, 8 pages.

* cited by examiner

DEVICE AND METHOD FOR MEASURING A VITAL SIGNAL

CROSS-REFERENCES

The present application is a U.S. national stage of International Application No. PCT/CN2016/100425, filed on Sep. 27, 2017, which claims priority to Chinese Application No. 201510651334.X filed on Sep. 30, 2015. Each of the above applications are incorporated herein by reference in their entireties.

TECHNICAL FIELD

The present disclosure relates to systems and methods of measuring a vital signal of a living body, and more particularly, to systems and methods of measuring heart rate signals of a living body in a motion state.

BACKGROUND ART

Heart rate is a very important physiological indicator among vital sign parameters. Heart rate measurement may provide a reference for medical diagnosis in the medical field. Since the heart rate is also an evaluation criterion of loads on a body during a human motion, the detection of the heart rate in a physical exercise may guide an athlete to exercise reasonably. The energy expenditure during motion may be indirectly derived from the monitor of heart rate, which may help the athlete to lose weight and shape the body more effectively. In addition, the heart rate measurement does not require complex instruments and devices, and the heart rate is suitable for continuous monitoring. Therefore, the real-time monitoring of heart rate data has broad and important values.

SUMMARY OF THE INVENTION

The present disclosure provides a device and method for acquiring vital signs. The device may comprise: a first signal source configured to emit a first light beam to a surface of a living body, wherein the first light beam may be monochromatic light, or may be light within a wavelength range, and the monochromatic light or the light within the wavelength range includes, but is not limited to, a red light, a yellow light, a green light, a blue light, a violet light, an infrared light, an ultraviolet light, etc.; a first signal detecting device configured to detect a first signal reflected by the living body, wherein the first signal detecting device may be a photoelectric sensor, the first signal being associated with the first light beam; a second signal detecting device configured to detect a second signal reflected by the living body, wherein the second signal detecting device may be a photoelectric sensor, the second signal being associated with the first light beam but different from the first signal; and a processor configured to determine a vital signal of the living body based on the first signal and the second signal. Optionally, ratios of vital sign information to noise information of the first signal and the second signal are different. The first signal source, the first signal detecting device and the second signal detecting device may be located on a straight line, or may also be at different distances above the surface of the living body.

Optionally, the surface of the living body may be particular tissue or site of the living body such as, but not limited to, skin.

Optionally, the first light beam may be incident to a skin surface and may be directly reflected by an interface formed by the stratum corneum of the skin and an external surface to emit reflected light, the reflected light may include motion information, and may sequentially enter epidermis and dermis of skin tissue after being refracted by the skin surface and may be scattered and absorbed by the skin tissue to emit scattered light, the scattered light may include motion information and vital signs. The first signal and/or the second signal reflected by the living body may include reflected light of the skin surface and scattered light scattered by the skin tissue.

Optionally, the first signal may include a photoplethysmograph (PPG) signal; and optionally, the second signal may include noise information generated by the motion of the living body.

Optionally, a distance between the first signal source and the first signal detecting device may be greater than a distance between the first signal source and the second signal detecting device; a distance between the first signal detecting device and the surface of the living body may be less than a distance between the second signal detecting device and the surface of the living body; and the difference of the distances may make photons penetrate into the skin tissue with different average depths and may make the ratios of the vital sign information to the noise information carried by the first signal and the second signal different.

Optionally, the device may include a second signal source for emitting a second light beam to the surface of the living body, the first signal source and the second signal source may emit beams simultaneously or emit beams alternately, and wavelengths of the beam of the first signal source and the beam of the second signal source may be the same or different. The first signal source and the first signal detecting device may constitute first sensor, and the second signal source and the second signal detecting device may constitute a second sensor.

Optionally, a distance between the second signal source and the second signal detecting device may be less than a distance between the first signal source and the first signal detecting device; and the difference of the distances may make the first light beam and the second light beam penetrate into the skin tissue with different average depths and may make ratios of the vital sign components carried by the first signal and the second signal different.

Optionally, the device may include an optical component which may be located between the second signal detecting device and the living body for changing a transmission direction of the second signal, or may be located between the first signal detecting device and the living body for changing a transmission direction of the first signal; optionally, the device may include at least two optical components which may be located between the second signal detecting device and the living body and between the first signal detecting device and the living body respectively. The two or more optical components may be the same or different. Further optionally, the component may be a lens or a light guide, which may be used to change a direction of the signal detected by the second signal detecting device or the first signal detecting device such that the light is at an angle with respect to the skin, and lens types include but are not limited to a concave lens, a convex lens, a plano-convex lens, a plano-concave lens, and a meniscus lens.

Optionally, the first light beam is polarized light, wherein the polarized light may be directly generated by the first signal source or may be generated by a combination of the first signal source and a specific optical component.

Optionally, the device may include a polarized device, which may include a first polarized device located between the second signal detecting device and the living body, may also include a second polarized device located between the first signal detecting device and the living body, and may also include a third polarized device located between the first signal source and the living body; further optionally, the polarized device may be a polarizer for generating linearly polarized light, wherein polarization directions of the polarizer may be the same or different, and optionally, different polarization directions may be perpendicular to each other. If incident light is linearly polarized light satisfying a certain condition, the reflected light of the skin surface may still be linearly polarized light, and backscattered light may be non-polarized light; by adjusting the polarization direction of the polarizer, the first signal and/or the second signal may include the reflected light and the backscattered light with different ratios, and ratios of the vital sign components carried by the first signal and the second signal are different.

Optionally, the device may include one or more beam splitters for splitting the reflected signal of the living body into two parts which may be the reflected light of the beam splitter and the transmitted light of the beam splitter, respectively; reflected and transmitted components by the beam splitter may be equal, and the beam splitter may take the first signal and the second signal from the same region on the skin, to improve the correlation; further preferably, the beam splitter may be a polarized beam splitter for splitting light into polarized light in different polarization directions, and the polarized beam splitter having a polarizer may reduce the number of polarizers used in the sensor.

Optionally, the first signal detecting device may locate in vicinity of a normal line of the first light beam, and the intensity of the backscattered light detected by the first signal detecting device is greater. Further preferably, the first signal detecting device may be located in the normal direction of the first light beam, and the intensity of the backscattered light detected by the first signal detecting device is greatest.

Optionally, the device may include a processing module, the processing module may acquire vital sign information such as, but not limited to, heart rate information, according to the first signal and the second signal, and the processing module may include but not limited to, functions, such as noise removal, signal analysis and signal characterization.

The present disclosure also provides another device for acquiring vital signs. The device may comprise: a first signal source configured to emit a first light beam to a surface of a living body; a second signal source configured to emit a second light beam to the surface of the living body, wherein the first signal source and the second signal source may emit beams alternately or emit beams simultaneously, and wavelengths of the first light beam and the second light beam may be the same or different; and a first signal detecting device configured to detect a first signal and a second signal reflected by the living body at different time points, wherein the first signal detecting device may be a photoelectric sensor, the first signal may associate with the first light beam, the second signal may associate with the second light beam, and the first signal may be different from the second signal. Optionally, ratios of vital sign information to noise information of the first signal and the second signal are different. The first signal source, the second signal source and the first signal detecting device may be located on a straight line, or may also be at different distances above the surface of the living body.

Optionally, the surface of the living body may be particular tissue or site of the living body such as, but not limited to, skin.

Optionally, the first light beam and the second light beam may be incident to a skin surface and may be directly reflected by an interface formed by the stratum corneum of the skin and an external surface to emit reflected light which may include motion information. The first light beam and the second light beam may sequentially enter epidermis and dermis of skin tissue after being refracted by the skin surface and may be scattered and absorbed by the skin tissue to emit scattered light which may include motion information and vital signs. The first signal and/or the second signal reflected by the living body may include reflected light of the skin surface and scattered light scattered by the skin tissue.

Optionally, the first signal may include a PPG signal; and further optionally, the second signal may include noise information generated by the motion of the living body.

Optionally, a distance between the first signal source and the first signal detecting device may be greater than a distance between the second signal source and the first signal detecting device; a distance between the first signal source and the surface of the living body may be less than a distance between the second signal source and the surface of the living body; and the difference of the distances may make photons penetrate into the skin tissue with different average depths and may make ratios of the vital sign components carried by the first signal and the second signal different.

Optionally, the device may include an optical component which may be located between the second signal source and the living body for changing a transmission direction of the second signal or may be located between the first signal source and the living body for changing a transmission direction of the first signal; optionally, the device may include at least two optical components which may be located between the second signal source and the living body and between the first signal source and the living body respectively. The two or more optical components may be the same or different. Further optionally, the component may be a lens or a light guide which may be used to change a direction of a beam emitted by the second signal source or the first signal source such that the light is at an angle with respect to the skin, and lens types include but are not limited to a concave lens, a convex lens, a plano-convex lens, a plano-concave lens and a meniscus lens.

Optionally, the first light beam and/or the second light beam may be polarized light which may be directly generated by the first signal source and/or the second signal source, and may be generated by a combination of the first signal source and a specific optical component, and/or a combination of the second signal source and a specific optical component.

Optionally, the device may include a polarized device, which may include a first polarized device located between the first signal detecting device and the living body, may include a second polarized device located between the second signal source and the living body, and may include a third polarized device located between the first signal source and the living body; further optionally, the polarized device may be a polarizer for generating linearly polarized light, wherein polarization directions of the polarizer may be the same or different, and optionally, different polarization directions may be perpendicular to each other. When incident light is linearly polarized light satisfying a certain condition, the reflected light of the skin surface may still be linearly polarized light, and backscattered light may be non-polarized light; by adjusting the polarization direction of the polarizer, the first signal and or the second signal include the reflected light and the backscattered light with different ratios, and ratios of the vital sign components carried by the first signal and the second signal are different.

Optionally, the device may include one or more beam splitters for splitting the reflected signal of the living body into two parts which may be the reflected light of the beam splitter and the transmitted light of the beam splitter, respectively; reflected and transmitted components by the beam splitter may be equal, and the beam splitter may cause the first light beam and the second light beam to emit to the same region of the living body, to improve the correlation; further preferably, the beam splitter may be a polarized beam splitter for splitting light into polarized lights having different polarization directions, and the polarized beam splitter has a polarizer which reduces the number of polarizers used in the sensor.

Optionally, the first signal detecting device may locate in vicinity of a normal line of the first light beam, and the intensity of the backscattered light detected by the first signal detecting device is great. Further preferably, the first signal detecting device is located in a normal direction of the first light beam, and the intensity of the backscattered light detected by the first signal detecting device is greatest.

Optionally, the device may include a processing module which may acquire vital sign information such as, but not limited to, heart rate information according to the first signal and the second signal, and the processing module may include but not limited to functions, such as noise removal, signal analysis and signal characterization.

In the meantime, the present disclosure provides a method for acquiring vital signs. The method may comprise: emitting a first light beam to a surface of a living body; detecting a first signal reflected by the living body, wherein the first signal may be detected by a photoelectric sensor; and detecting a second signal reflected by the living body, wherein the second signal may be detected by a photoelectric sensor. Photodetectors which detect the first signal and the second signal may be the same or may be different. The first signal and the second signal may associate with the first light beam, and the first signal may be different from the second signal. Optionally, ratios of vital sign information to noise information of the first signal and the second signal are different.

Optionally, the surface of the living body may be particular tissue or site of the living body such as, but not limited to, skin.

Optionally, the first light beam may be incident to a skin surface and may be directly reflected by an interface formed by the stratum corneum of the skin and an external surface to emit reflected light which may include motion information, and may sequentially enter epidermis and dermis of skin tissue after being refracted by the skin surface and may be scattered and absorbed by the skin tissue to emit scattered light which may include motion information and vital signs. The first signal and/or the second signal reflected by the living body may include reflected light of the skin surface and scattered light scattered by the skin tissue.

Optionally, the first signal may include a PPG signal; and may also include noise information generated by the motion of the living body.

Optionally, a transmission distance of the second signal within the skin tissue may be greater than a transmission distance of the first signal within the skin tissue; and the difference of the distances may make ratios of the vital sign information to noise information carried by the first signal and the second signal different.

Optionally, the method may use an optical component which may be located between the first signal source and the living body for changing a transmission direction of the first signal or may be located between the second signal source and the living body for changing a transmission direction of the second signal; optionally, the method may use at least two optical components which may be located between the first signal source and the living body and between the second signal source and the living body respectively. The two or more optical components may be the same or different. Further optionally, the component may be a lens or a light guide which may be used to change directions of the first signal and the second signal such that the signal is at an angle with respect to the skin, and lens types include but are not limited to a concave lens, a convex lens, a plano-convex lens, a plano-concave lens and a meniscus lens.

Optionally, the first signal and/or the second signal may be polarized light which may be directly generated by the first signal source and/or the second signal source, and may be generated by a combination of the first signal source and a specific optical component and/or a combination of the second signal source and a specific optical component.

Optionally, the device may include a polarized device, may include a first polarized device, the first polarized device may polarize the first signal, and may include a second polarized device, the second polarized device may polarize the second signal; further optionally, the polarized device may be a polarizer for generating linearly polarized light, wherein polarized directions of the polarizer may be the same or different, and optionally, different polarization directions may be perpendicular to each other. When incident light is linearly polarized light satisfying a certain condition, the reflected light of the skin surface may still be linearly polarized light, and backscattered light may be non-polarized light; by adjusting the polarized direction of the polarizer, ratios of the vital sign components carried by the first signal and the second signal are different.

Optionally, the vital sign information such as, but not limited to, heart rate information may be acquired according to the first signal and the second signal, the first signal and the second signal may be directly used as input signals and the first signal and the second signal which are processed may be used as input signals, and an adaptive noise removal algorithm is applied to obtain heart rate.

DETAILED DESCRIPTION

Figure 1:
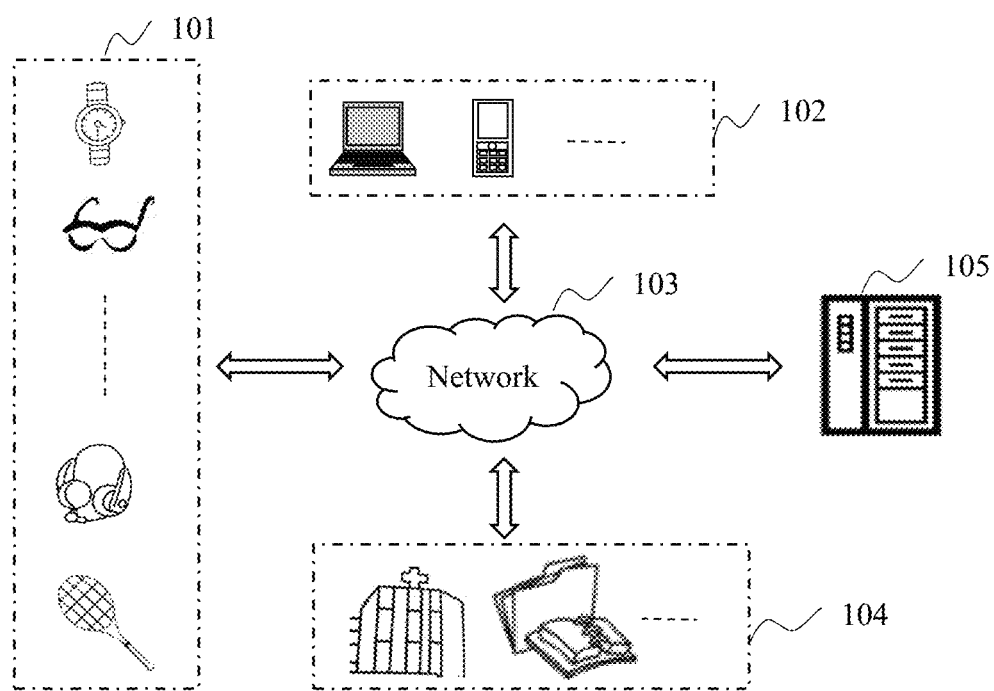
FIG. 1 is a diagram illustrating an application example of a vital signal detection system.

The vital sign detection device and method in this specification may be suitable for various fields, including, but not limited to, medical diagnosis (for example, heart diseases, blood diseases, respiratory diseases, etc.), medical care (for example, intensive patient care, neonatal care, etc.), motion monitoring (for example, long-distance running, short-distance running, swimming, horseback riding, etc.), health monitoring (such as monitoring of infirm individuals), animal protection (for example, rare wildlife animal tracking protection, pet care and maintenance), fat reduction and shaping (for example, overweight people weight loss, bodybuilder shaping), etc.

The above descriptions of the application fields are only specific examples and should not be considered as the only feasible implementation. It is obvious to those skilled in the art that various modifications and changes may be made in the form and detail of the application fields in which the above methods and systems are implemented without departing from the principles after understanding the principles of such a vital sign acquiring method and system, and such modifications and changes are within the scope of the descriptions.

The vital signal detection device in this specification may detect a vital signal of a living body, for example, physical and chemical information such as pulse, blood pressure, blood oxygen, heart rate, body temperature, HRV, BPV, brain waves, ultra-low frequency waves emitted by a human body, breathing, musculoskeletal status, blood glucose, blood lipids, blood concentration, platelet content, height, weight, etc. and process the signal and transmit the signal to a server or terminal. The vital signal detection device may also combine historical data provided by an external data source with vital signal data measured in real time to obtain an appropriate motion recommendation and perform characterization in an appropriate mode. The vital signal detection device may emit a light impinging upon the living body, may detect light signals reflected and scattered by the living body, and may obtain the vital signal of the living body after the light signals being processed. Since the motion/vibration of the living body may bring noise to the measured vital signal, it is considered that a plurality of vital signals are obtained, and noise-removed vital signals are obtained by using a specific algorithm according to the difference between the different signals. For example, the vital signal detection device may detect two or more signals and perform the corresponding de-noising processing to obtain more accurate vital signals.

To describe technical solutions in the embodiments of the present disclosure more clearly, the accompanying drawings needed for describing the embodiments may be briefly introduced below. It is obvious that the drawings in the following descriptions are merely some embodiments of the disclosure, and to those of ordinary skill in the art, the present disclosure may be applied to other similar scenarios according to these drawings without having creative efforts. Unless it is obvious from the language context or otherwise indicated, the same reference numerals represent the same structure or operation.

In the present specification and claims, the terms "a/an," "one," "a kind of" and/or "the" are not specifically singular and may include plural numbers unless otherwise indicated obviously from the context. Generally, terms "comprise" and "include," etc. may only mean including the operations and elements that have been explicitly identified, such operations and elements do not constitute an exclusive list, and a method or a device may also include other steps or elements.

FIG. 1 is a diagram illustrating an application example of a vital signal detection system. The application of the vital signal detection system may include detecting a vital signal of the living body, performing subsequent processing to obtain the corresponding vital sign parameters, storing and displaying the vital sign parameters, etc. The vital signal detection application system may include, but is not limited to, a measurement device 101, a terminal device 102, a network 103, an external data source 104, and a server 105. The measurement device 101, the terminal device 102, the external data source 104, and the server 105 may all communicate directly, or indirectly and bi-directionally via the network 103.

The measurement device 101 may mainly be configured to detect and receive a vital signal of the living body, for example, the device may detect a vital signal of a user during motion. The measurement device 101 may be a medical detection device, a home detection device, a handheld device, and a wearable device. For example, the medical detection device may include, but is not limited to, a blood pressure measurement device, a pulse measurement device, an electrocardiogram monitoring device, etc. The home detection device may include, but is not limited to, a home sphygmomanometer, a home pulse gauge, a home ECG tester, etc. The handheld device may include, but is not limited to, a handheld pulse oximeter, a handheld heart rate meter, a sports equipment with a heart rate measurement capability, for example, a ball, a racquet, a club, a paddle, a treadmill, a bicycle, etc. The wearable device may include, but is not limited to, a watch, glasses, earphones, a wristband, a belt, a shoulder strap, a ring, a necklace, etc. The above is only descriptions of possible forms of the measurement device 101 and does not limit the scope of this application. The measurement device 101 may also be in other forms, for example, a mouse, a global position system (GPS), a mattress, etc.

The terminal device 102 may mainly be configured to display information. The terminal device 102 may be a personal computer, a smart TV, a videophone, a mobile device, for example, a mobile phone, a tablet computer, a smartwatch, etc., or may be other devices with a display function, for example, an ECG monitor, a motion recorder, etc. The terminal device 102 may be local (for example, the smartwatch may be a measurement device and a display screen thereof may serve as a terminal device simultaneously) and may be remote. The way in which the terminal device 102 displays the information may include, but is not limited to, a digital manner, a graphical manner, a curvilinear manner, a language broadcast manner, etc. The information display of the terminal device 102 may be in real time or non-real time. The above is only descriptions of possible forms of the terminal device 102, and does not limit the scope of this application. In some embodiments, the measurement device 101 and the terminal device 102 may be one same device with functions of detecting, processing information and displaying information simultaneously.

The network 103 may be used to implement communications among the measurement device 101, the terminal device 102, the external data source 104, and the server 105. The network 103 may be a single network or a compound network including a variety of networks. The network 103 may be a local area network, a wide area network, or a personal network. The network 103 may be a wireless network or a wired network (for example, a telephone network, a television network, etc.). The network 103 may include a variety of network access points, for example, wired or wireless access points, base stations, or network switching points, etc. The above is only descriptions of possible forms of the network 103 and does not limit the scope of this application. In some embodiments, communication among the measurement device 101, the terminal device 102, the external data source 104, and the server 105 may be wired or wireless, or some of the devices are connected in a wired manner, and some of the devices are connected in a wireless manner.

The external data sources 104 may mainly be configured to provide various external data. The external data refers to other information which correlates with data detected by the measurement device 101. The external data may be individual identification information, for example, name, identification number, contact details, address, educational background, religious belief, emergency contact, etc., which are useful for identifying an individual. The external data may be individual medical record information, for example, an individual related medical record such as a disease treatment record, a medication administration record, a physical examination record, etc. The external data may be individual health record information, for example, a heart rate record, a blood pressure record, a weight record, a body fat percentage record, which may reflect the health history of an individual. The external data may be individual life record information, for example, breakfast composition, water intake, fruit consumption, meat consumption, etc. The external data may be statistical information of various types for a specific target group, for example, an average height of children in an administrative area, an average weight of newborns, an average age at childbirth of pregnant women, etc. The external data may also be a variety of prior explanatory materials (for example, textbooks, essays, medical product manuals, drug manuals, etc.). The external data source 104 may be various databases such as a hospital database, a pet database of a pet hospital, and an animal information database of an animal protection organization, or may be a personal computer, a cell phone, or a library. The above-mentioned individuals may include, but are not limited to, persons, pets, rare animals, experimental animals, etc., and generally refer to all individuals having vital signs. The above is only descriptions of possible forms of the external data source 104, and does not limit the scope of this application. For example, the external data may include vital sign information of a group having certain similarities to a user, wherein the certain similarities described herein may include gender, color, age, height, weight, health status, medical records, etc.

The server 105 may mainly be configured to store information. The server 105 may be a local storage, a cloud storage, including but not limited to a private cloud and a public cloud. The server 105 may be information stored by the server 105, may be vital sign information transmitted by the measurement device 101, may be processed information transmitted by the terminal device 102, or may be individual record information sent by the external data source 104. The above description of the server 105 is merely some possible embodiments and does not limit the scope. In some embodiments, the server 105 may be integrated with the terminal device 102 or may implement functions of the external data source 104.

After detecting information, the measurement device 101 may transmit the information to the terminal device 102, the external data source 104, and the server 105 via the network 103, to perform the corresponding post-processing, and the measurement device 101 may detect various instruction information from the terminal device 102, the external data source 104, and the server 105, and then detect and transmit the corresponding information. The terminal device 102 may detect information detected by the measurement device 101, transmit request information to the external data source 104, combine reference information transmitted by the external data source 104 with the detected information, and display the information in an appropriate manner after data processing or transmit the processed information to the server 105 for storage. For example, the measurement device 101 may be earphones with a heart rate detection function, the earphones detect a heart rate signal of an athlete in running motion and transmit the heart rate signal to the server 105 such as a personal computer; the server 105 may transmit request information to the external data source 104 to request the transmission of the personal data associated with heart rate historical data, duration of running, running pace size, etc. during a period of running time. The server 105 may process the detected data, and obtain a motion recommendation with historical data, for example, maintaining the current speed, speed up, etc., and may transmit the data to the terminal device 102, for example, a tablet computer and earphones of a trainer, the earphones voice broadcast the motion recommendation to the athlete.

Figure 2:
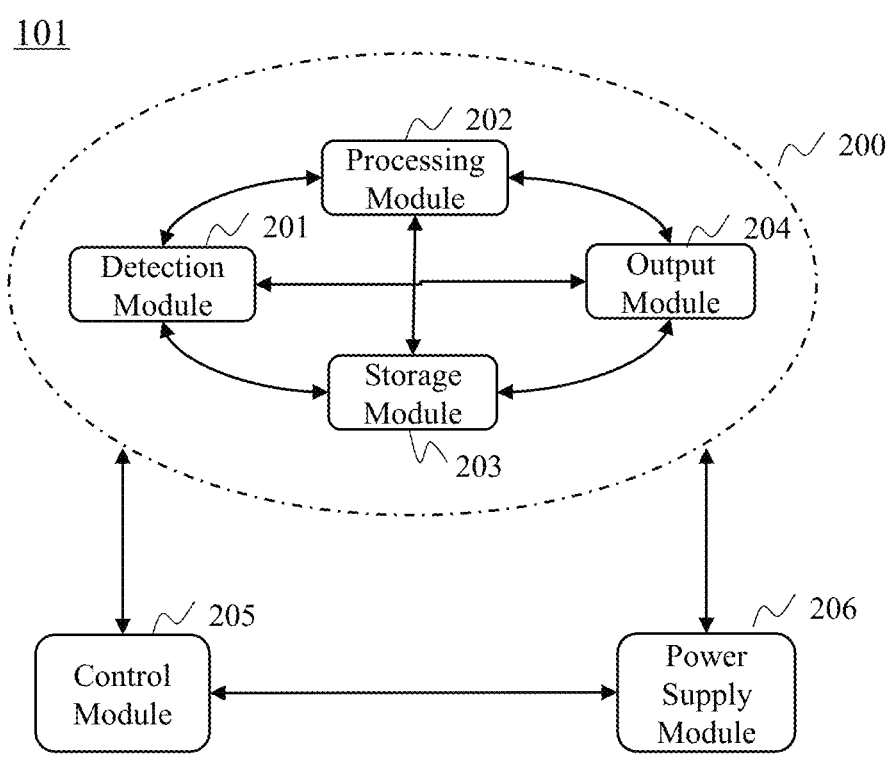
FIG. 2 is a schematic diagram of a measurement device according to an embodiment of the present disclosure.

FIG. 2 is a schematic diagram of a measurement device according to one embodiment of the present disclosure. The measurement device 101 may mainly include, but is not limited to, an execution module 200, a control module 205, and a power supply module 206. The execution module 200 may further include, but is not limited to, a detection module 201, a processing module 202, a storage module 203, and an output module 204. The execution module 200 may mainly be configured to perform detecting, processing, storing, and output operations. The control module 205 may mainly be configured to control operations of the execution module 200 and control start-up and shut-down of the power supply module 206. The power supply module 206 may mainly be configured to provide a power supply for the execution module 200 and the control module 205. The execution module 200, the control module 205, and the power supply module 206 may communicate bi-directionally.

The detection module 201 of the execution module 200 may mainly be configured to detect and receive vital signals of a living body. The signals detected by the detection module 201 may be detected using photoelectric means, for example, photoplethysmography (PPG), or detected using other means. The means of detecting signals may be continuous or may be at intervals. The detected signal may be a single signal or a compound signal including a variety of signals. The processing module 202 may mainly be configured to process the signal. The processing of the signal by the processing module 202 may include, but is not limited to, one or more of noise removal, signal analysis, and signal characterization. The processing module 202 may process the information detected by the detection module 201 and may also process information stored in the storage module 203. Processing module 202 may be essential and may be included in the server 105 or the terminal device 102 in FIG. 1. The storage module 203 may mainly be configured to store information. The storage module 203 may store information by using electrical energy means (for example, RAM, ROM, etc.), may store information by using magnetic energy means (for example, a hard disk, a floppy disk, a magnetic tape, a U-disk, etc.), may store information by using an electro-optic means (for example, CD, DVD), may store information by using magneto-optical means (for example, a magneto-optical disk), and may also store information by using other physical means (for example, paper storage). The storage module 203 may store information detected by the detection module 201 and may also store information processed by the processing module 202. The storage module 203 may not be essential, and the storage function may be implemented by the server 105 or the terminal device 102 in FIG. 1. The output module 204 may mainly be configured to output information, output information detected by the detection module 201, output information processed by the processing module 202, or output information stored in the storage module 203. The output module 204 may transmit the above information to the server 105, the terminal device 102, or the external data source 104 via the network 103. The signal output by the output module 204 may be in the form of numbers, graphics, voice, video, audio, etc.

The output may be in real time or non-real time and may be output by the measurement device 101 actively or may be output after request information is transmitted by other external devices. The output module 204 may support wired communication standards, for example, telephone, television, etc., and may also support wireless communication standards, for example, Bluetooth, infrared, RF, IEEE802.11, etc.

The control module 205 may mainly be configured to perform various control operations of the measurement device 101. The control module 205 may control the detection frequency, the detection time, the detection measns, etc. of the detection module 201, may also control the processing method of the processing module 202, may also control the storage of the storage module 203, may also control the output time, the output way, etc. of the output module 204, and also may control the start-up and shut-down of the power supply module 206, for example, the mechanical control, electrical control, etc. The communication of requests and command information among other devices, for example, the server 105, the external data source 104, the terminal device 102, and the measurement device 101 may be accomplished by the control module 205. The power supply module 206 may mainly be responsible for the energy supply of the measurement device 101. The power supply module 206 generally refers to a device which may provide an energy supply. The power supply module 206 may be a fuel cell, a dry cell, a storage battery, a solar cell, a thermoelectric cell, a bioenergy cell, etc. The power supply module 206 may include a charging interface, for example, microUSB, miniUSB, Lighting, etc.

Figure 3:
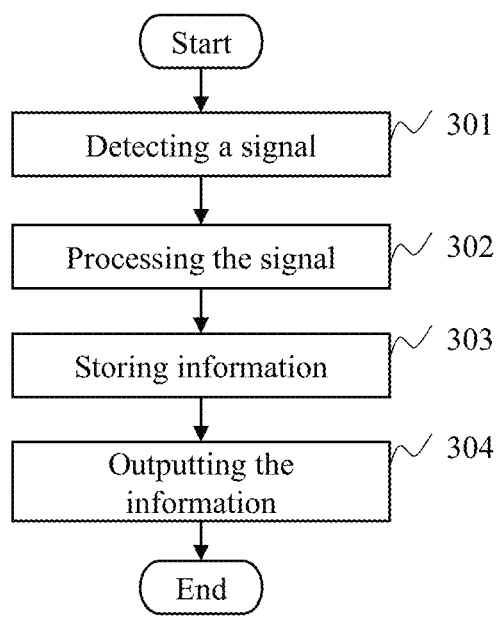
FIG. 3 is a flowchart of a measurement device according to an embodiment of the present disclosure.

FIG. 3 is a flowchart of a measurement device according to one embodiment of the present disclosure. At step 301, a vital signal may be detected. The detected signal may be a signal obtained by directly measuring a living body, for example, a signal measured using a PPG method (also referred to a PPG signal). The detected signal may also be external data from the external data source 104 via the network 103, for example, personal identification information, personal health record, personal life record, etc. The detected signal may further be information from the server 105 via the network 103, such as history information uploaded to the server 105. The step 301 may be performed by the detection module 201. At step 302, the detected signal may be analyzed and processed. The analyzed and processed signal may be a signal detected in step 301, and may also be a signal transmitted by the storage module 203 after a request is transmitted to the storage module 203. The analysis processing of the signal may include but not limited to noise removal, signal analysis, and signal characterization. The step 302 may be performed by the processing module 202. At step 303, the information may be stored. The stored information may be the signal detected in step 301, and may also be the analyzed and processed signal in step 302. The step 303 may be performed by the storage module 203. At step 304, the signal may be outputted. The output signal may be the detected signal by the detection module 201, may also be the processed signal by the processing module 202, and may also be the stored signal by the storage module 203. The step 304 may be performed by the output module 204.

Figure 4:
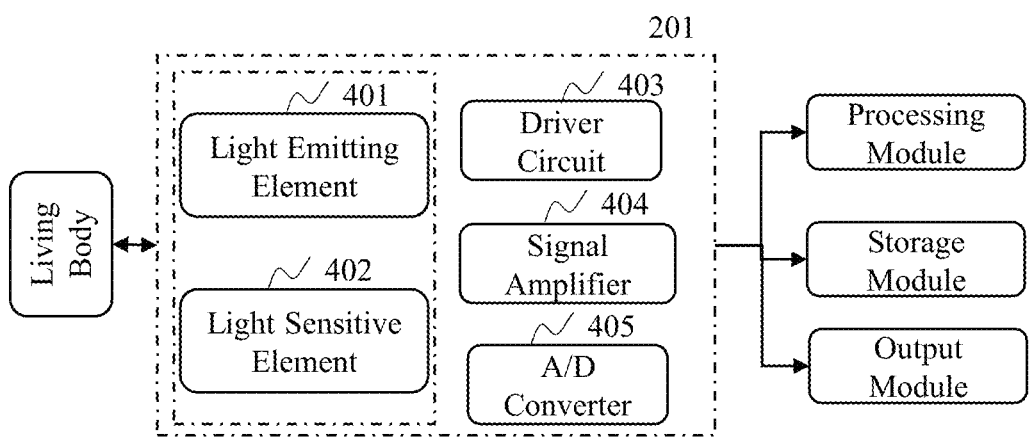
FIG. 4 is a schematic diagram of a detection module according to an embodiment of the present disclosure.

FIG. 4 is a schematic diagram of a detection module 201 according to one embodiment of the present disclosure. The detection module 201 may mainly be used to detect a needed signal. The detection module 201 may include but not limited to a light emitting element 401, a light sensitive element 402, a driver circuit 403, a signal amplifier 404, and an A/D converter 405. The light emitting element 401 may generate light radiation into a living body. The light emitting element 401 may be a thermal radiation source or may be an excitation radiation source, for example, a light emitting diode (LED). The light emitted by the light emitting element 401 may include a single wavelength or different wavelengths, and may be polarized or unpolarized. The light emitting time of the light emitting element 401 may be fixed, or have a fixed interval. The light sensitive element 402 may be used to detect the light reflected and scattered by a the living body, and convert the detected light signal into an electrical signal. The light sensitive element 402 may be a photoconductive device, such as a photoresistor, may also be a photovoltaic device, such as a photodiode, a phototransistor, and a photoelectric field effect tube, and may also be a photodetector. The driver circuit 403 may be used to drive the light emitting element 401 to emit light. The signal amplifier 404 may amplify an electrical signal transmitted by the light sensitive element 402. The A/D converter 405 may perform an analog-digital conversion (A/D conversion) on a detected electrical signal.

Figure 5:
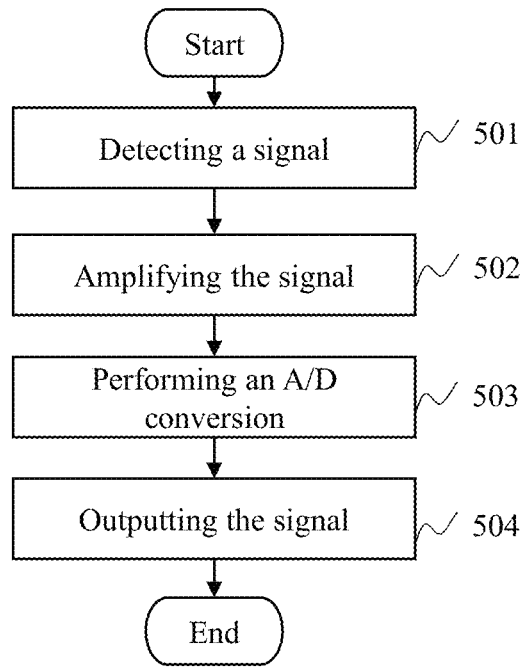
FIG. 5 is a flowchart of a detection module according to one embodiment of the present disclosure.

FIG. 5 is a flowchart of a detection module 201 according to one embodiment of the present disclosure. At step 501, a desired signal may be detected. The step 501 may be performed by the light emitting element 401 and the light sensitive element 402 together. The light emitting element 401 may first generate light specified by a parameter, and the parameter may be a wavelength, a light intensity, a phase, a polarization state of the light, etc. The light may emit to a living body, and the living body may reflect, absorb, and scatter the light. The light sensitive element 402 may detect the reflected and scattered light and convert the light signal into an electrical signal. At step 502, the detected signal may be amplified as necessary. In some embodiments, the detected signal does not need to be amplified, and the step 502 may not be executed. The step 502 may be performed by the signal amplifier 404. At step 503, A/D conversion may be performed on the amplified signal. Since the detected signals are analog signals, and the subsequent processing of the processing module 202 and the storage of the storage module 203 need digital signals, it is necessary to perform an analog-digital conversion to obtain digital signals. The step 503 may be performed by the A/D converter 405. At step 504, the signal may be outputted. The output signal may be output to the processing module 202 for the subsequent processing, may be output to the storage module 203 for the storage, and may also be output to the output module 204, and may further be transmitted to the server 105, the terminal device 102, or the external data source 104.

Figure 6:
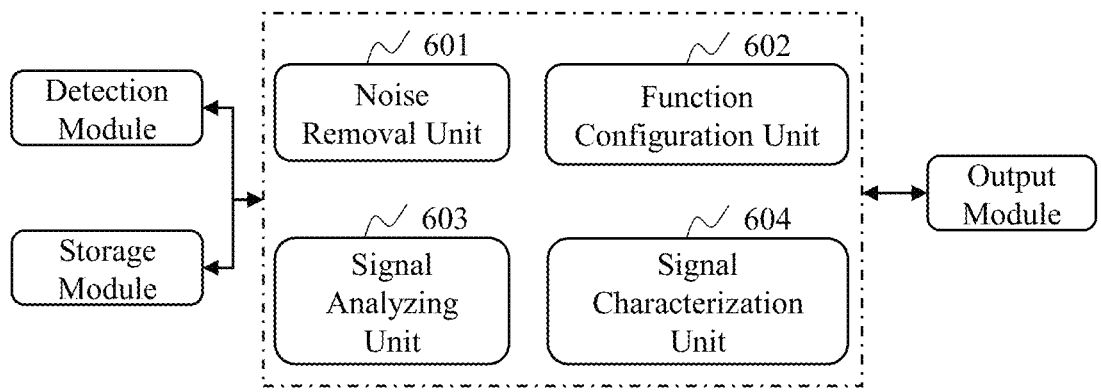
FIG. 6 is a schematic diagram of a processing module according to one embodiment of the present disclosure.

FIG. 6 is a schematic diagram of a processing module 202 according to an embodiment of the present disclosure. The processing module 202 may mainly be used to analyze and process a signal. The processing module 202 may include but not limited to a noise removal unit 601, a function configuration unit 602, a signal analyzing unit 603, and a signal characterization unit 604. The noise removal unit 601 may remove the noise of information detected by the detection module 201. Signals detected by the detection module 201 may be two signals with correlation, and the two signals need to be denoised, removing signals independent from heart rate, such as movement or vibration signals during a human motion. The function configuration unit 602 may perform a function configuration, and the configured function includes but is not limited to a heart rate detection, a motion signal detection, a health signal detection, etc. The signal analyzing unit 603 may analyze a signal. The detection module 201 may transmit an electrical signal, and after certain analysis of the electrical signal, a desired vital signal may be obtained. According to different function configurations, the signal analyzing unit 603 may be used to analyze the electrical signal into a pulse signal, a heart rate signal, an oxygen consumption signal, a fat consumption signal, etc. An analyzed signal may be characterized by the signal characterization unit 604. The characterization may include but not limited to a digital characterization, a curve characterization, a graphical characterization, a real-time speech characterization, a video characterization, etc.

Figure 7:
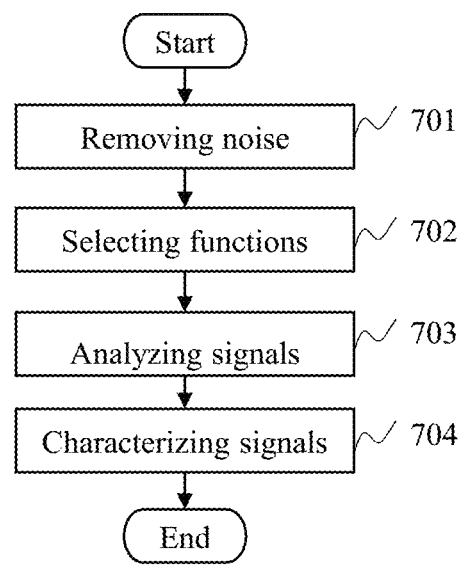
FIG. 7 is a flowchart of a processing module according to one embodiment of the present disclosure.

FIG. 7 is a flowchart of a processing module 202 according to an embodiment of the present disclosure. At step 701, the noise of a detected signal may be removed to obtain a need electrical signal. The noise removal processing may include but not limited to a single parameter removal method, a multi-parameter removal method, an wavelet analysis, a Fourier transform, an adaptive filtering method, etc. The step 701 may be performed by the noise removal unit 601. At step 702, the function(s) of the processing module 202 may be configured, and the processing function (s) to be performed by the processing module 202 may be selected. The step 702 may be performed by the function configuration unit 602. At step 703, electrical signals may be analyzed into different signals according to the different function configurations. The step 703 may be performed by the signal analyzing unit 603. At step 704, signals are characterized as signals in different forms according to different characterization needs. The step 704 may be performed by the signal characterization unit 604. The step 701, the step 702, the step 703, and the step 704 may be performed sequentially, or the step 702 may be first performed, and then the step 701, the step 703, and the step 70 may be performed after the function(s) are configured.

Figure 8:
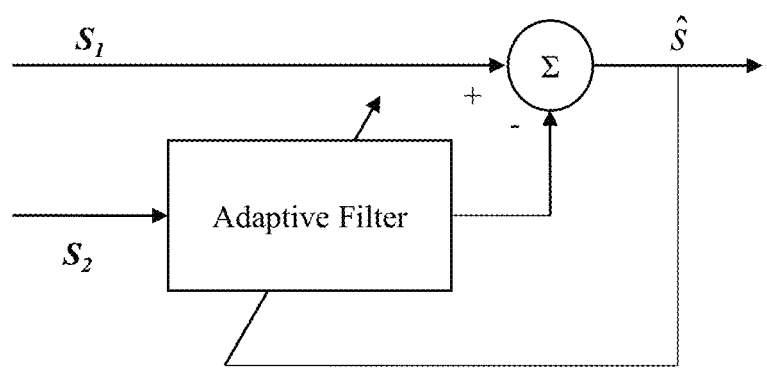
FIG. 8 is a schematic diagram of noise removal using an adaptive filtering method according to one embodiment of the present disclosure.

When vital signs are being detected, a body's motion may interfere with the detection of a signal; thus the detected signal includes a certain amount of noise. There are many noise removal means, for example, a single parameter removal method, correcting a detected single signal according to a specific processing algorithm for detecting signals, and a multi-parameter removal method may also be used, which is, detecting multiple signals, designating one or more detected signals as reference signals, based on which the noise is removed by specific algorithms. In some embodiments, an adaptive noise removal embodiment is shown in FIG. 8. $S_1$ and $S_2$ are input signals, an Adaptive Filter is a filter that may adjust or correct a signal, the mixer may perform comparison processing on input signals, and the signal $\hat{s}$ is finally output. The processing may be represented as:

$$\hat{s} = S_1 - w \cdot S_2 \qquad (1)$$

wherein, w represents a coefficient of the filter and may be automatically adjusted according to the output signal $\hat{s}$. In one embodiment, $S_1$ may include vital sign information and noise information, and $S_2$ may also include noise information without including vital sign information. In another embodiment, $S_1$ may include vital sign information and noise information, and $S_2$ may also include noise information and vital sign information. However, ratios of the vital sign information to the noise information in $S_1$ and $S_2$ are different, and an appropriate filter coefficient w may be solved according to a feedback, and a desired signal is obtained.

Herein, the input signal described herein may include a signal of different types. For example, the input signal may include a light signal, an electrical signal, a magnetic signal, a sound signal, a temperature signal, a displacement signal, or the like, or a combination thereof. The input signal may be an signal detected at a reception end (for example, a light signal, an electrical signal, a magnetic signal, a sound signal, a temperature signal, a displacement signal, etc. detected at the detecting end), and may also be a signal obtained after a certain processing of a signal detected at the reception end (for example, a light signal, an electrical signal, a magnetic signal, a sound signal, a temperature signal, a displacement signal converted after detecting the light signal, and the electrical signal, the magnetic signal, the sound signal, the temperature signal, the displacement signal at a detecting end). The reception end may be a sensor of different types and may include but not limited to a photoelectric sensor, a displacement sensor, an acceleration sensor, a vibration sensor, a mechanical sensor, a temperature sensor, a barometric pressure sensor, etc. The type of a photoelectric sensor includes but is not limited to a diffuse reflective type photoelectric sensor, a thru-beam photoelectric sensor, a distance type photoelectric sensor, a U-shaped photoelectric sensor, a fiber optic photoelectric sensor, etc.

It should be noted that the embodiment of the adaptive noise removal is merely an example used in the present disclosure, those skilled in the art may make various modifications and changes in the form and detail of the embodiment without departing from the basic principles after understanding the basic principles of detecting a vital signal and removing the noise, and such modifications and changes are within the scope of the descriptions. For example, input signals may include but not limited to $S_1$ and $S_2$, and include two or more input signals, and each input signal may be a signal detected from one or more sensors. The coefficient w of a filter may be obtained according to the negative feedback of output signals, may also be obtained according to the forward feedback of other input signals, and may further be obtained according to the negative feedback of part of input signals and the forward feedback of part of input signals. The coefficient w of a filter may be obtained by the system calculation, may also be set by a user, may also be obtained from an external device or device in a wired or wireless manner, or may be obtained by other means. For example, since the human vital signs are different at different times in the day, the corresponding coefficient w of the filter may be selected at different times in the day, and the corresponding parameter w may also be set in different dates, months or seasons.

Figure 9:
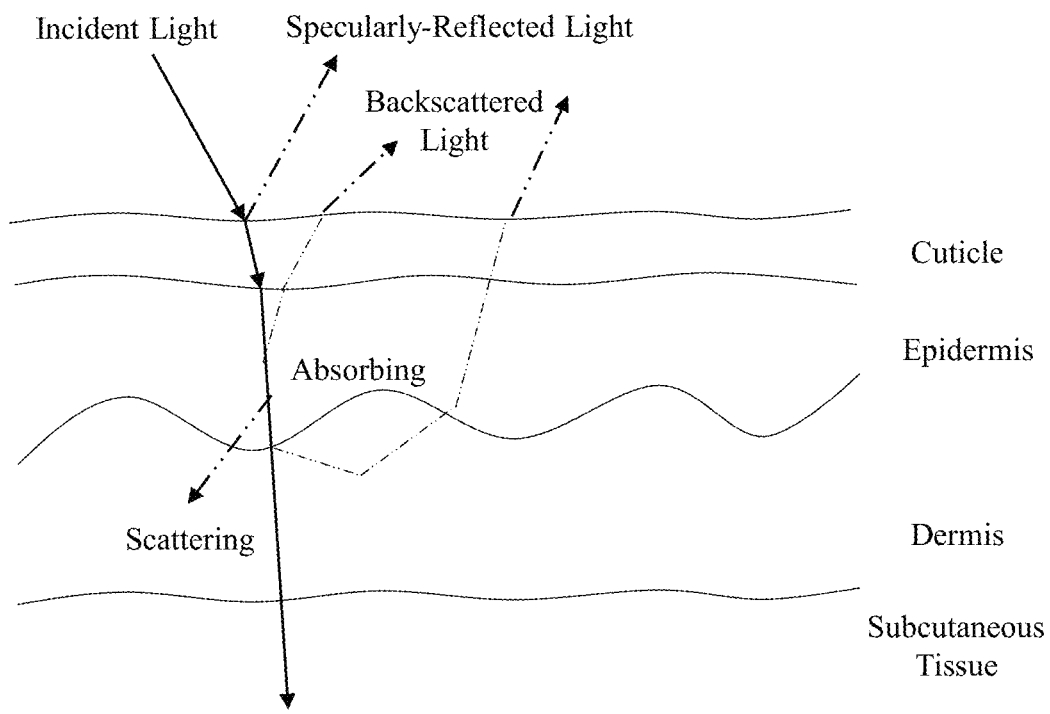
FIG. 9 is a hierarchical structure diagram and an optical model view of human skin tissue according to one embodiment of the present disclosure.

The input signals $S_1$ and $S_2$ may separately include light signals of vital sign information and noise information. After light travelling in a medium (for example, a living body), a detected light may carry information of the medium layer. When a light emits to some medium (a solid, gas or liquid), a portion of the light may be reflected by the medium, and a portion of the light may penetrate the medium or be absorbed by the medium. The reflection, absorption, transmission, etc. of the light depends on an attribute of the medium on which the light propagates. Take human skin tissue as an example, as shown in FIG. 9, the human skin tissue is formed of epidermis, dermis, subcutaneous tissue, and cutaneous appendages. The epidermis does not include blood vessels, the thickness of the epidermis varies depending on where it is located, and the thickness of most of the epidermis is around 100 μm. The dermis is located between the epidermis and the subcutaneous tissue, is mainly formed of connective tissue, and is divided into papillary and reticular layers from the outside to the inside. The papillary layer is rich in blood capillaries. The reticular layer includes many large blood vessels, which are located mainly at the base of the dermis. The human skin tissue formed of multiple layers in different structures includes optical properties equivalent to a chaotic medium with a high scattering property. When a light having a certain wavelength impinges on the human skin, a portion of the light is reflected by the skin surface to obtain specularly-reflected light. After refracted by the skin surface, another portion of the light sequentially enters the epidermis and dermis of the skin tissue, is scattered and absorbed by the skin tissue, and finally escapes the skin surface to obtain backscattered light. According to a scattering theory, the backscattered light may include ballistic photons, serpentine photons, and diffuse photons. The ballistic photons and the serpentine photons return to the skin surface after a small amount of scattering and absorption in the skin tissue, this portion of the scattered light has a low penetration depth, usually does not reach the dermis and barely carries information on the internal tissue structure of the skin. The diffuse photons return to the skin surface again after repeated scattering in the skin, and the portion of the scattered light usually penetrates the dermis and carries information on the internal tissue structure of the skin, for example, the increase or decrease of blood flow in large blood vessels in the dermis. When the polarized light emits to the human skin, the specularly-reflected light has the same polarized characteristics. The ballistic photons and the serpentine photons undergoing fewer scattering times have the same polarized characteristics, but the diffuse photons undergoing more scattering times do not have polarized characteristics. In the present specification, the ballistic photons and the serpentine photons undergoing fewer scatterings are referred to as less backscattered light, the diffuse photons undergoing more scatterings are referred to as multiple backscattered light, and the specularly-reflected light and the less backscattered light are referred to as superficially reflected light. The signal reflected by a living body (for example, skin) in the present specification may include the reflected light of the living body (for example, skin) surface, may also include the scattered light scattered by the living body tissue, and may include both reflected light of the skin and scattered light scattered by the skin tissue. In some embodiments, transmission and detecting of a light signal may be performed by a PPG sensor, and the PPG sensor may include a number of light sources and optical detectors. When a light having a certain wavelength passes through biological tissue, the human skin (skin, fat, blood, muscle, etc.) will scatter and absorb the light, thereby attenuating the intensity of a detected light. When an artery vessel is pulsating or a vein is filling in a light transmitting region, the amount of light absorption of the blood will change as blood flow increases or decreases. The optical detector adjacent to the skin may detect the changes: when the blood vessels are filled, the amount of light absorption of the blood is maximum, and the intensity of an outgoing light detected by the detector is the smallest, whereas when the blood vessels contract, the amount of light absorption of the blood is minimum, and the intensity of an outgoing light detected by the detector is the greatest. Therefore, the PPG sensor may trace fluctuation signals formed by changes in intravascular volume, thereby obtaining information related to vital signs (including but not limited to a pulse wave, heart rate, blood pressure, etc.). According to the noise removal embodiment described in Equation (1), the measurement of a pulse wave may be implemented by different input signals obtained by one or more PPG sensors. For example, the input signal $S_1$ may include the PPG signal, and the signal $S_2$ does not include the PPG signal. As another example, a ratio of a PPG signal to a noise signal in the input signal $S_1$ is different from a ratio of the PPG signal to the noise signal in the signal $S_2$.

The above detection of a PPG signal only gives an example of testing a pulse wave and does not represent the only method. It may be apparent to those skilled in the art that various changes may be made in the form and content of examples without departing from the related principles, and such changes are within the scope of the descriptions. For example, the detection of vital signs is not limited to detection of a pulse wave, and may also include one or more combinations of the detection of blood pressure, blood oxygen saturation, heart rate variability, heart murmur, etc. Vital sign information included in an input signal includes but is not limited to a measurement of various physiological parameters in a living body, for example but is limited to one or more of height, weight, vital capacity, heartbeat parameters, blood glucose levels, blood viscosity measurements, vasodilation pressure, vasoconstriction, blood flow parameter determination, PPG signal peaks and troughs, ECG signal peaks and troughs, pulse rate, heart rate, blood lipid level, vascular tone, skin tone, brain wave frequency, gastrointestinal motility, hepatobiliary organ morphology, gastrointestinal mucosa parameters, antibody content, bio-enzyme content, etc.

A change in detecting modes of a signal, for example, but not limited to a change in the configuration of a signal detecting device, may obtain the input signals $S_1$ and $S_2$ including various vital sign information and noise information. In some embodiments, the input signals $S_1$ and $S_2$ are related to the depth of light penetrating into the skin tissue structure. For example, if the depth of light penetrating into the skin is deeper, the blood vessels may exist in the light transmitting region, and the input signals may include PPG signals, whereas if the depth of light penetrating into the skin is shallower, the blood vessels may not exist in the light transmitting region, and the input signals may not include PPG signals, or include fewer PPG signals in the input signals. According to a skin tissue structure and an optical model, the average depth of light penetrating into tissues is related to a distance between a light source and a detector. For example, if the distance between the light source and the detector is relatively small, the average depth of light penetrating into the skin is shallower, and less information of the deep medium is carried, whereas the distance between the light source and the detector is relatively large, the average depth of light penetrating into the skin is deeper, and more information of the deep medium is carried. In the skin tissue, if the average depth of light penetrating into the skin is deeper, more vital sign information (for example, the PPG signal) is detected. Signals having different ratios of a pulse wave component may be obtained using a difference between positions of a light source and a detector r.

Figure 10:
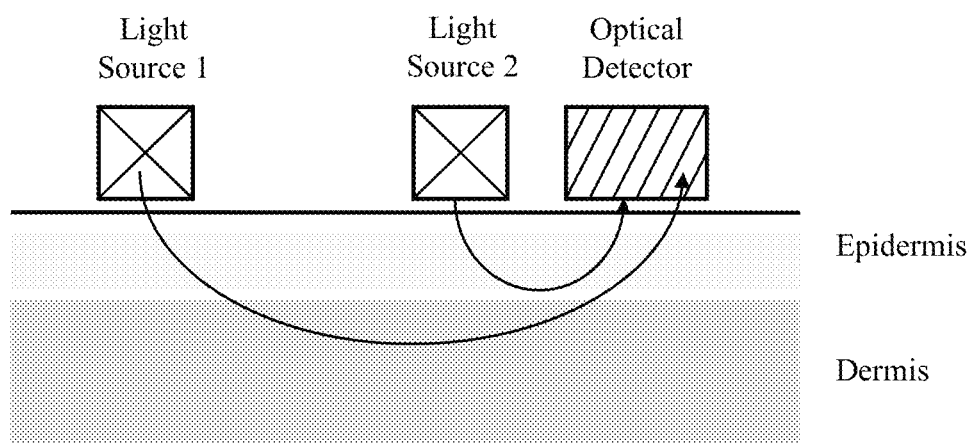
FIG. 10 is a schematic diagram of a sensor using a difference between positions of a light source and a detector.

FIG. 10 is a schematic diagram of a sensor using the difference between positions of a light source and a detector. The sensor may include one optical detector and two light sources. The optical detector may be a device which may detect a light signal having a certain wavelength, and read information of the light signal, such as, a photoelectric sensor. Herein, the light source may only include a light having a single wavelength or may also include a light within a wavelength range, for example, a light having a wavelength of 700 nm or another wavelength, or a light within a wavelength range 600 nm to 700 nm, or other wavelength ranges. The light described herein may be a light in a visible range, and for example, but is not limited to a red light, a yellow light, a blue light, a green light, a violet light, etc., or may be a non-visible light, for example, an infrared light, an ultraviolet light, etc. The optical detector, the light source 1, and the light source 2 may all be adjacent to the skin, and preferably, the optical detector, the light source 1, and the light source 2 may be located on a straight line. The light source 1 and the light source 2 may be located on the same side of the optical detector, and preferably, the distance between the light source 1 and the optical detector is relatively large, and the distance between the light source 2 and the optical detector is relatively small. The distance between the light source 1 and the optical detector is larger than the distance between the light source 2 and the optical detector. During operation, the light source 1 and the light source 2 may emit beams alternately or emit beams at the same time. The intensity of the light source 1 and the light source 2 may be adjusted, for example, the intensity of the light sources can be automatically adjusted according to an ambient brightness and the intensity of external light, may also be fed back according to the intensity of the light signal detected by the optical detector, and may further be adjusted according to an input from the outside. Emission wavelengths of the light source 1 and the light source 2 may be the same or different. After the beams emitted by the two light sources reach the skin, since distances from the light source 1 and the light source 2 to the optical detector are different, average depths of beams emitted by the light source 1 and the light source 2 penetrating into the skin tissue are different, and ratios of a vital sign (for example, pulse wave) component signal (for example, PPG signal) are different. For example, the distance between the light source 1 and the optical detector is relatively large, the average depth of the beam emitted by the light source 1 penetrating into the skin tissue is deeper, and a ratio of a vital sign (for example, pulse wave) component signal carried by the scattered light signal of the beam emitted by the light source 1 after the skin function is larger. The distance between the light source 2 and the optical detector is relatively small, the average depth of a beam emitted by the light source 2 penetrating into the skin tissue is shallower, and a ratio of the pulse wave component signal carried by the scattered light signal of the beam emitted by the light source 2 after the skin function is smaller. The beams carrying motion information and different ratios of vital sign information are detected by the optical detector, the detected signals are a photoelectric signal 1 and a photoelectric signal 2 which are represented as $I_1$ and $I_2$ respectively, and the detected photoelectric signal 1 and photoelectric signal 2 may be directly taken as the input signals $S_1$ and $S_2$ in FIG. 8, or may be taken as the input signals $S_1$ and $S_2$ after a certain processing and conversion.

The above description is merely specific embodiments of the present disclosure, and the protection scope of the present disclosure is not limited to the embodiments described above. Those of ordinary skill in the art can make modify and change the present embodiment described above without making creative efforts, and the modifications and changes are in the protection scope of the present disclosure.

For example, the components of a sensor may include one optical detector and two light sources; two optical detectors and one light source; two optical detectors and two light sources (for example, a sensor 1 includes a light source 1 and an optical detector 1, and a sensor 2 includes a light source 2 and an optical detector 2); or a combination of any number of optical detectors and any number of light sources.

As another example, the components of a sensor are limited to be adjacent to the skin surface and are located at a distance above the skin, and one or more light sources and one or more detectors are located at a distance above the skin. Distances between different light sources and the skin, and distances between different optical detectors and the skin may be the same or be different, and the distances between different light sources and the skin may be the same or be different from the distances between different optical detectors and the skin. If one or more or all of the components of the sensor are located at a distance above the skin, preferably, distances between the components of the sensor and the skin may be 2 to 10 mm, and more preferably, the straight distance between the components of the sensor and the skin may be 7 mm.

As another example, if the components include two optical detectors and one light source, the distance between the light source and the optical detector 1 may be larger than the distance between the light source and the optical detector 2. Preferably, the distance between the light source and the optical detector 1 is larger than 5 mm, and the distance between the light source and the optical detector 2 is less than 5 mm. More preferably, the distance between the light source and the optical detector 1 is larger than 8 mm. When the components include two optical detectors and two light sources, the distance between the light source 1 and the optical detector 1 may be larger than the distance between the light source 2 and the optical detector 2. Preferably, the distance between the light source 1 and the optical detector 1 is larger than 5 mm, and the distance between the light source 2 and the optical detector 2 is less than 5 mm. More preferably, the distance between the light source 1 and the optical detector 1 is larger than 8 mm.

As another example, relative positions between optical detectors and light sources may be different. For example, if the components include one optical detector and two light sources, the two light sources may both be located on one side of the detector, or the two light sources may respectively be located on opposite sides of the detector. If the components include two optical detectors and one light source, the two optical detectors may be located on the same side of the light source, or the two optical detectors may be located on opposite sides of the light source. If the components include two optical detectors and two light sources, relative positions between the optical detectors and the light sources may be: the optical detector 1 and the optical detector 2 being located between the two light sources, the optical detector 1 and the optical detector 2 separately being located on opposite sides of the two light sources, the optical detector 1 and the optical detector 2 both being located on one side of the two light sources, or the optical detector 1 being located on one side of the two light sources and the optical detector 2 being located between the two light sources. If the components include any number of optical detectors and any number of light sources, relative positions between the optical detectors and the light sources may be determined according to the actual application.

The examples described above are only an embodiment described in connection with FIG. 10 of the present disclosure, and the protection scope of the present disclosure is not limited to the alternatives described above. Those of ordinary skill in the art can combine alternatives described above without making creative efforts, and the alternatives are also in the protection scope of the present disclosure.

Figure 11:
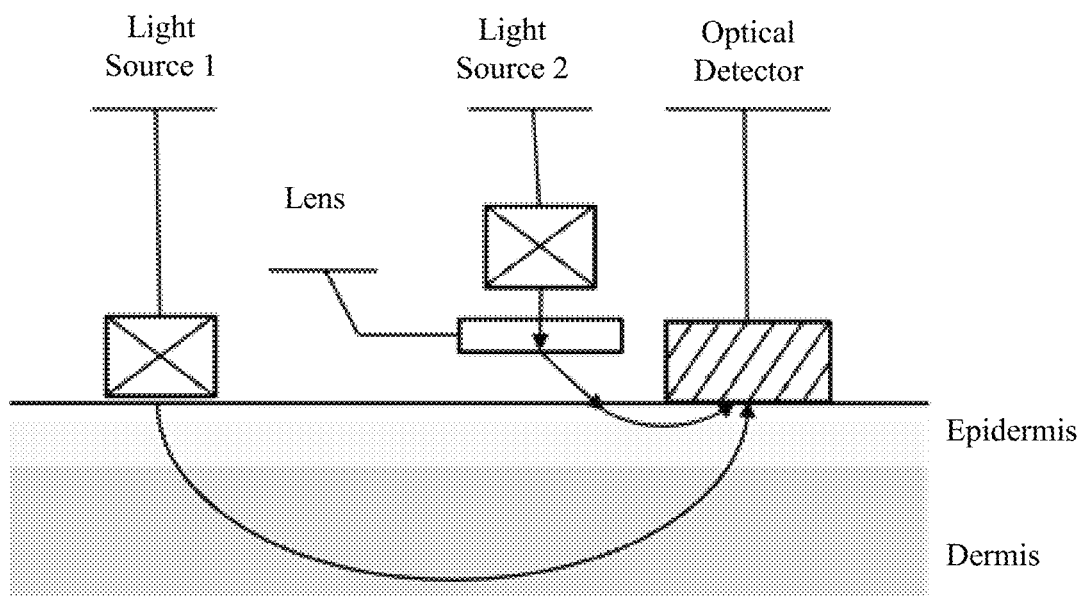
FIG. 11 is a schematic diagram of a sensor using a lens to change a transmission direction of light.

Changing an angle of a light entering or leaving the skin may also change the average distance of light penetrating into the skin tissue, thereby obtaining the input signals $S_1$ and $S_2$ characterizing different vital signals. FIG. 11 is a schematic diagram of a sensor using a lens to change a transmission direction of light according to the present disclosure. The sensor may include one optical detector, two light sources, and one lens. The light source 1 may be adjacent to the skin, the optical detector may be located at a distance above the skin, the lens may be located between the light source 2 and the skin, and the light source 1 and the light source 2 may be located on the same side of the optical detector. The lens may be used to change a direction of a beam emitted by the light source 2, thus the light is at an angle with respect to the skin. The angel may be any value in a range of, for example, 0° to 180°, lens types include but are not limited to a concave lens, a convex lens, a plano-convex lens, a plano-concave lens, a meniscus lens, or other device for changing a direction of light, for example, a light guide or a prism having a certain shape (for example but not limited to a triangular prism). The distance between the light source 1 and the optical detector is relatively large, and the distance between light source 2 and the optical detector is relatively small. If the two light sources and the optical detector operate, the light source 1 and the light source 2 may emit beams alternately or emit beams at the same time. Emission wavelengths of the light source 1 and the light source 2 may be the same or different. After the beams emitted by the two light sources reach the skin, since distances from the light source 1 and the light source 2 to the optical detector are different and angles of light penetrating the skin are different, average depths of the beams emitted by the light source 1 and the light source 2 penetrating into the skin tissue are different and ratios of the vital sign components carried by the signal are different. For example, the distance between the light source 1 and the optical detector is relatively large, the incident angle of light entering the skin is larger, such that the depth of the beam emitted by the light source 1 penetrating into the skin tissue is larger and the ratio of the pulse wave component signal carried by the scattered light signal of the beam emitted by the light source 1 after the skin function is larger. The distance between the light source 2 and the optical detector is relatively small, the incident angle of light entering the skin is smaller, such that the depth of the beam emitted by the light source 2 penetrating into the skin tissue is smaller and the ratio of the pulse wave component signal carried by the scattered light signal of the beam emitted by the light source 2 after the skin function is smaller. Beams carrying motion information and different ratios of the pulse wave information are detected by the optical detector, and the detected signals are a photoelectric signal 1 and a photoelectric signal 2 which are represented as $I_1$ and $I_1$. $I_1$ and $I_2$ may be used as the signal to be processed and the reference signal respectively, and motion artifacts are removed by the adaptive noise removal algorithm described in connection with FIG. 8.

The description above is merely specific embodiments of the present disclosure, and the protection scope of the present disclosure is not limited to the embodiments described above. Those of ordinary skill in the art can make modify and change the present embodiment described above without making creative efforts, and the modifications and changes are in the protection scope of the present disclosure.

For example, the components of the sensor may include one or more lenses (or another device for changing a direction of light). For example, the lenses (other similar devices for changing a direction of light) may be located between all optical detectors and the skin, may be located between part of the optical detectors and the skin, may be located between all light sources and the skin, may be located on part of the light sources and the skin, may be only located on the optical detector and the skin, or may also be only located between the light source and the detector. Preferably, different types of lenses may be adopted between different optical detectors and the skin or be adopted between different light sources and the skin (other similar devices for changing a direction of light). The detecting modes of the signal may also be changed by polarized characteristics of the light source. After the light source irradiates the skin, the light is reflected on the skin surface, the remaining portion is transmitted and entered into the tissue, and the portion of the light will be scattered in and absorbed by the tissue. After the multiple scattering and absorption, a portion of the light escapes the skin in back-scattered light manner, and the portion of the light is the backscattered light. The portion of the light carries the rich information of the underlying tissue and is mixed with the reflected light of the skin surface, which form the reflected signal. The reflected light of the skin surface and the backscattered light have different polarized characteristics. For example, if the incident light is linearly polarized light satisfying a certain condition, the reflected light of the skin surface may still be linearly polarized light, and the backscattered light entering the tissue basically losses the polarized characteristics due to the multiple scattering. Therefore, at least two different signals may be obtained by the different polarized characteristic of the reflected light of the skin surface and the backscattered light.

Figure 12:
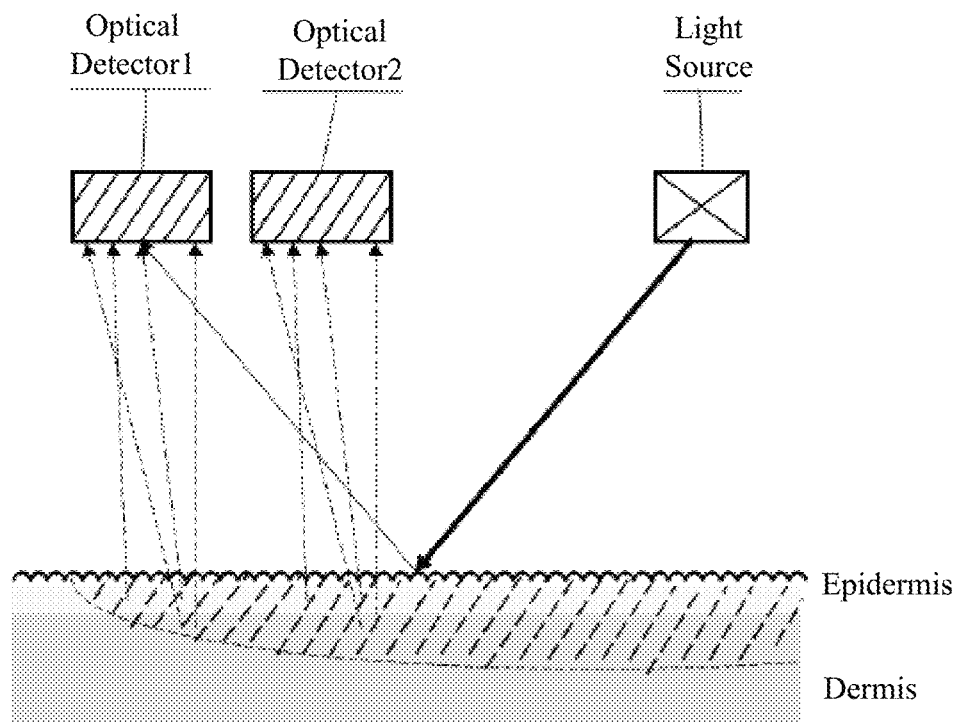
FIG. 12 is a schematic diagram of a sensor using polarized characteristics of a light source.

FIG. 12 is a schematic diagram of a sensor using polarized characteristics of a light source according to the present disclosure. The sensor includes one light source capable of generating linearly polarized light and two optical detectors which may detect the light having different polarized characteristics. The polarized direction of the linearly polarized light of the light source may be a direction perpendicular to an incident surface, may also be a direction parallel to the incident surface, or may be a direction at an angle to the incident surface. The light source and the optical detector may all be located at a distance from the skin or may all be adjacent to the skin surface. The distance between two detectors may be relatively small. If the sensor operates, the optical detector 1 and the optical detector 2 may detect signals during the light source emitting the light, respectively obtaining the photoelectric signal 1 and the photoelectric signal 2. Each of the photoelectric signal 1 and the photoelectric signal 2 include the superficially reflected light and the multiple backscattered light of the living body. If the light source and the optical detector are located at a distance from the skin, the optical detector may detect the reflected light of the skin surface, the less backscattered light, and the multiple backscattered light. Since the superficially reflected light is still the linearly polarized light, and the multiple backscattered light is non-polarized light, the superficially reflected light component and the multiple backscattered light component included in the photoelectric signal 1 and the photoelectric signal 2 have different characteristics. If the light source and the optical detector are adjacent to the skin surface, the optical detector may detect the less backscattered light and the multiple backscattered light without detecting the scattered light of the skin surface. Since the less backscattered light is still the linearly polarized light and the multiple backscattered light is non-polarized light, the less backscattered light component and the multiple backscattered light component included in the photoelectric signal 1 and the photoelectric signal 2 have different characteristics. The value of the intensity of the superficially reflected light and the multiple backscattered light may be determined according to the different characteristics of the superficially reflected light and the multiple backscattered light. The motion artifacts may be removed by the adaptive filtering algorithm based on the determined value. The description above is merely specific embodiments of the present disclosure, and the protection scope of the present disclosure is not limited to the embodiments described above. Those of ordinary skill in the art can make modify and change the present embodiment described above without making creative efforts, and the modifications and changes are in the protection scope of the present disclosure.

For example, the components of the sensor may include one optical detector and two light sources, two optical detectors and one light source, two optical detectors and two light sources (for example, the sensor 1 includes the light source 1 and the optical detector 1, and the sensor 2 includes the light source 2 and the optical detector 2), or a combination of any number of optical detectors and any number of light sources.

For example, the components of the sensor using the polarized characteristics of a light source may include but not limited to one or more light sources, and one or more optical detectors. For instance, a light source (for example, a laser) capable of directly generating polarized light may be used, and a polarizer is arranged on the light source to generate the polarized light. For example, polarizers may be arranged on all the optical detectors or some of the optical detectors, the same polarizers may be arranged on different optical detectors, or different polarizers may be arranged on different optical detectors (for example, linear polarizers of which the polarization directions are perpendicular to each other may be arranged). Polarizers may be arranged on all the light sources or some of the light sources, the same polarizers may be arranged on different light sources, or different polarizers may be arranged on different light sources (for example, the linear polarizers of which the polarization directions are perpendicular to each other may be arranged). The type of a polarizer is not limited to the linear polarizer, and may also include a circular polarizer, an elliptical polarizer, etc.

Figure 13:
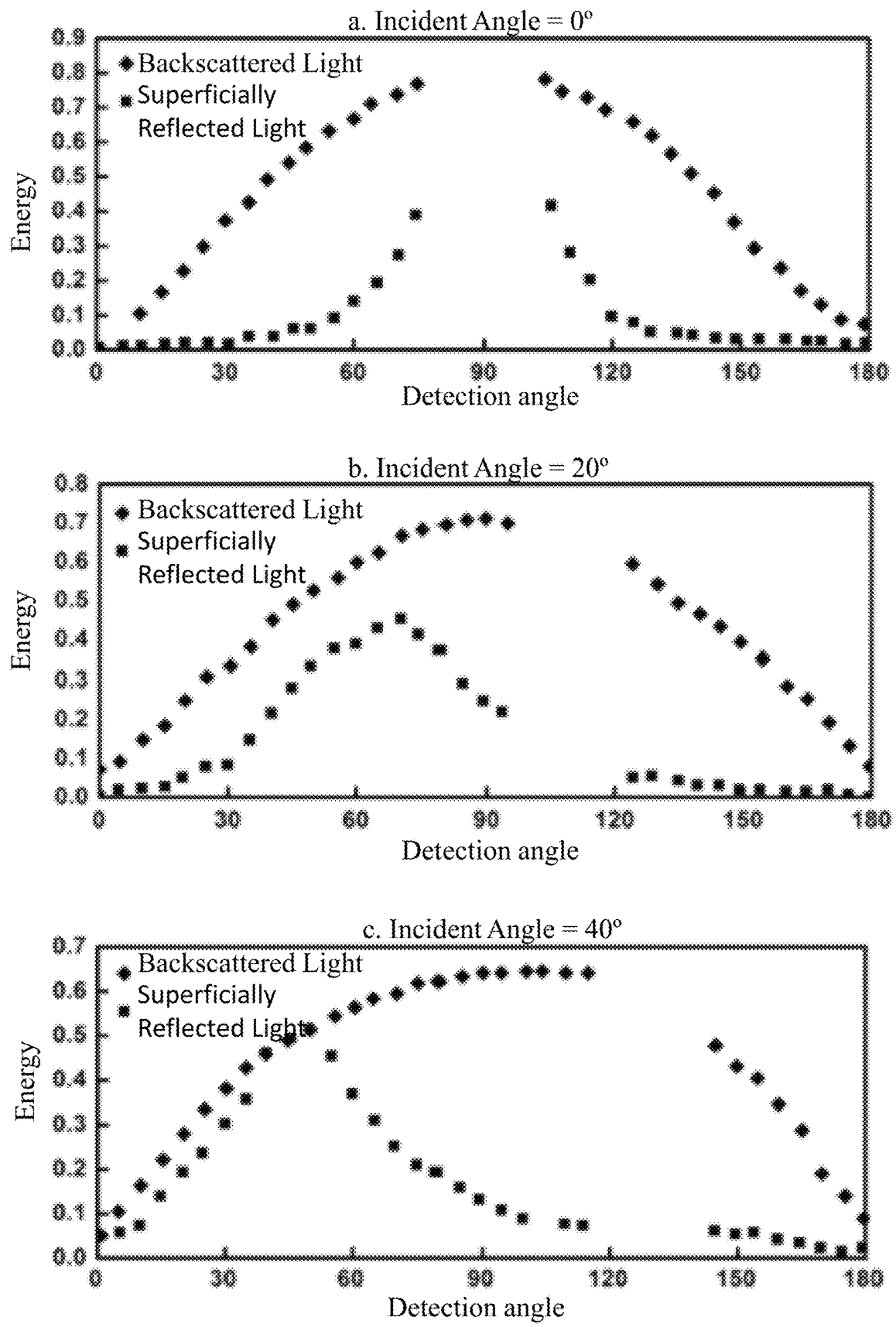
FIG. 13 is a diagram illustrates a relationship between a superficially reflected light, a backscattered light, and a detection angle.
Figure 14:
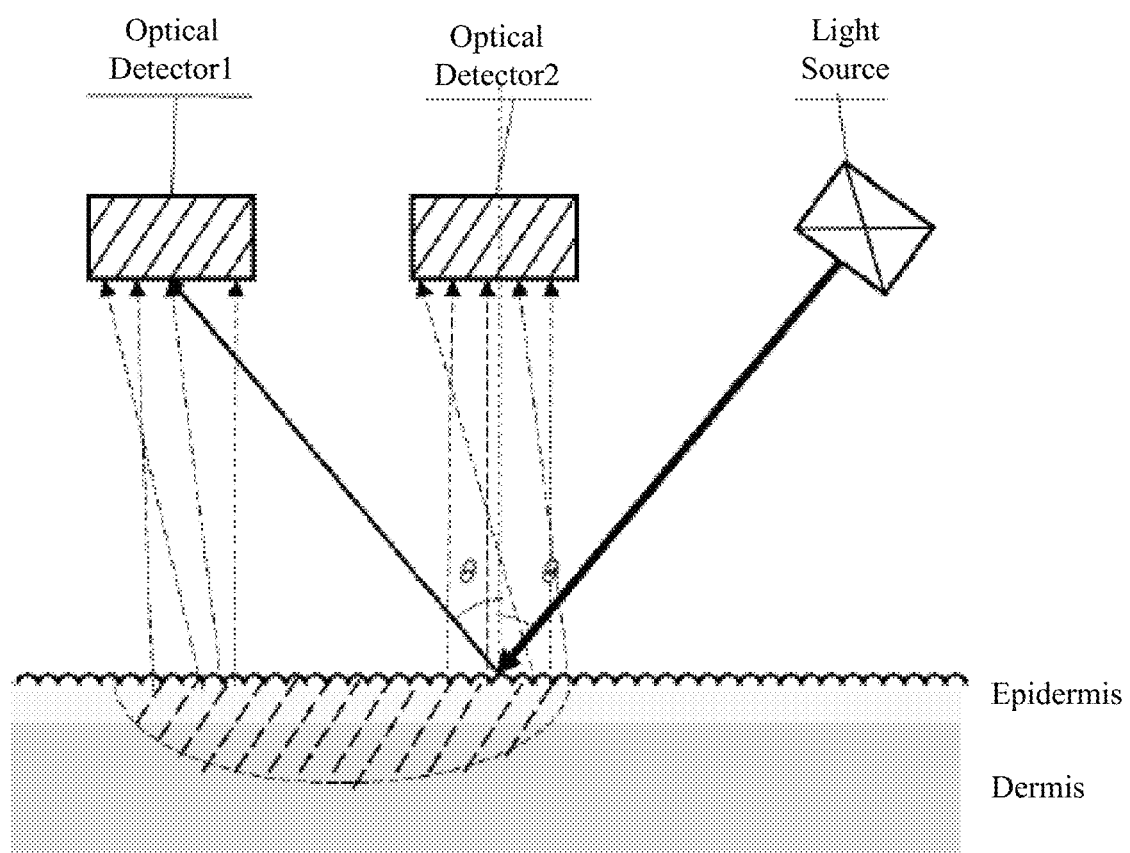
FIGS. 14 to 27 are schematic diagrams of a device of measuring a vital signal of a living body in some embodiments of the present disclosure.

Information of vital signs included in light signals detected by an optical detector is also related to the angle of the light striking the surface of the living body. For example, the reflected light of the skin surface and the backscattered light are related to a detection angle. The light intensity distribution characteristic of the backscattered light is not related to an incident angle, and in a case of the different incident angles, if the detection angle is 90°, the energy of the backscattered light reaches a maximum. The space shape of the light intensity distribution of the superficially reflected light generated due to the different refractive indexes is formed into a spindle shape, the energy of the superficially reflected light reaches the maximum at a theoretical specular reflection area, and detecting energy thereof will decrease as the detection angle further increases (or decreases). FIG. 13 illustrates a diagram illustrating a relationship between the reflected light of the skin surface, the backscattered light, and detection angles. As shown in FIG. 13, if incident angles are different, for example, 0°, 20°, and 40°, the intensity of the backscattered light is substantially the same, if the detection angle is around 90°. FIG. 14 is a schematic diagram of a sensor using a relationship between the reflected light of the skin surface, the backscattered light, and detection angles. The sensor may include two optical detectors and one light source. The light source and the two optical detectors may all be located at a distance from the skin surface, the distance between two optical detectors may be relatively small, and the two optical detectors may also be located with a distance between them. Taken the skin surface as a medium interface, the incident angle of the light emitted by the light source may be θ, the value of θ being in the range of 0° to 90°. The optical detector 1 may be located at the theoretical specular reflection area on a plane determined by the incident light and a normal line, and the angle formed between the normal line and a line connecting the optical detector 1 to an incident point may be θ. The optical detector 2 may be located in vicinity of the normal line of the incident light, that is, a region closer to the normal line of the incident light. Preferably, the angle between the optical detector 2 and the skin interface is in the range of 60° to 120°, and more preferably, the angle between the optical detector 2 and the skin surface is in the range of 80° to 100°. More preferably, the angle between the optical detector 2 and the skin surface is 90°; that is, the optical detector 2 is located just above the normal line of the incident light. When the light source and the optical detector operate, a beam emitted by the light source reaches the skin, a portion of the light is reflected by the skin surface to form the reflected light of the skin surface, and a portion of the light penetrates the epidermis and/or the dermis of the skin to form the backscattered light. The optical detector 1 and the optical detector 2 may each detect the signals during the light source emitting the light, and detect the signals alternately or detect the signals at the same time. The detected signals are the photoelectric signal 1 and the photoelectric signal 2 which are represented as $I_1$ and $I_2$. Since the optical detector 1 is located in the direction of the strongest superficially reflected light, the component of the reflected light of the skin surface in the photoelectric signal 1 detected by the photoelectric detector 1 is larger. Since the optical detector 2 is located in a direction of the strongest backscattered light, the backscattered light component in the photoelectric signal 2 detected by the optical detector 2 is larger. Since the photoelectric signal 1 and the photoelectric signal 2 are represented as $I_1$ and $I_2$, $I_1$ and $I_2$ are taken as the input signals $S_1$ and $S_2$, and motion artifacts may be removed by the method described in connection with FIG. 8 or the similar adaptive noise removal algorithm.

The description above is merely specific embodiments of the present disclosure, and the protection scope of the present disclosure is not limited to the embodiments described above. Those of ordinary skill in the art can make modify and change the present embodiment described above without making creative efforts, and the modifications and changes are in the protection scope of the present disclosure. For example, the positions of the optical detector and the light source may be adjusted, such that part of the optical detectors obtain more reflected light of the skin surface, and part of the optical detectors obtain more backscattered signal, to obtain the input signal including the different components of the vital signal.

Figure 15:
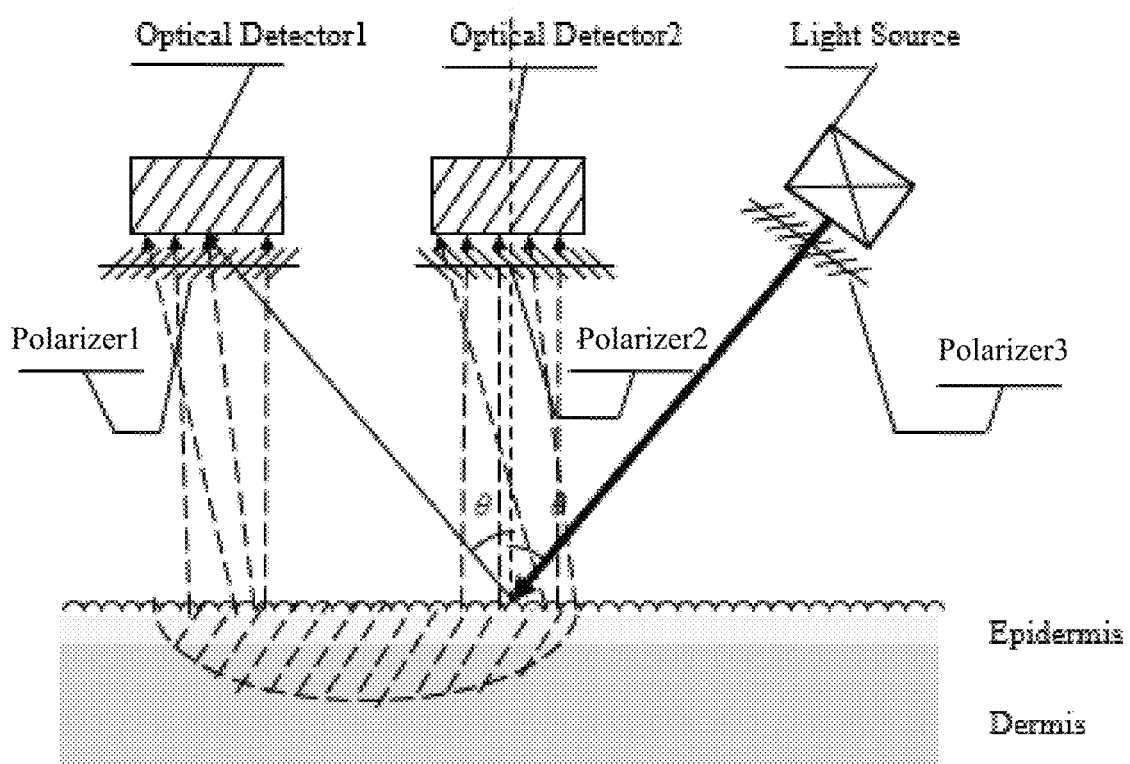

The detecting of a plurality of different signals may be performed by a variation (described above) of the distance between a light source and a detector, polarized characteristics of the light source, relationships between the reflected light of the skin surface and the backscattered light, and detection angles, or a combination thereof. For example, as shown in FIG. 15, the relationships among the polarized characteristics of the light source, the reflected light of the skin surface and the backscattered light, and the detection angles may be used in combination. The sensor may include two optical detectors, one light source, and three polarizers. The two optical detectors and the light source may all be located at a distance from the skin surface, the distance between two optical detectors may be relatively small, and the two optical detectors may also be located with a distance between them. The polarization directions of the polarizer 1 and the polarizer 3 may be the same, or the polarization direction of the polarizer 2 may be perpendicular to the polarization directions of the polarizer 1 and the polarizer 3. Taken the skin surface as the medium interface, the incident angle of the light emitted by the light source may be θ, the value of θ may be in a range of 0° to 90°. The optical detector 1 may be located at the theoretical specular reflection area of a plane determined by the incident light and a normal line, and an angle formed between the normal line and a line connecting the optical detector 1 and an incident point may be θ. The optical detector 2 may be located in vicinity of the normal line of the incident light. Preferably, the angle between the optical detector 2 and the skin interface is 60° to 120°, and more preferably, the angle between the optical detector 2 and the skin surface is in a range of 80° to 100°. More preferably, the angle between the optical detector 2 and the skin surface is 90°; that is, the optical detector 2 is located just above the normal line. When the light source and the two optical detectors operate, after a beam emitted by the light source reaches the skin, a portion of the light is reflected by the skin surface to form the reflected light of the skin surface, and a portion of the light penetrates the epidermis and/or the dermis of the skin to form the backscattered light. The optical detector 1 and the optical detector 2 may each detect the signals if the light source emits the light and may detect the signals alternately or detect the signals at the same time. The detected signals are the photoelectric signal 1 and the photoelectric signal 2 which are represented as $I_1$ and $I_2$. Since the polarization directions of the polarizer 1 and the polarizer 3 may be the same, the parallel component of the reflected light of the skin surface and the parallel component of the backscattered light included in the photoelectric signal 1 detected by the optical detector 1 are the same, and since the optical detector 1 is located on the theoretical specular reflection area on a plane determined by the incident light and the normal line and located in the direction of the strongest reflected light of the skin surface, the component of the reflected light of the skin surface in the photoelectric signal 1 is larger. Since the polarization direction of the polarizer 2 is perpendicular to the polarization direction of the polarizer 3, the photoelectric signal 2 detected by the optical detector 2 may include only the perpendicular component of the backscattered light without including the reflected light of the skin surface, and since the optical detector 2 may be located in vicinity of the normal line of the incident light and be located in the direction of the greater backscattered light, the backscattered light component in the photoelectric signal 2 is larger. The light signal 1 detected by the optical detector 1 includes a large proportion of motion information and a certain proportion of vital signs information, and the light signal 2 detected by the optical detector 2 includes a large proportion of vital signs information and a certain proportion of motion information. Since the light signal 1 and the light signal 2 are taken as the input signals $S_1$ and $S_2$, and motion artifacts may be removed by the method described in connection with FIG. 8 or the similar adaptive noise removal algorithm.

The description above is merely specific embodiments of the present disclosure, and the protection scope of the present disclosure is not limited to the embodiments described above. Those of ordinary skill in the art can make modify and change the present embodiment described above without making creative efforts, and the modifications and changes are in the protection scope of the present disclosure.

The sensor may further include a beam splitter, such that the accuracy of the input signal can be further improved. For example, the beam splitter allows two signals to be taken exactly from the same point on the skin to improve the correlation, and the signal quality is further improved.

Figure 16:
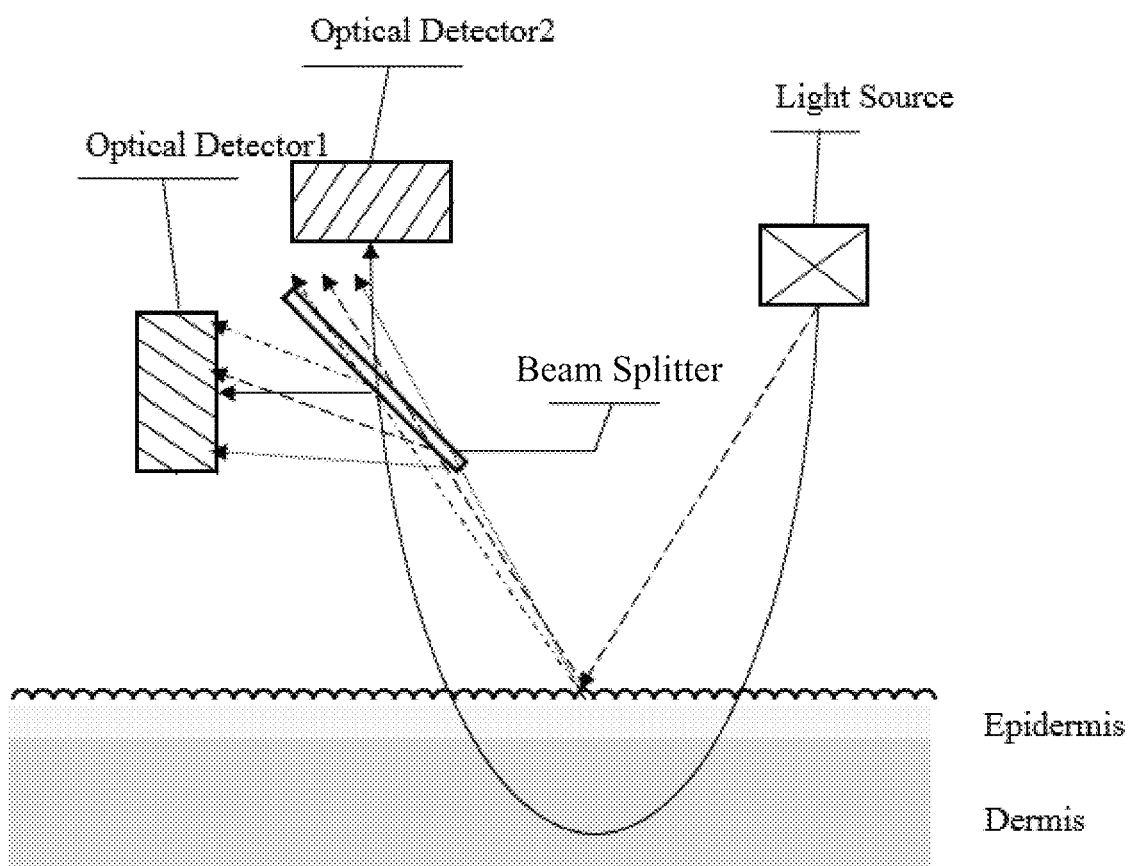

As shown in FIG. 16, the sensor includes one light source capable of generating linearly polarized light, two optical detectors which may detect the light having different polarized characteristics, and one beam splitter. The light source and the optical detectors may all be located at a distance from the skin. The light source only may also be located at a distance from the skin, the optical detectors may be located at a distance from the skin or may be adjacent to the skin surface, and the two optical detectors may be located in the reflection and transmission directions of the beam splitter respectively. The reflected and transmitted light components caused by the beam splitter may be the same. The beam splitter may split the superficially reflected light reflected by the skin into two paths, for example, one is light reflected by the beam splitter and is detected by the optical detector 1, and the other one is light transmitted by the beam splitter and is detected by the optical detector 2. Similarly, the beam splitter may split the multiple backscattered light reflected by the skin into two paths, for example, one is light reflected by the beam splitter and is detected by the optical detector 1, and the other one is light transmitted by the beam splitter and is detected by the optical detector 2. When the sensor operates, each of the optical detector 1 and the optical detector 2 may detect signals during the light source emitting the light, respectively obtaining a photoelectric signal 1 and a photoelectric signal 2. Since the superficially reflected light is still the linearly polarized light and the multiple backscattered light is non-polarized light, the superficially reflected light component and the multiple backscattered light component included in the photoelectric signal 1 and the photoelectric signal 2 have different characteristics. The intensities of the superficially reflected light and the multiple backscattered light may be obtained by determining the characteristics. Motion artifacts may be removed by the method described in connection with FIG. 8 and the adaptive filtering algorithm based on the determined value of the superficially reflected light and the multiple backscattered light.

The examples described above only change and modify some embodiments described in the present disclosure in a single aspect, and the protection scope of the present disclosure is not limited to the alternatives described above. Those of ordinary skill in the art can combine alternatives described above without making creative efforts, and the alternatives are also in the protection scope of the present disclosure. For example, the beam splitter and the polarizer may be replaced with a polarized beam splitter, and the structure thereof can be simplified while retaining the function. As another example, the number of the beam splitters may be larger than one, the light emitted by the light source may be split by the beam splitter, and the light reflected by the skin may also be split by the beam splitter. Alternatively, the light emitted by the light source may be split by part of the beam splitters, and the light reflected by the skin may be split by part of the beam splitter.

Embodiment 1

A vital signal measuring device may be applied to a wearable device, a medical device, sports equipment, etc., may detect various vital signals, may detect and process the signals, may communicate with a terminal, a server, or external data source via a network, and may characterize the signals in various manners. The present embodiment will be described in detail by taking the vital signal measuring device which is mainly used in earphones to detect heart rate as an example.

Figure 17A:
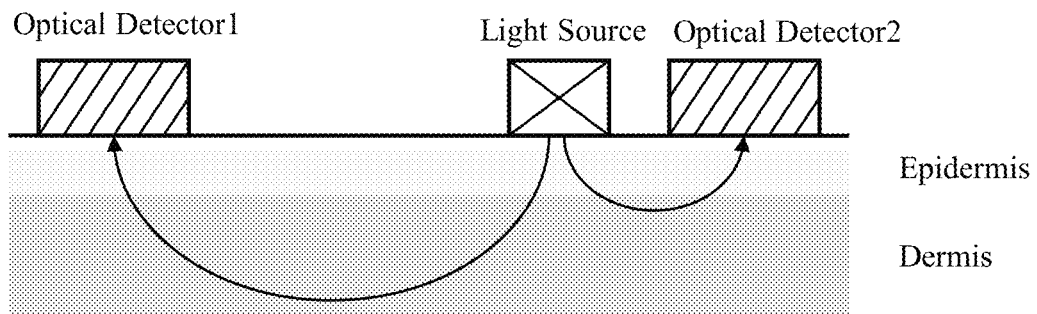

The heart rate measuring device may include but not limited to a detection module, a processing module, a storage module, an output module, a control module, and an energy supply module. The detection module may detect a signal according to a PPG method. If the signal is being detected, the body's motion may interfere with the signal detecting, and thus the detected signal may include some noise. In order to remove the noise due to the movement or vibration signals during a human motion, a multi-parameter adaptive noise removal method may be used, and at least two different signals may be needed for the input. In order to obtain two different signals, a device shown in FIG. 17a may be used. The detection module may include one light source and two optical detectors, each of the two optical detectors and the light source are adjacent to the skin, the three components may be located on a straight line, or may not be located on a straight line, and an optical detector 1 and an optical detector 2 are located on opposite sides of the light source. The distance between the optical detector 1 and the light source is relatively large, and the distance between the optical detector 2 and the light source is relatively small. The distance between the optical detector 1 and the light source is larger than the distance between the optical detector 2 and the light source. If the two optical detectors and the light source operate, the optical detector 1 and the optical detector 2 may detect the reflected signal at the same time if the light source emits the light, respectively obtaining a photoelectric signal 1 and a photoelectric signal 2. Since the distance between the optical detector 1 and the light source is relatively large and photons detected by the optical detector 1 penetrate deeper into the skin, the photoelectric signal 1 may include more pulse wave information. The photoelectric signal 1 and the photoelectric signal 2 are represented as $I_1$ and $I_2$, respectively.

The processing module may take $I_1$ and $I_2$ as two input signals, and motion artifacts are removed by the adaptive noise removal algorithm. The signal without the motion artifacts may be stored in the storage module and may also be output to a terminal, a server, or external data source by the output module. The server may further analyze and process the detected signal according to the relevant historical data in the external data source, to obtain the information of interest and easy-to-understand information, such as heart rate, oxygen consumption, and fat consumption.

The terminal may display the signal in a digital, curved, picture, audio, video manner, etc.

Embodiment 2

Figure 17B:
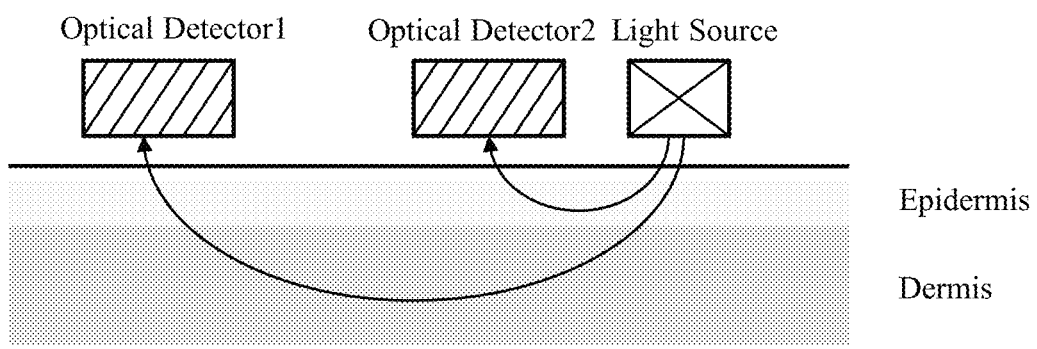

A vital signal detection device may include a detection module different from that described in Embodiment 1. The detection module may have a structure shown in FIG. 17b, and a sensor include two optical detectors and one light source. The two optical detectors and one light source are located at a distance above the skin, the three components may be located on a straight line, or may not be located on a straight line, and an optical detector 1 and an optical detector 2 are located on the same side of the light source. The distance between the optical detector 1 and the light source is relatively large, and the distance between the optical detector 2 and the light source is relatively small. The distance between the optical detector 1 and the light source is larger than the distance between the optical detector 2 and the light source. When the sensor operates, the optical detector 1 and the optical detector 2 may detect the reflected signal at the same time if the light source emits the light, respectively obtaining a photoelectric signal 1 and a photoelectric signal 2. Since the distance between the optical detector 1 and the light source is relatively large and photons detected by the optical detector 1 penetrate deeper into the skin, the photoelectric signal 1 may include more blood volume variation information. The photoelectric signal 1 and the photoelectric signal 2 are represented as $I_1$ and $I_2$, respectively.

The functions, operations, and steps of the processing module, the storage module and the output module thereafter are the same as those in Embodiment 1.

Embodiment 3

Figure 17C:
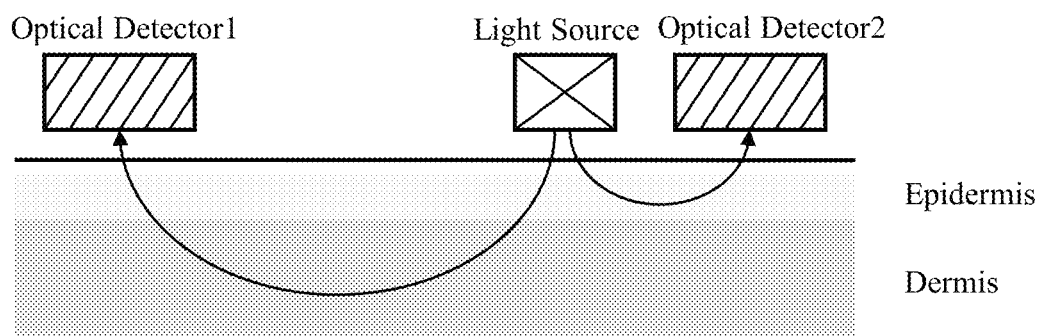

A vital signal detection device may include a detection module different from that described in Embodiment 1. The detection module may have a structure as shown in FIG. 17c, and a sensor may include two optical detectors and one light source. The two optical detectors and one light source are located at a distance above the skin, the three components may be located on a straight line or may not be located on a straight line, and an optical detector 1 and an optical detector 2 are located on opposite sides of the light source. The distance between the optical detector 1 and the light source is relatively large, and the distance between the optical detector 2 and the light source is relatively small. The distance between the optical detector 1 and the light source is larger than the distance between the optical detector 2 and the light source. When the sensor operates, the optical detector 1 and the optical detector 2 may detect reflected signals at the same time when the light source emits the light, respectively obtaining a photoelectric signal 1 and a photoelectric signal 2. Since the distance between the optical detector 1 and the light source is relatively large and photons detected by the optical detector 1 penetrate deeper into the skin, the photoelectric signal 1 may include more blood volume variation information. The photoelectric signal 1 and the photoelectric signal 2 are represented as $I_1$ and $I_2$, respectively.

The functions, operations, and steps of the processing module, the storage module and the output module thereafter are the same as those in Embodiment 1.

Embodiment 4

Figure 17D:
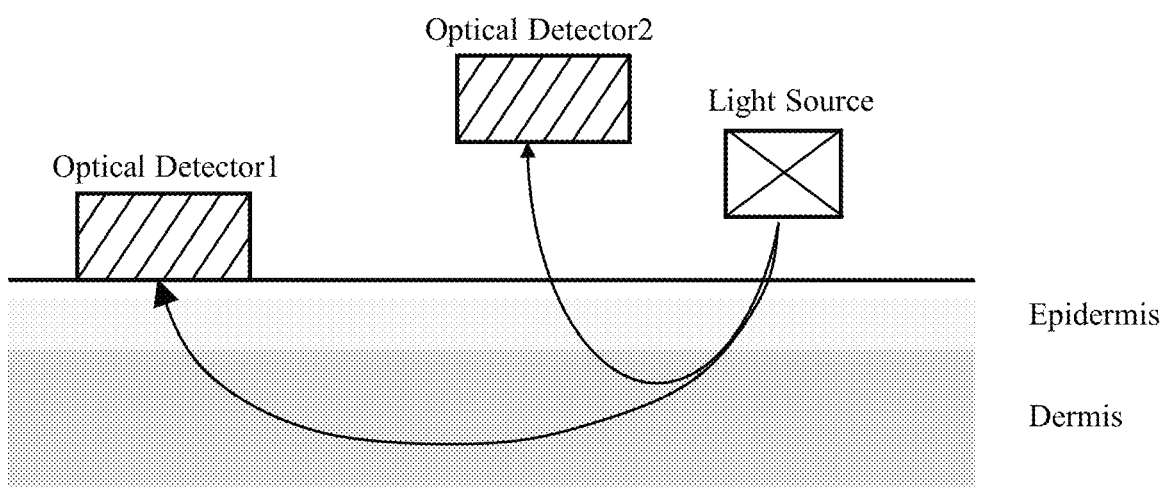

A vital signal detection device may include a detection module different from that described in Embodiment 1. The detection module may have a structure as shown in FIG. 17d, and a sensor may include two optical detectors and one light source. An optical detector 1 is adjacent to the skin, the light source and an optical detector 2 are located at a distance above the skin, and the optical detector 1 and the optical detector 2 are located on the same side of the light source. The horizontal distance between the optical detector 1 and the light source is relatively large, and the horizontal distance between the optical detector 2 and the light source is relatively small. When the two optical detectors and the light source operate, the optical detector 1 and the optical detector 2 may detect the reflected signal at the same time when the light source emits the light, respectively obtaining a photoelectric signal 1 and a photoelectric signal 2. Since the distance between the optical detector 1 and the light source is relatively large and photons detected by the optical detector 1 penetrate deeper into the skin, the photoelectric signal 1 may include more pulse wave information. The photoelectric signal 1 and the photoelectric signal 2 are represented as $I_1$ and $I_2$, respectively.

The functions, operations, and steps of the processing module, the storage module and the output module thereafter are the same as those in Embodiment 1.

Embodiment 5

Figure 18A:
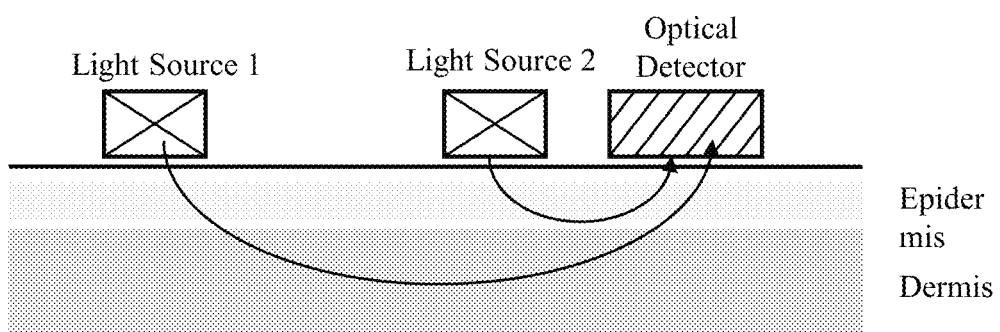

A vital signal detection device may include a detection module different from that described in Embodiment 1. The detection module may have a structure shown in FIG. 18a, a sensor may include one optical detector, and two light sources having the same emission wavelength. The optical detector and the two light sources are each adjacent to the skin, the three components may be located on a straight line, or may not be located on a straight line, and a light source 1 and a light source 2 are located on the same side of the optical detector. The distance between the light source 1 and the optical detector is relatively large, and the distance between light source 2 and the optical detector is relatively small. When the two light sources and the optical detector operate, the light source 1 and the light source 2 emit the light alternately, and the optical detector respectively may detect the reflected signal if the two light sources emit the light, respectively obtaining a photoelectric signal 1 and a photoelectric signal 2. Since the distance between the optical detector and the light source 1 is relatively large and photons emitted by the light source 1 penetrate deeper into the skin, the photoelectric signal 1 may include more pulse wave information. The photoelectric signal 1 and the photoelectric signal 2 are represented as $I_1$ and $I_2$, respectively.

The functions, operations, and steps of the processing module, the storage module and the output module thereafter are the same as those in Embodiment 1.

Embodiment 6

Figure 18B:
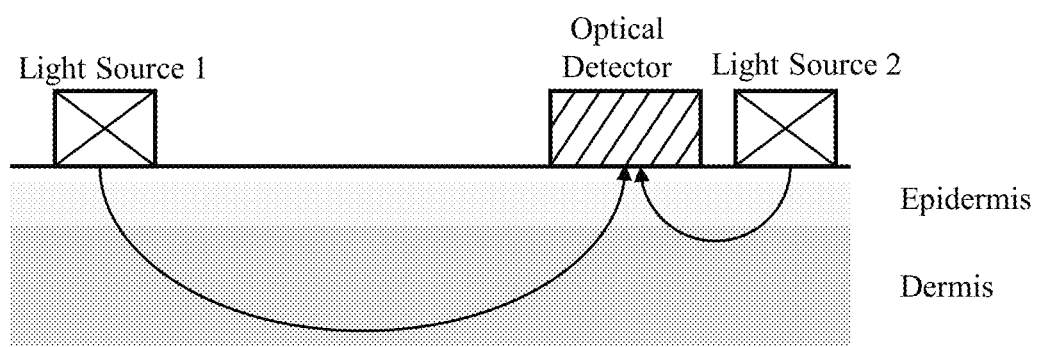

A vital signal detection device may include a detection module different from that described in Embodiment 1. The detection module may have a structure as shown in FIG. 18b, and a sensor may include one optical detector and two light sources having the same emission wavelength. The optical detector and the two light sources are each adjacent to the skin, the three components may be located on a straight line, or may not be located on a straight line, and a light source 1 and a light source 2 are located on opposite sides of the optical detector. The distance between the light source 1 and the optical detector is relatively large, and the distance between light source 2 and the optical detector is relatively small. When the two light sources and the optical detector operate, the light source 1 and the light source 2 emit the light alternately, and the optical detector may detect the reflected signal if the two light sources emit the light, respectively obtaining a photoelectric signal 1 and a photoelectric signal 2. Since the distance between the optical detector and the light source 1 is relatively large and photons emitted by the light source 1 penetrate deeper into the skin, the photoelectric signal 1 may include more pulse wave information. The photoelectric signal 1 and the photoelectric signal 2 are represented as $I_1$ and $I_2$, respectively.

The functions, operations, and steps of the processing module, the storage module and the output module thereafter are the same as those in Embodiment 1.

Embodiment 7

Figure 18C:
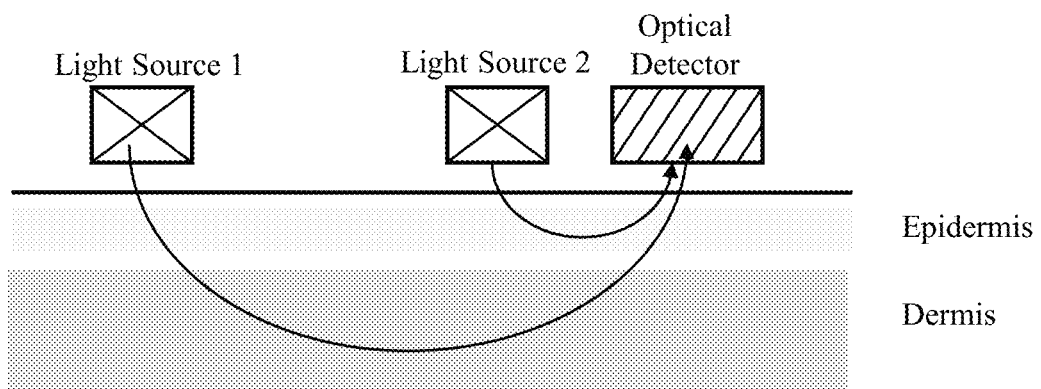

A vital signal detection device may include a detection module different from that described in Embodiment 1. The detection module has a structure as shown in FIG. 18c, and a sensor may include one optical detector and two light sources. The optical detector and the two light sources are each located at a distance above the skin, the three components may be located on a straight line, or may not be located on a straight line, and a light source 1 and a light source 2 are located on the same side of the optical detector. The distance between the light source 1 and the optical detector is relatively large, and the distance between light source 2 and the optical detector is relatively small. When the two light sources and the optical detector operate, the light source 1 and the light source 2 emit the light alternately, and the optical detector may detect the reflected signal when the two light sources emit the light, respectively obtaining a photoelectric signal 1 and a photoelectric signal 2. Since the distance between the optical detector and the light source 1 is relatively large and photons emitted by the light source 1 penetrate deeper into the skin, the photoelectric signal 1 may include more pulse wave information. The photoelectric signal 1 and the photoelectric signal 2 are represented as $I_1$ and $I_2$, respectively.

The functions, operations, and steps of the processing module, the storage module and the output module thereafter are the same as those in Embodiment 1.

Embodiment 8

Figure 18D:
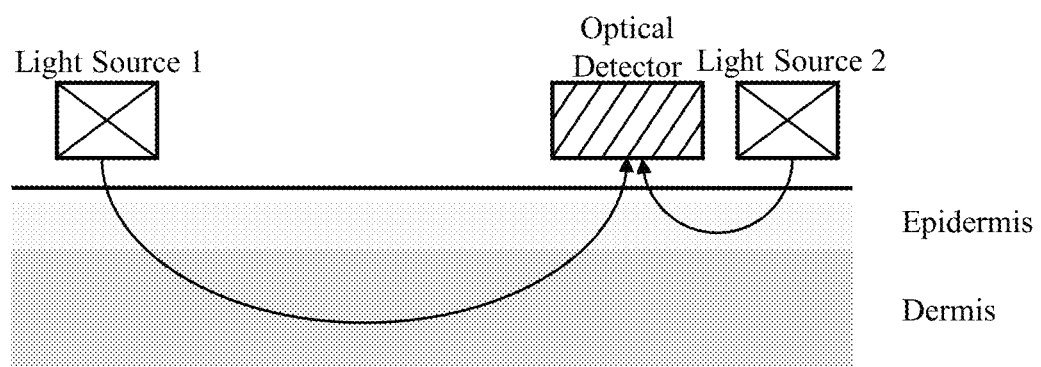

A vital signal detection device may include a detection module different from that described in Embodiment 1. The detection module has a structure as shown in FIG. 18d, and a sensor may include one optical detector and two light sources. The optical detector and the two light sources are each located at a distance above the skin, the three components may be located on a straight line, or may not be located on a straight line, and a light source 1 and a light source 2 are located on opposite sides of the optical detector. The distance between the light source 1 and the optical detector is relatively large, and the distance between light source 2 and the optical detector is relatively small. When the two light sources and the optical detector operate, the light source 1 and the light source 2 emit the light alternately, and the optical detector may detect the reflected signal when the two light sources emit the light, respectively obtaining a photoelectric signal 1 and a photoelectric signal 2. Since the distance between the optical detector and the light source 1 is relatively large and photons emitted by the light source 1 penetrate deeper into the skin, the photoelectric signal 1 may include more pulse wave information. The photoelectric signal 1 and the photoelectric signal 2 are represented as $I_1$ and $I_2$, respectively.

The functions, operations, and steps of the processing module, the storage module and the output module thereafter are the same as those in Embodiment 1.

Embodiment 9

Figure 18E:
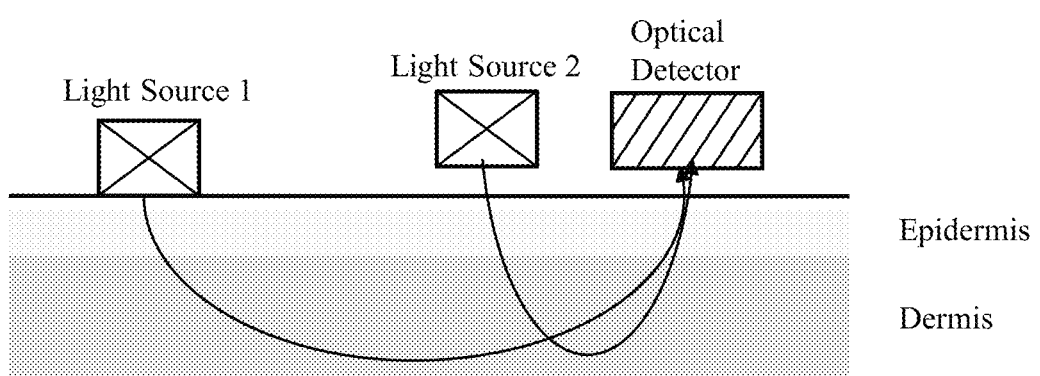

A vital signal detection device may include a detection module different from that described in Embodiment 1. The detection module has a structure as shown in FIG. 18e, and a sensor may include one optical detector and two light sources. A light source 1 is adjacent to the skin, a light source 2 and the optical detector are located at a distance above the skin, and the light source 1 and the light source 2 are located on the same side of the optical detector. The horizontal distance between the light source 1 and the optical detector is relatively large, the horizontal distance between light source 2 and the optical detector is relatively small. When the two light sources and the optical detector operate, the light source 1 and the light source 2 emit the light alternately, and the optical detector may detect the reflected signal when the two light sources emit the light, respectively obtaining a photoelectric signal 1 and a photoelectric signal 2. Since the distance between the optical detector and the light source 1 is relatively large and photons emitted by the light source 1 penetrate deeper into the skin, the photoelectric signal 1 may include more pulse wave information. The photoelectric signal 1 and the photoelectric signal 2 are represented as $I_1$ and $I_2$, respectively.

The functions, operations, and steps of the processing module, the storage module and the output module thereafter are the same as those in Embodiment 1.

Embodiment 10

Figure 19A:
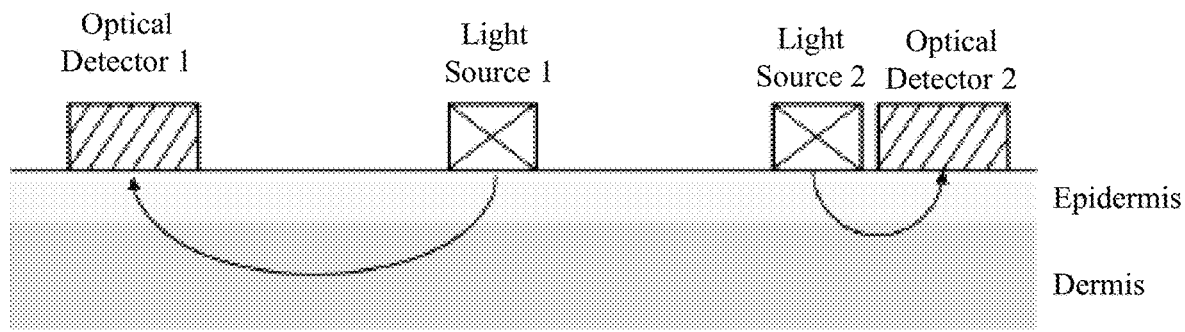

A vital signal detection device may include a detection module different from that described in Embodiment 1. The detection module has a structure as shown in FIG. 19a, a sensor may include two optical detectors and two light sources, and the two optical detectors and the two light sources are each adjacent to the skin. A sensor 1 includes a light source 1 and an optical detector 1, and a sensor 2 includes a light source 2 and an optical detector 2. The distance between the light source 1 and the optical detector 1 is relatively large, and the distance between the light source 2 and the optical detector 2 is relatively small. When the two light sources and the two optical detectors operate, the light source 1 and the light source 2 may emit the light at the same time or may not emit the light at the same time, and the optical detector 1 and the optical detector 2 detect the reflected signal when the light source 1 and the light source 2 emit the light, respectively obtaining a photoelectric signal 1 and a photoelectric signal 2. Since the distance between the optical detector 1 and the light source is relatively large and photons detected by the optical detector 1 penetrate deeper into the skin, the photoelectric signal 1 may include more pulse wave information. The photoelectric signal 1 and the photoelectric signal 2 are represented as $I_1$ and $I_2$, respectively.

The functions, operations, and steps of the processing module, the storage module and the output module thereafter are the same as those in Embodiment 1.

Embodiment 11

Figure 19B:
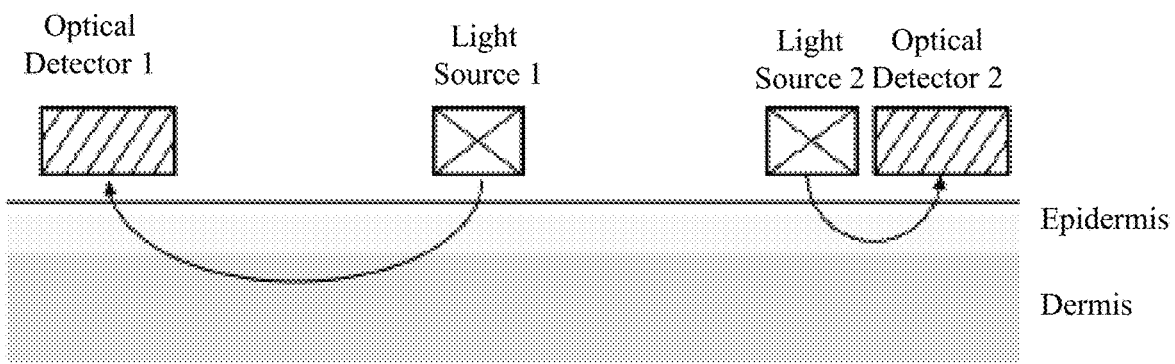

A vital signal detection device may include a detection module different from that described in Embodiment 1. The detection module may have a structure as shown in FIG. 19b, in which a sensor may include two optical detectors and two light sources, the two optical detectors and two light sources being located above the skin by a distance. A sensor 1 includes a light source 1 and an optical detector 1, and a sensor 2 includes a light source 2 and an optical detector 2. The distance between the light source 1 and the optical detector 1 is relatively large, and the distance between the light source 2 and the optical detector 2 is relatively small. When the two optical detectors and two light sources operate, the light source 1 and the light source 2 may emit light at the same time or may not emit light at the same time, and the optical detector 1 and the optical detector 2 may detect reflected signals when the light source 1 and the light source 2 emit light, respectively obtaining a photoelectric signal 1 and a photoelectric signal 2. Since the distance between the optical detector 1 and the light source is relatively large and photons detected by the optical detector 1 penetrate deeper into the skin, the photoelectric signal 1 may include more pulse wave information. The photoelectric signal 1 and photoelectric signal 2 are represented as $I_1$ and $I_2$, respectively.

The functions, operations, and steps of the processing module, the storage module and the output module thereafter are the same as those in Embodiment 1.

Embodiment 12

Figure 20A:
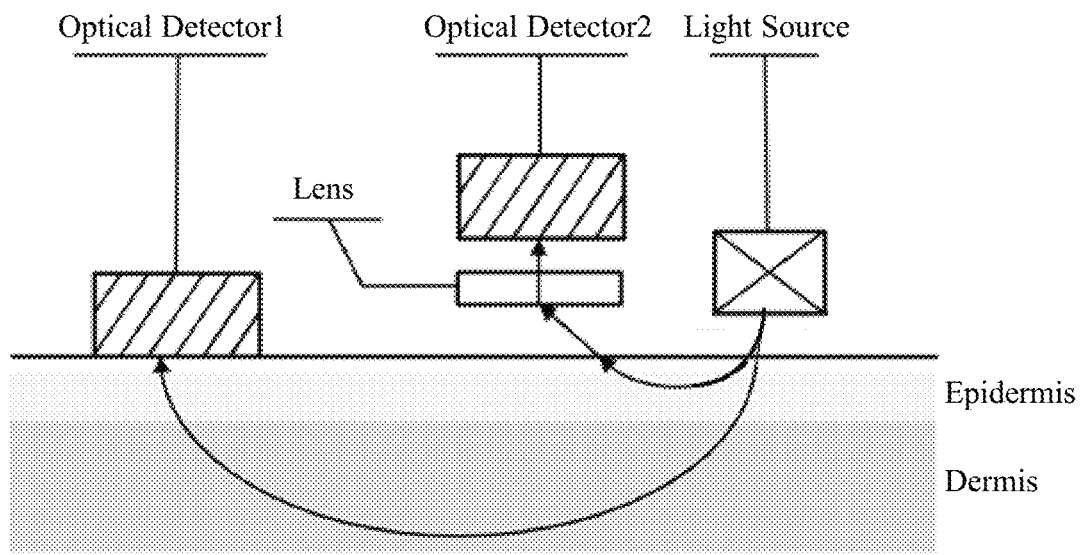

A vital signal detection device may include a detection module different from that described in Embodiment 1. The detection module may have a structure as shown in FIG. 20a, in which a sensor may include two optical detectors, one light source, and one lens. An optical detector 1 may be adjacent to the skin, the light source is located above the skin by a distance, the lens is located between an optical detector 2 and the skin, and the optical detector 1 and the optical detector 2 are located on the same side of the light source. The lens may change a light detecting direction of the optical detector 2 such that the light is at an angle with respect to the skin. The distance between the optical detector 1 and the light source is relatively large, and the distance between the optical detector 2 and the light source is relatively small. When the two optical detectors and the light source operate, the optical detector 1 and the optical detector 2 may detect reflected signals at the same time when the light source emits light, respectively obtaining a photoelectric signal 1 and a photoelectric signal 2. Since the distance between the optical detector 1 and the light source is relatively large and photons detected by the optical detector 1 penetrate deeper into the skin while light detected by the optical detector 2 penetrate shallower into the skin due to the lens, the photoelectric signal 1 may include more pulse wave information. The photoelectric signal 1 and photoelectric signal 2 are represented as $I_1$ and $I_2$, respectively.

The functions, operations, and steps of the processing module, the storage module and the output module thereafter are the same as those in Embodiment 1.

Embodiment 13

Figure 20B:
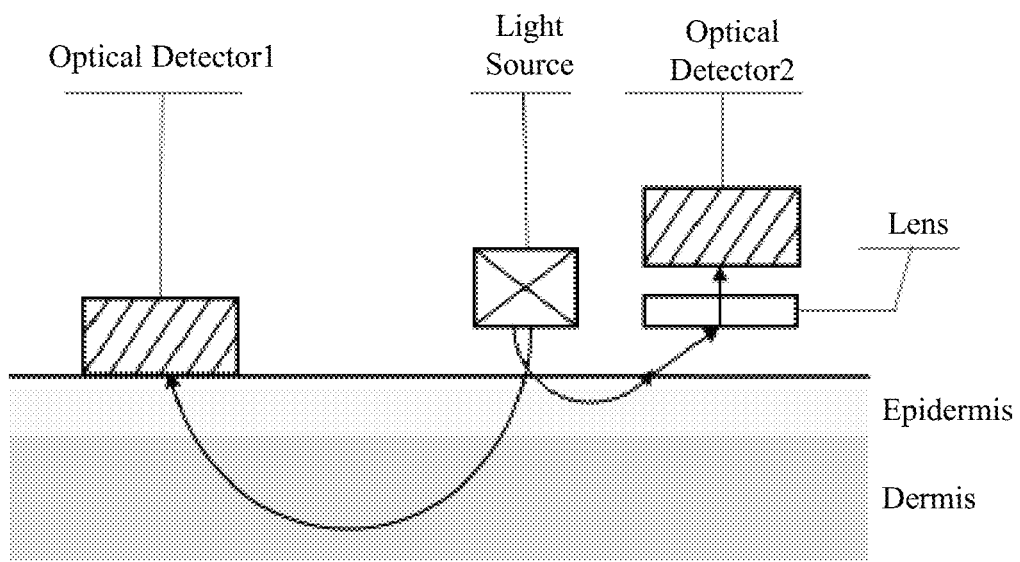

A vital signal detection device may include a detection module different from that described in Embodiment 1. The detection module may have a structure shown in FIG. 20*b*, in which a sensor may include two optical detectors, one light source, and one lens. An optical detector 1 may be adjacent to the skin, the light source is located above the skin by a distance, the lens is located between an optical detector 2 and the skin, and the optical detector 1 and the optical detector 2 are located on opposite sides of the light source. The lens may change the direction of receiving a light by the optical detector 2 such that the light is at an angle with respect to the skin. The distance between the optical detector 1 and the light source is relatively large, and the distance between the optical detector 2 and the light source is relatively small. When the two optical detectors and the light source operate, the optical detector 1 and the optical detector 2 may detect reflected signals at the same time when the light source emits light, respectively obtaining a photoelectric signal 1 and a photoelectric signal 2. Since the distance between the optical detector 1 and the light source is relatively large and photons detected by the optical detector 1 penetrate deeper into the skin while light detected by the optical detector 2 penetrate shallower into the skin due to the lens, the photoelectric signal 1 may include more pulse wave information. The photoelectric signal 1 and photoelectric signal 2 are represented as $I_1$ and $I_2$, respectively.

The functions, operations, and steps of the processing module, the storage module and the output module thereafter are the same as those in Embodiment 1.

Embodiment 14

Figure 20C:
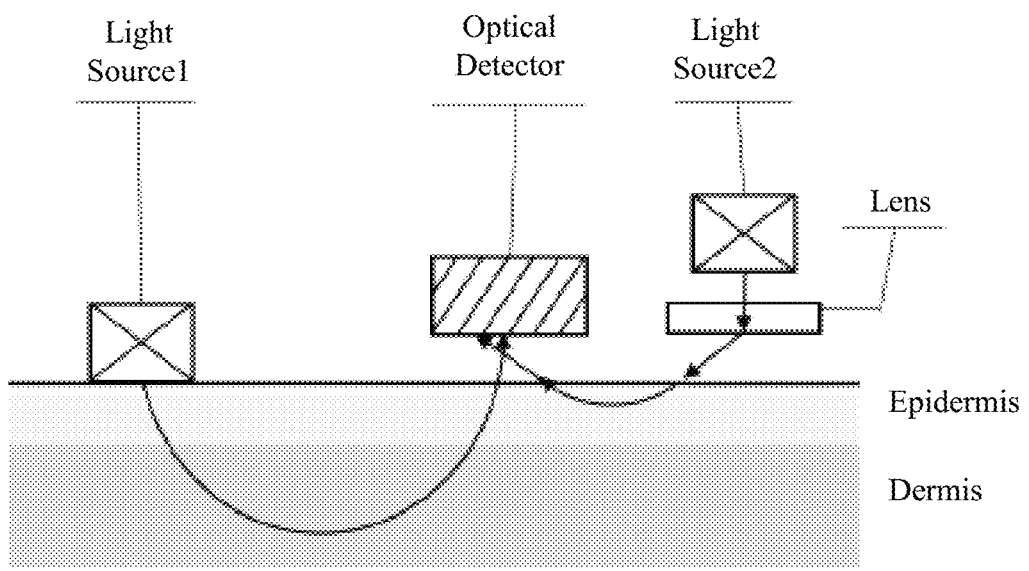

A vital signal detection device may include a detection module different from that described in Embodiment 1. The detection module may have a structure shown in FIG. 20*c*, in which a sensor may include one optical detector, two light sources, and one lens. A light source 1 may be adjacent to the skin, the optical detector is located above the skin by a distance, the lens is located between a light source 2 and the skin, and the light source 1 and the light source 2 are located on opposite sides of the optical detector. The lens may change a light emitting direction of the light source 2 such that the light is at an angle with respect to the skin. The distance between the light source 1 and the optical detector is relatively large, and the distance between the light source 2 and the optical detector is relatively small. When the two light sources and the optical detector operate, the light source 1 and the light source 2 may emit light alternately, and the optical detector may detect reflected signals respectively when a light source emits light, respectively obtaining a photoelectric signal 1 and a photoelectric signal 2. Since the distance between the light source 1 and the optical detector is relatively large and photons emitted by the light source 1 penetrate deeper into the skin while light emitted by the light source 2 penetrate shallower into the skin due to the lens, the photoelectric signal 1 may include more pulse wave information. The photoelectric signal 1 and photoelectric signal 2 are represented as $I_1$ and $I_2$, respectively.

The functions, operations, and steps of the processing module, the storage module and the output module thereafter are the same as those in Embodiment 1.

Embodiment 15

Figure 21A:
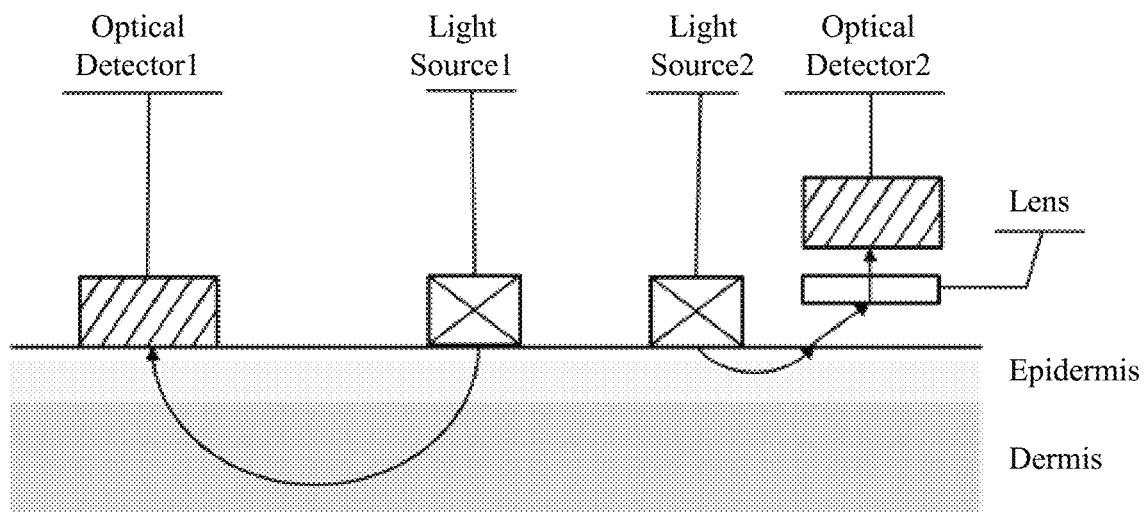

A vital signal detection device may include a detection module different from that described in Embodiment 1. The detection module may have a structure as shown in FIG. 21*a*, in which a sensor may include two light sources, two optical detectors, and one lens. A sensor 1 includes a light source 1 and an optical detector 1, and a sensor 2 includes a light source 2 and an optical detector 2. The optical detector 1 and the light source 1 may be adjacent to the skin, the light source 2 is located above the skin by a distance, the lens is located between the optical detector 2 and the skin, and the light source 1 and the light source 2 are located between the two detectors. The lens may change a light detecting direction of the optical detector 2 such that the light is at an angle with respect to the skin. The distance between the optical detector 1 and the light source 1 is relatively large, and the distance between the optical detector 2 and the light source 2 is relatively small. When the two optical detectors and the tow light sources operate, the light source 1 and the light source 2 may emit light at the same time or may not emit light at the same time, and the optical detector 1 and the optical detector 2 may detect reflected signals when the light source 1 and the light source 2 emit light, respectively obtaining a photoelectric signal 1 and a photoelectric signal 2. Since the distance between the optical detector 1 and the light source 1 is relatively large and photons detected by the optical detector 1 penetrate deeper into the skin while light detected by the optical detector 2 penetrate shallower into the skin due to the lens, the photoelectric signal 1 may include more pulse wave information. The photoelectric signal 1 and photoelectric signal 2 are represented as $I_1$ and $I_2$, respectively.

The functions, operations, and steps of the processing module, the storage module and the output module thereafter are the same as those in Embodiment 1.

Embodiment 16

Figure 21B:
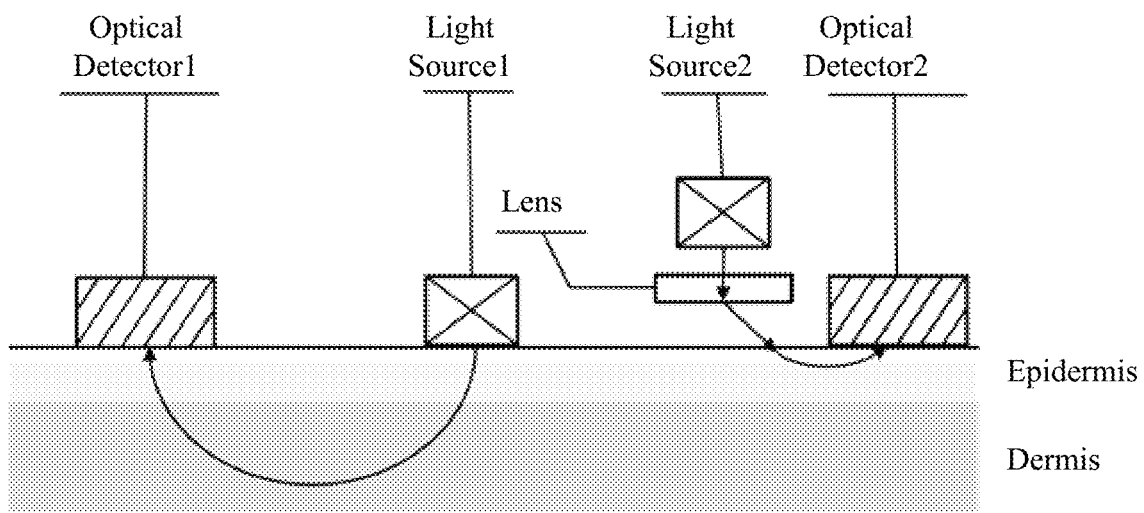

A vital signal detection device may include a detection module different from that described in Embodiment 1. The detection module may have a structure as shown in FIG. 21*b*, in which a sensor may include two light sources, two optical detectors, and one lens. A sensor 1 includes a light source 1 and an optical detector 1, and a sensor 2 includes a light source 2 and an optical detector 2. The optical detector 1 and the light source 1 may be adjacent to the skin, the optical detector 2 is located above the skin by a distance, the lens is located between the light source 2 and the skin, and the light source 1 and the light source 2 are located between the two detectors. The lens may change a light emitting direction of the light source 2 such that the light is at an angle with respect to the skin. The distance between the optical detector 1 and the light source 1 is relatively large, and the distance between the optical detector 2 and the light source 2 is relatively small. When the two optical detectors and the two light sources operate, working conditions of the light sources and the optical detectors are the same as those in the fifteenth embodiment.

The functions, operations, and steps of the processing module, the storage module and the output module thereafter are the same as those in Embodiment 1.

Embodiment 17

Figure 21C:
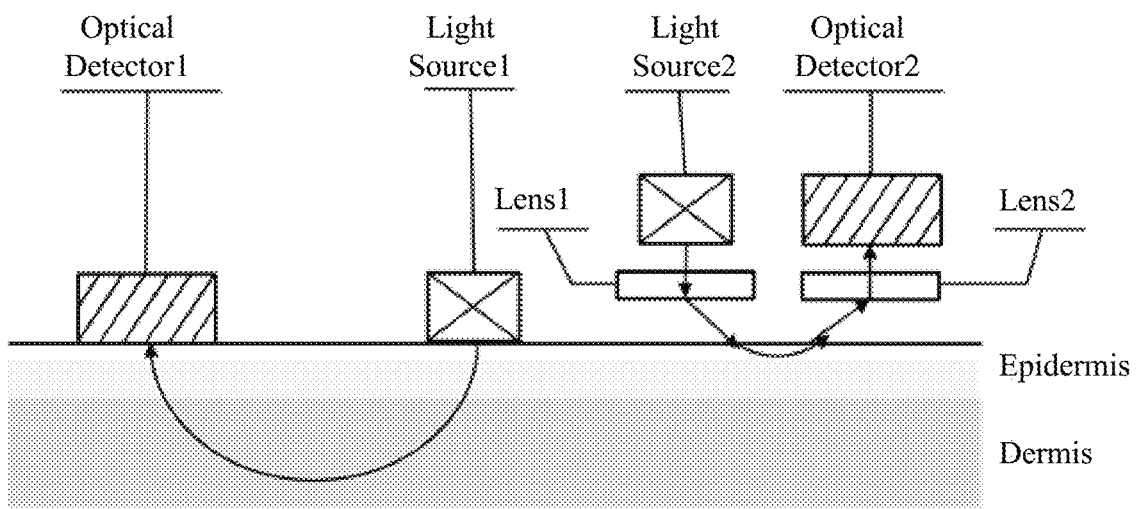

A vital signal detection device may include a detection module different from that described in Embodiment 1. The detection module may have a structure as shown in FIG. 21c, in which a sensor may include two light sources, two optical detectors, and two lenses. A sensor 1 includes a light source 1 and an optical detector 1, and a sensor 2 includes a light source 2 and an optical detector 2. The optical detector 1 and the light source 1 may be adjacent to the skin, a lens 1 is located between the light source 2 and the skin, a lens 2 is located between the optical detector 2 and the skin, and the light source 1 and the light source 2 are located between the two detectors. The lens 1 may change a light emitting direction of the light source 2 and the lens 2 may change a direction of a reflected signal detected by the optical detector 2 such that the light is at an angle with respect to the skin. the distance between the optical detector 1 and the light source 1 is relatively large, and the distance between the optical detector 2 and the light source 2 is relatively small. When the two optical detectors and the two light sources operate, working conditions of the light sources and the optical detectors are the same as those in the fifteenth embodiment.

The functions, operations, and steps of the processing module, the storage module and the output module thereafter are the same as those in Embodiment 1.

Embodiment 18

Figure 22A:
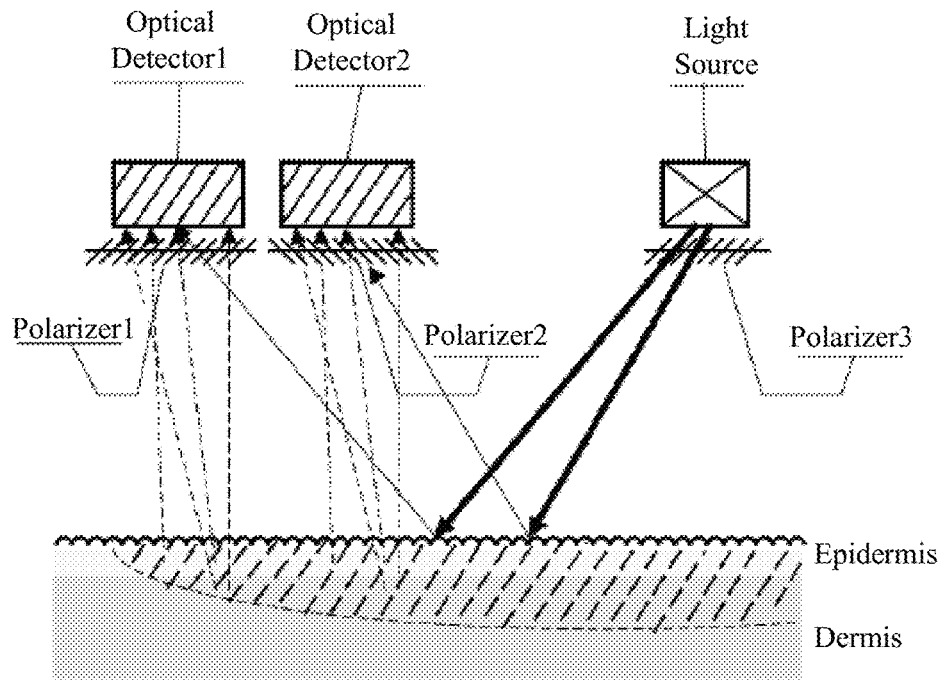

A vital signal detection device may include a detection module different from that described in Embodiment 1. The detection module may have a structure as shown in FIG. 22a, in which a sensor may include one light source, two optical detectors, and three polarizers. The polarizer here is also referred to as a polarized plate or a polarized film, and is an optical element that can change a normal beam into a polarized beam. For those of ordinary skill in the art, the polarizer may not be needed if the beam itself has polarized characteristics. For example, a beam emitted by a laser already has polarized characteristics, so a polarizer may not be needed. A polarizer and a component having a certain optical rotation may also be used to adjust polarized characteristics of a light source, and the use of the polarizer or the component having the optical rotation is still within the protection scope described above. The light source and the optical detectors are at a distance from the skin, and the distance between the two detectors may be very short. Polarization directions of a polarizer 1 and a polarizer 3 are substantially the same and are perpendicular to a polarization direction of a polarizer 2. When the sensor operates, an optical detector 1 and an optical detector 2 may detect reflected signals when the light source emits light, respectively obtaining a photoelectric signal 1 and a photoelectric signal 2. Since the polarization directions of the polarizer 1 and the polarizer 3 are the same, the photoelectric signal 1 detected by the photodetector 1 may include a parallel component of superficially reflected light and a parallel component of multiple backscattered light. Since the polarization direction of the polarizer 2 is perpendicular to the polarization direction of the polarizer 3, a photoelectric signal 2 detected by the photodetector 2 may not include the superficially reflected light, but include a perpendicular component of the multiple backscattered light. When the photoelectric signal 1 is represented as $I_1$, the photoelectric signal 2 is represented as $I_2$, the superficially reflected light is represented as $I_R$, the multiple backscattered light is represented as $I_B$, and subscripts $\|$ and $\perp$ represent a parallel component and a perpendicular component respectively, $$I_1 = I_{1R\|} + I_{1B\|},$$

$$I_2 = I_{2B\perp};$$

the superficially reflected light only has a parallel component, therefore $$I_R = I_{1R\|};$$

a skin multiple backscattered light before passing through the polarizer 2 is defined as $I_B$, and the backscattered light has no polarized characteristics, therefore $$I_B = 2I_{2B\perp}.$$

Since the optical detector 1 and the optical detector 2 are at different positions, the intensity of multiple backscattered light reaching the polarizer 1 and the intensity of multiple backscattered light reaching the polarizer 2 are slightly different. When, $$I_{1B\|} = I_{2B\perp} + \Delta_B,$$

the superficially reflected light and the multiple backscattered light can be calculated by the following two equations separately:

$$I_R = I_1 - I_2 - \Delta_B \text{ and}$$

$$I_B = 2I_2.$$

When $$I_s = 2I_2 \text{ and}$$

$$I_r = I_1 - I_2,$$

the $I_s$ may only include the multiple backscattered light, and the $I_r$ may include the superficially reflected light and a very small amount of multiple backscattered light. The $I_s$ may include a motion disturbance signal and a heartbeat signal, and the $I_r$ may basically include only a motion disturbance signal. The $I_s$ and $I_r$ are used as input signals $S_1$ and $S_2$ separately, and motion artifacts are removed by the adaptive noise removal algorithm in FIG. 8 or a similar algorithm.

Embodiment 19

Figure 22B:
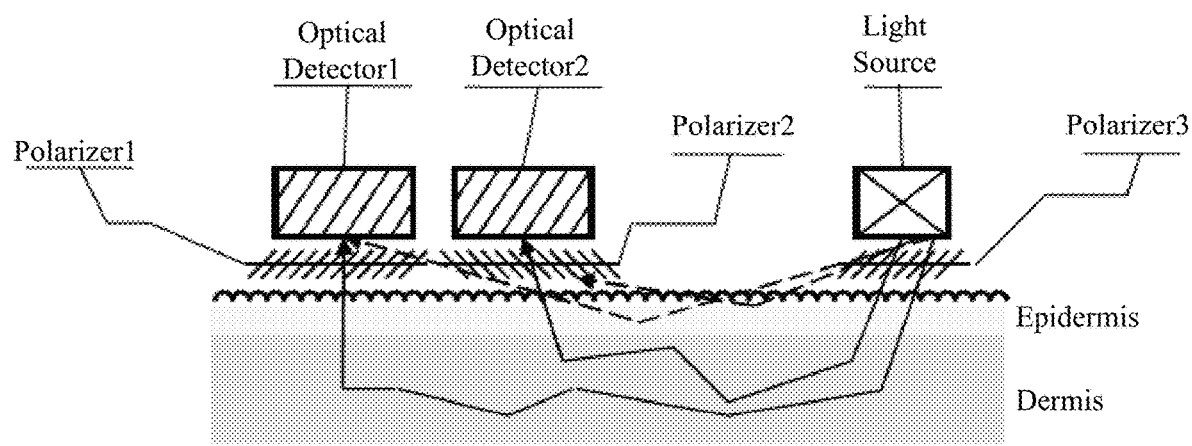

A vital signal detection device may include a detection module different from that described in Embodiment 1. The detection module may have a structure as shown in FIG. 22b, in which a sensor may include one light source, two optical detectors, and three polarizers. The polarizer described in the present specification may also be a polarized plate or a polarized film, and is an optical element that can change a normal beam into a polarized beam. For those of ordinary skill in the art, the polarizer may not be needed if the beam itself has polarized characteristics. For example, a beam emitted by a laser already has polarized characteristics, so a polarizer may not be needed. A polarizer and a component having a certain optical rotation may also be used to adjust polarized characteristics of a light source, and the use of the polarizer or the component having the optical rotation is still within the protection scope described above. The light source and the optical detectors may be adjacent to the skin surface, and the distance between the two detectors is relatively small. Polarization directions of a polarizer 1 and a polarizer 3 are substantially the same and are perpendicular to a polarization direction of a polarizer 2. When the sensor operates, an optical detector 1 and an optical detector 2 may detect reflected signals when the light source emits light, respectively obtaining a photoelectric signal 1 and a photoelectric signal 2. Since the polarization directions of the polarizer 1 and the polarizer 3 are the same, the photoelectric signal 1 detected by the photodetector 1 may include a parallel component of less backscattered light and a parallel component of multiple backscattered light. Since the polarization direction of the polarizer 2 is perpendicular to the polarization direction of the polarizer 3, a photoelectric signal 2 detected by the photodetector 2 may not include the less backscattered light, but only include a perpendicular component of the multiple backscattered light. When the photoelectric signal 1 is represented as $I_1$, the photoelectric signal 2 is represented as $I_2$, the less backscattered light is represented as $I_{BR}$, the multiple backscattered light is represented as $I_B$, and subscripts $\parallel$ and $\perp$ represent a parallel component and a perpendicular component respectively, $$I_1 = I_{1BR} + I_{1B},$$

$$I_2 = I_{2B\perp};$$

only the photoelectric signal 1 may include the less backscattered light, therefore $$I_{BR} = I_{1BR};$$

a multiple backscattered light passing through the polarizer 2 is defined as $I_B$, and the backscattered light has no polarized characteristics, therefore $$I_B = 2I_{2B\perp}.$$

Since the optical detector 1 and the optical detector 2 are at different positions, the intensity of backscattered light reaching the polarizer 1 and the intensity of backscattered light reaching the polarizer 2 are slightly different. When $$I_{1B} = 2I_{2B\perp} + \Delta_B,$$

the less backscattered light and the multiple backscattered light can be calculated by the following two equations separately:

$$I_{BR} = I_1 - 2I_2 - \Delta_B \text{ and}$$

$$I_B = 2I_2.$$

When $$I_s = 2I_2 \text{ and}$$

$$I_r = I_1 - 2I_2,$$

the $I_s$ may only include the multiple backscattered light, and $I_r$ may include the less backscattered light and a very small amount of multiple backscattered light. The $I_s$ may include a motion disturbance signal and a heartbeat signal, and the $I_r$ may basically include only a motion disturbance signal.

The processing module may use the $I_s$ and $I_r$ as input signals, and remove motion artifacts by the adaptive noise removal algorithm. The functions, operations, and steps of the storage module and the output module thereafter are the same as those in Embodiment 1.

Embodiment 20

Figure 22C:
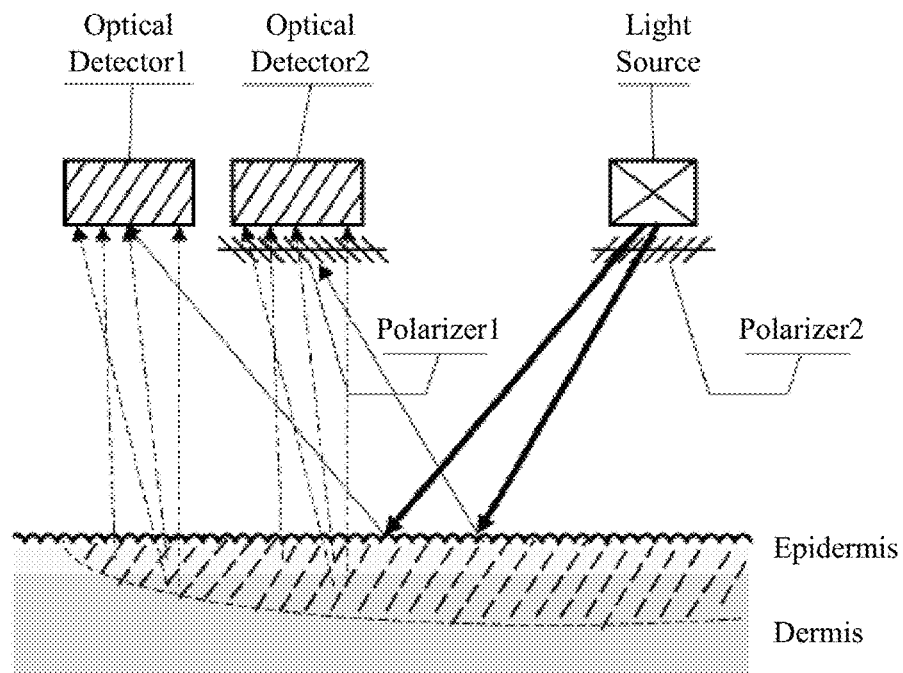

A vital signal detection device may include a detection module different from that described in Embodiment 1. The detection module may have a structure as shown in FIG. 22c, in which a sensor may include one light source, two optical detectors, and two polarizers. A polarizer 2 is used to generate a polarized light with a normal light source. If a laser is used as the light source (such as a laser diode), the laser already has polarized characteristics, in which case the polarizer 2 may not be needed. The light source and the optical detectors are at a distance from the skin, and the distance between the two detectors may be very short. A polarization direction of a polarizer 1 is perpendicular to a polarization direction of the polarizer 2. When the sensor operates, an optical detector 1 and an optical detector 2 may detect reflected signals when the light source emits light, respectively obtaining a photoelectric signal 1 and a photoelectric signal 2. Since there is no polarizer below the optical detector 1, the photoelectric signal 1 detected by the photodetector 1 may include superficially reflected light and multiple backscattered light. Since the polarization direction of the polarizer 1 is perpendicular to the polarization direction of the polarizer 2, a photoelectric signal 2 detected by the sensor 2 may not include the superficially reflected light, but only include a perpendicular component of the multiple backscattered light. When the photoelectric signal 1 is represented as $I_1$, the photoelectric signal 2 is represented as $I_2$, the superficially reflected light is represented as $I_R$, the multiple backscattered light is represented as $I_B$, and subscripts $\parallel$ and $\perp$ represent a parallel component and a perpendicular component respectively, $$I_1 = I_{1R} + I_{1B},$$

$$I_2 = I_{2B\perp};$$

only the photoelectric signal 1 may include the superficially reflected light, therefore $$I_R = I_{1R};$$

a skin multiple backscattered light before passing through the polarizer 2 is defined as $I_B$, and the multiple backscattered light has no polarized characteristics, therefore $$I_B = 2I_{2B\perp}.$$

Since the optical detector 1 and the optical detector 2 are at different positions, the intensity of multiple backscattered light reaching the polarizer 1 and the intensity of multiple backscattered light reaching the polarizer 2 are slightly different. When $$I_{1B} = 2I_{2B\perp} + \Delta_B,$$

the superficially reflected light and the multiple backscattered light can be calculated by the following two equations separately:

$$I_R = I_1 - 2I_2 - \Delta_B \text{ and}$$

$$I_B = 2I_2.$$

When $$I_s = 2I_2 \text{ and}$$

$$I_r = I_1 - 2I_2,$$

the $I_s$ may only include the multiple backscattered light, and $I_r$ may include the superficially reflected light and a very small amount of multiple backscattered light. The $I_s$ may include a motion disturbance signal and a heartbeat signal, and the $I_r$ may basically include only a motion disturbance signal.

The processing module may use the $I_s$ and $I_r$ as input signals, and remove motion artifacts by the adaptive noise removal algorithm. The functions, operations, and steps of the storage module and the output module thereafter are the same as those in Embodiment 1.

Embodiment 21

Figure 22D:
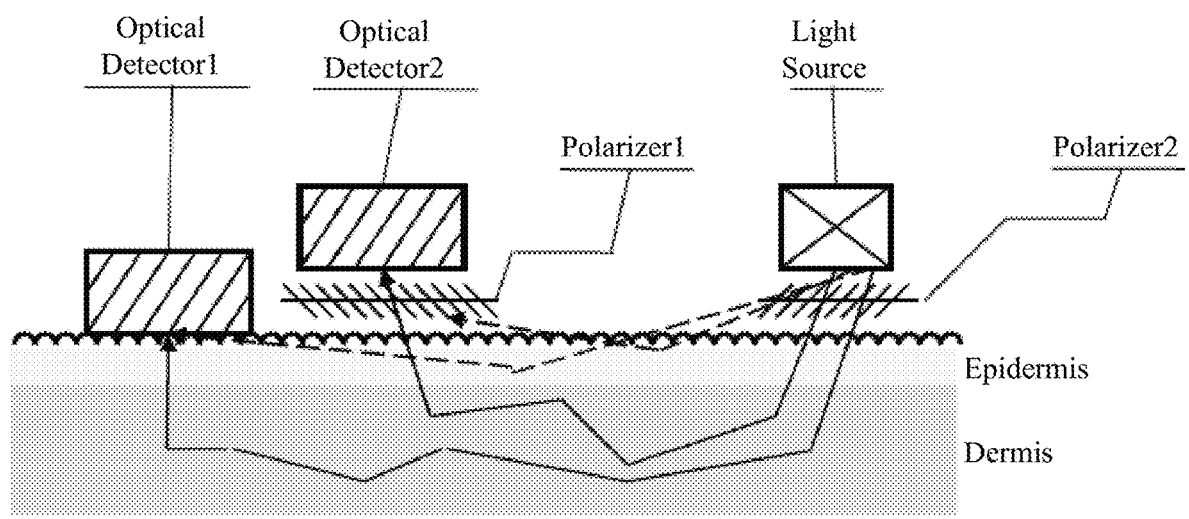

A vital signal detection device may include a detection module different from that described in Embodiment 1. The detection module may have a structure as shown in FIG. 22d, in which a sensor may include one light source, two optical detectors, and two polarizers (i.e., polarizer 1 and polarizer 2). A polarizer 2 is used to generate a polarized light with a normal light source. If a laser is used as the light source (such as a laser diode), the laser already has polarized characteristics, in which case the polarizer 2 may not be needed. The light source may be adjacent to the skin surface, the two optical detectors may be adjacent to the skin surface or may be at a distance from the skin, and the distance between the two detectors may be very short. A polarization direction of a polarizer 1 is perpendicular to a polarization direction of the polarizer 2. When the sensor operates, an optical detector 1 and an optical detector 2 may detect reflected signals when the light source emits light, respectively obtaining a photoelectric signal 1 and a photoelectric signal 2. Since there is no polarizer below the optical detector 1, the photoelectric signal 1 detected by the photodetector 1 may include less backscattered light and multiple backscattered light. Further, since the polarization direction of the polarizer 1 is perpendicular to the polarization direction of the polarizer 2, a photoelectric signal 2 detected by the sensor 2 may not include the less backscattered light, but only include a perpendicular component of the multiple backscattered light. When the photoelectric signal 1 is represented as $I_1$, the photoelectric signal 2 is represented as $I_2$, the less backscattered light is represented as $I_{BR}$, the multiple backscattered light is represented as $I_B$, and subscripts $\parallel$ and $\perp$ represent a parallel component and a perpendicular component respectively, $I_1 = I_{1BR} + I_{1B}$, $I_2 = I_{2B\perp}$;

only the photoelectric signal 1 may include the superficially reflected light, therefore $I_{BR} = I_{1BR}$;

a skin multiple backscattered light before passing through the polarizer 2 is defined as $I_B$, and the multiple backscattered light has no polarized characteristics, therefore $I_B = 2I_{2B\perp}$.

Since the optical detector 1 and the optical detector 2 are at different positions, the intensity of multiple backscattered light reaching the polarizer 1 and the intensity of multiple backscattered light reaching the polarizer 2 are slightly different. When $I_{1B} = 2I_{2B\perp} + \Delta_B$, the less backscattered light and the multiple backscattered light can be calculated by the following two equations separately:

$I_{BR} = I_1 - 2I_2 - \Delta_B$ and $I_B = 2I_2$.

When $I_s = 2I_2$ and $I_r = I_1 - 2I_2$, the $I_s$ may only include the multiple backscattered light, and $I_r$ may include the less backscattered light and a very small amount of multiple backscattered light. The $I_s$ may include a motion disturbance signal and a heartbeat signal, and the $I_r$ may basically include only a motion disturbance signal.

The processing module may use the $I_s$ and $I_r$ as input signals, and remove motion artifacts by the adaptive noise removal algorithm. The functions, operations, and steps of the storage module and the output module thereafter are the same as those in Embodiment 1.

Embodiment 22

Figure 22E:
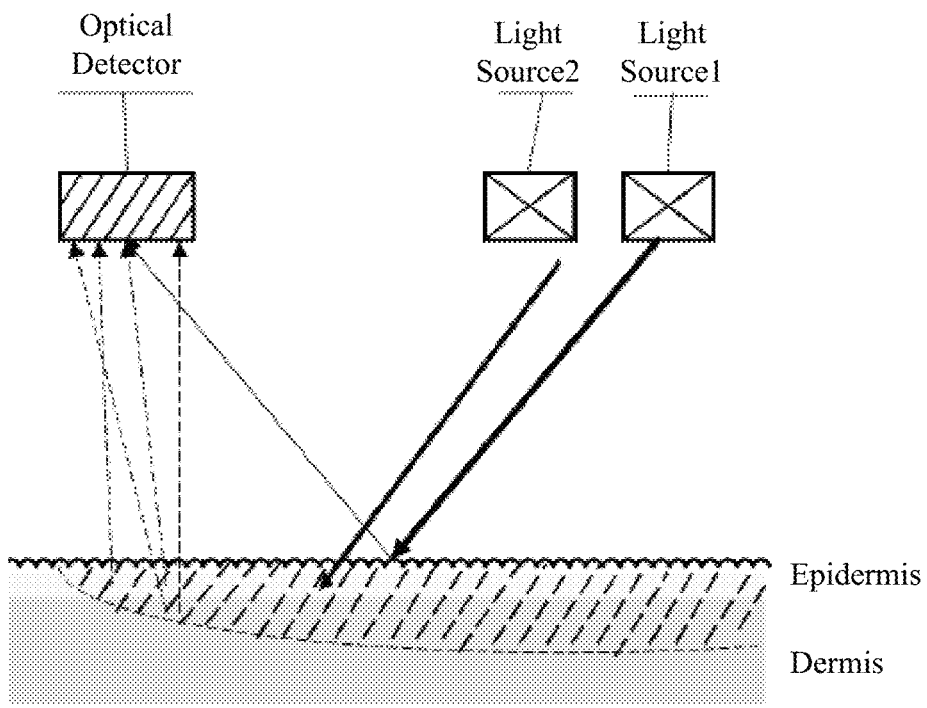

A vital signal detection device may include a detection module different from that described in Embodiment 1. The detection module may have a structure as shown in FIG. 22e, in which a sensor may include two light sources that can generate linearly polarized light and one optical detector that can detect light with different polarized characteristics. The light sources and the optical detector are at a distance from the skin, and the distance between the two detectors may be very short. When the sensor operates, a light source 1 and a light source 2 may emit light alternately, and the optical detector may detect reflected signals when the light source 1 and the light source 2 emit light, respectively obtaining a photoelectric signal 1 and a photoelectric signal 2. Since superficially reflected light is linearly polarized light, while multiple backscattered light is non-polarized light, the superficially reflected light component and the multiple backscattered light component included in the photoelectric signal 1 and photoelectric signal 2 may have different characteristics, and values of the intensity of the superficially reflected light and the multiple backscattered light may be calculated according to the characteristics separately.

The processing module may use the reflected light of the skin surface and the backscattered light as input signals, and remove motion artifacts by the adaptive filtering algorithm. The functions, operations, and steps of the storage module and the output module thereafter are the same as those in Embodiment 1.

Embodiment 23

Figure 22F:
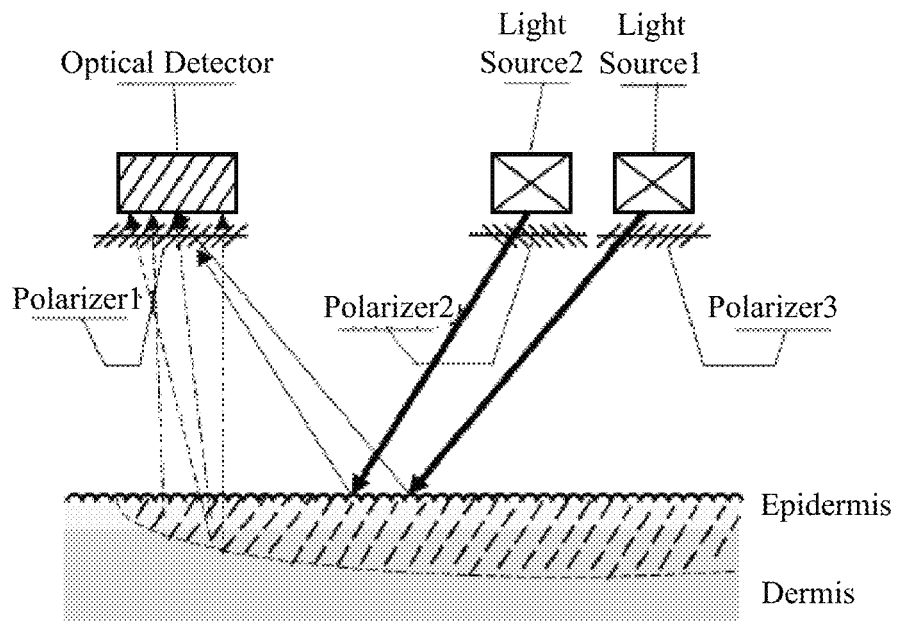

A vital signal detection device may include a detection module different from that described in Embodiment 1. The detection module may have a structure as shown in FIG. 22f, in which a sensor may include one optical detector, two light sources, and three polarizers. Polarizers 2 and 3 are used to generate a polarized light with a normal light source. If a laser is used as the light source (such as a laser diode), the laser already has polarized characteristics, in which case the polarizers 2 and 3 may not be needed. The light sources and the optical detector are at a distance from the skin, and the distance between the two light sources may be very short. Polarization directions of a polarizer 1 and the polarizer 3 are the same and are perpendicular to a polarization direction of the polarizer 2. When the sensor operates, a light source 1 and a light source 2 may emit light alternately, and the optical detector may detect reflected signals when the light source 1 and the light source 2 emit light, respectively obtaining a photoelectric signal 1 and a photoelectric signal 2. Since the polarization directions of the polarizer 1 and the polarizer 3 are the same, the photoelectric signal 1 detected by the photodetector when the light source 1 emits light may include a parallel component of superficially reflected light and a parallel component of multiple backscattered light. Since the polarization direction of the polarizer 2 is perpendicular to the polarization direction of the polarizer 3, a photoelectric signal 2 detected by the photodetector when the light source 2 emits light may not include the superficially reflected light, but only include a perpendicular component of the multiple backscattered light. When the brightness of light emitted by the light source 1 and light source 2 is the same, the multiple backscattered light generated if they emit light are equal since the distance therebetween is very short. When the photoelectric signal 1 is represented as $I_1$, the photoelectric signal 2 is represented as $I_2$, the superficially reflected light is represented as $I_R$, the multiple backscattered light is represented as $I_B$, and subscripts $\parallel$ and $\perp$ represent a parallel component and a perpendicular component respectively, $$I_1 = I_{1R\parallel} + I_{1B\parallel},$$

$$I_2 = I_{2B\perp};$$

the superficially reflected light only has a parallel component, therefore $$I_R = I_{1R\parallel};$$

a skin multiple backscattered light before passing through the polarizer when the light source 2 emits light is defined as $I_B$, and the multiple backscattered light has no polarized characteristics, therefore $$I_B = 2I_{2B\perp}.$$

Since the light source 1 and the light source 2 are at different positions, the intensity of multiple backscattered light reaching the polarizer when the light source 1 emits light is slightly different from that when the light source 2 emits light. When $$I_{1B\parallel} = I_{2B\perp} + \Delta_B,$$

the superficially reflected light and the multiple backscattered light can be calculated by the following two equations separately:

$$I_R = I_1 - I_2 - \Delta_B \text{ and}$$

$$I_B = 2I_2.$$

When $$I_s = 2I_2 \text{ and}$$

$$I_r = I_1 - I_2,$$

the $I_s$ may only include the multiple backscattered light, and $I_r$ may include the superficially reflected light and a very small amount of multiple backscattered light. The $I_s$ may include a motion disturbance signal and a heartbeat signal, and the $I_r$ may basically include only a motion disturbance signal.

The functions, operations, and steps of the processing module, the storage module and the output module thereafter are the same as those in the eighteenth embodiment.

Embodiment 24

Figure 22G:
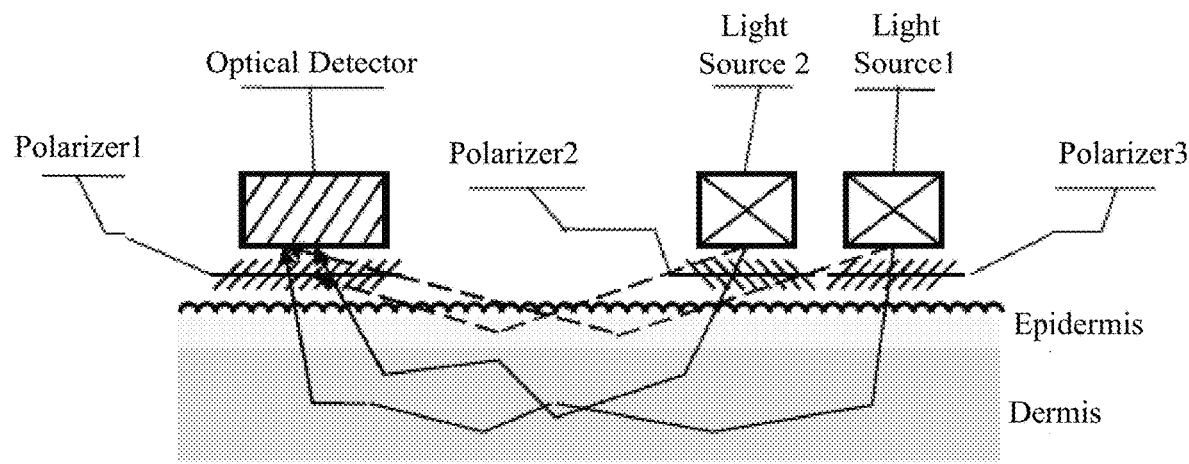

A vital signal detection device may include a detection module different from that described in Embodiment 1. The detection module may have a structure as shown in FIG. 22g, in which a sensor may include one optical detector, two light sources, and three polarizers. Polarizers 2 and 3 are used to generate a polarized light with a normal light source. If a laser is used as the light source (such as a laser diode), the laser already has polarized characteristics, in which case the polarizers 2 and 3 may not be needed. The light sources may be adjacent to the skin surface, the optical detector may be at a distance from the skin or may be adjacent to the skin surface, and the distance between the two light sources may be very short. Polarization directions of a polarizer 1 and the polarizer 3 are the same and are perpendicular to a polarization direction of the polarizer 2. When the sensor operates, a light source 1 and a light source 2 may emit light alternately, and the optical detector may detect reflected signals when the light source 1 and the light source 2 emit light, respectively obtaining a photoelectric signal 1 and a photoelectric signal 2. Since the polarization directions of the polarizer 1 and the polarizer 3 are the same, the photoelectric signal 1 detected by the photodetector when the light source 1 emits light may include a parallel component of less backscattered light and a parallel component of multiple backscattered light. Since the polarization direction of the polarizer 2 is perpendicular to the polarization direction of the polarizer 3, a photoelectric signal 2 detected by the photodetector when the light source 2 emits light may not include the less backscattered light, but only include a perpendicular component of the multiple backscattered light. When the brightness of light emitted by the light source 1 and light source 2 is the same, the multiple backscattered light generated when they emit light are equal since the distance therebetween is very short. When the photoelectric signal 1 is represented as $I_1$, the photoelectric signal 2 is represented as $I_2$, the less backscattered light is represented as $I_{BR}$, the multiple backscattered light is represented as $I_B$, and subscripts $\parallel$ and $\perp$ represent a parallel component and a perpendicular component respectively, $$I_1 = I_{1BR\parallel} + I_{1B\parallel},$$

$$I_2 = I_{2B\perp};$$

the less backscattered light only has a parallel component, therefore $$I_{BR} = I_{1BR\parallel};$$

a skin multiple backscattered light before passing through the polarizer when the light source 2 emits light is defined as $I_B$, and the multiple backscattered light has no polarized characteristics, therefore $$I_B = 2I_{2B\perp}.$$

Since the light source 1 and the light source 2 are at different positions, the intensity of multiple backscattered light reaching the polarizer when the light source 1 emits light is slightly different from that when the light source 2 emits light. When $$I_{1B\parallel} = I_{2B\perp} + \Delta_B,$$

the less backscattered light and the multiple backscattered light can be calculated by the following two equations separately:

$$I_{BR} = I_1 - I_2 - \Delta_B \text{ and}$$

$$I_B = 2I_2.$$

When $$I_s = 2I_2 \text{ and}$$

$$I_r = I_1 - I_2,$$

the may $I_s$ only include the multiple backscattered light, and $I_r$ may include the less backscattered light and a very small amount of multiple backscattered light. The $I_s$ may include a motion disturbance signal and a heartbeat signal, and $I_r$ the may basically include only a motion disturbance signal.

The processing module may use the $I_s$ and $I_r$ as input signals, and remove motion artifacts by the adaptive noise removal algorithm. The functions, operations, and steps of the processing module, the storage module and the output module thereafter are the same as those in the eighteenth embodiment.

Embodiment 25

Figure 22H:
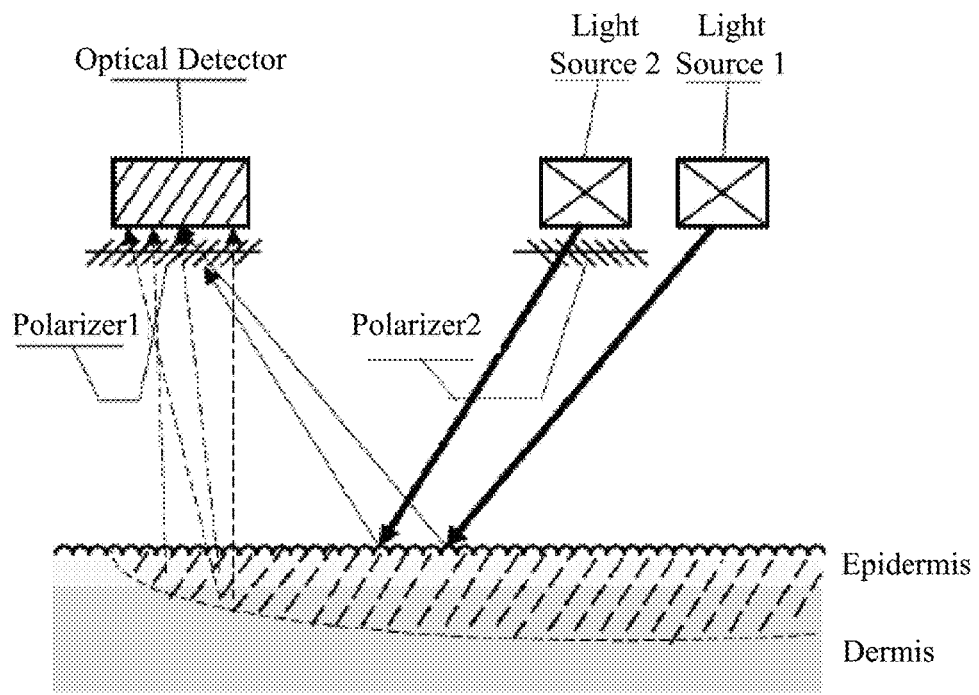

A vital signal detection device may include a detection module different from that described in Embodiment 1. The detection module may have a structure as shown in FIG. 22h, in which a sensor may include one optical detector, two light sources, and two polarizers. A polarizer 2 is used to generate a polarized light with a normal light source. If a laser is used as the light source (such as a laser diode), the laser already has polarized characteristics, in which case the polarizer 2 may not be needed. The light sources and the optical detectors are at a distance from the skin, and the distance between the two light sources may be very short. A polarization direction of a polarizer 1 is perpendicular to a polarization direction of the polarizer 2. When the sensor operates, a light source 1 and a light source 2 may emit light alternately, and the optical detector may detect reflected signals when the light source 1 and the light source 2 emit light, respectively obtaining a photoelectric signal 1 and a photoelectric signal 2. Since there is no polarizer below the light source 1, the photoelectric signal 1 detected by the photodetector when the light source 1 emits light may include a parallel component of superficially reflected light and a parallel component of multiple backscattered light. Since the polarization direction of the polarizer 1 is perpendicular to the polarization direction of the polarizer 2, a photoelectric signal 2 detected by the photodetector when the light source 2 emits light may not include the superficially reflected light, but only include a perpendicular component of the multiple backscattered light. When the brightness of light emitted by the light source 1 is the same as the brightness of light emitted by light source 2 and passing through the polarizer 2, the multiple backscattered light generated when they emit light are equal since the distance therebetween is very short. When the photoelectric signal 1 is represented as $I_1$, the photoelectric signal 2 is represented as $I_2$, the superficially reflected light is represented as $I_R$, the multiple backscattered light is represented as $I_B$, and subscripts $\parallel$ and $\perp$ represent a parallel component and a perpendicular component respectively, $$I_1 = I_{1R\parallel} + I_{1B\parallel},$$

$$I_2 = I_{2B\perp};$$

the photoelectric signal 1 may include the superficially reflected light, therefore $$I_R = 2I_{1R\parallel};$$

a skin multiple backscattered light before passing through the polarizer when the light source 2 emits light is defined as $I_B$, and the multiple backscattered light has no polarized characteristics, therefore $$I_B = 2I_{2B\perp}.$$

Since the light source 1 and the light source 2 are at different positions, the intensity of multiple backscattered light reaching the polarizer when the light source 1 emits light is slightly different from that when the light source 2 emits light. When $$I_{1B\parallel} = I_{2B\perp} + \Delta_B,$$

the superficially reflected light and the multiple backscattered light can be calculated by the following two equations separately:

$$I_R = 2(I_1 - I_2 - \Delta_B) \text{ and}$$

$$I_B = 2I_2.$$

When $$I_s = 2I_2 \text{ and}$$

$$I_r = 2(I_1 - I_2),$$

the $I_s$ may only include the multiple backscattered light, and $I_r$ may include superficial scattering light and a very small amount of multiple backscattered light. The $I_s$ may include a motion disturbance signal and a heartbeat signal, and $I_r$ the may basically include only a motion disturbance signal.

The functions, operations, and steps of the processing module, the storage module and the output module thereafter are the same as those in the eighteenth embodiment.

Embodiment 26

Figure 22I:
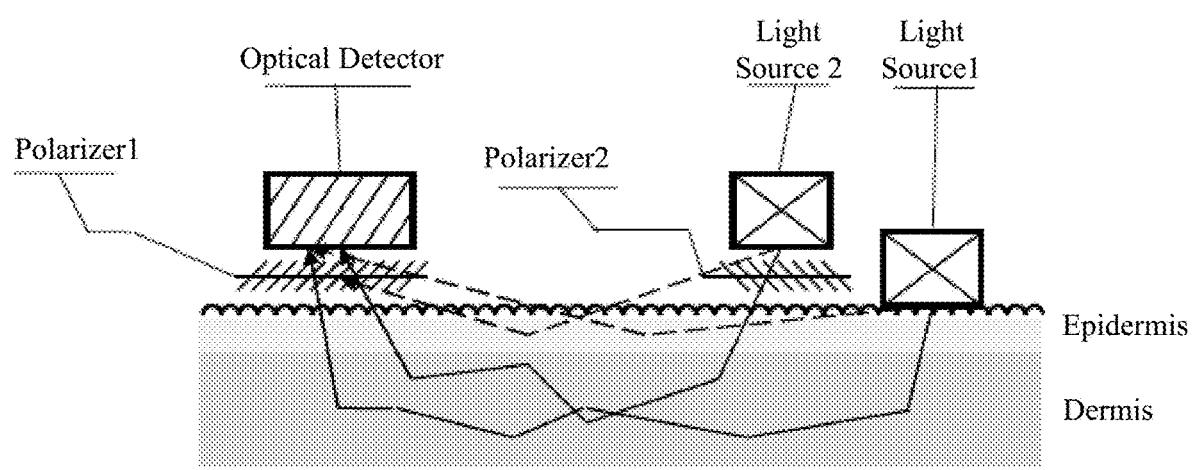

A vital signal detection device may include a detection module different from that described in Embodiment 1. The detection module may have a structure as shown in FIG. 22i in which a sensor may include one optical detector, two light sources, and two polarizers. A polarizer 2 is used to generate a polarized light with a normal light source. If a laser is used as the light source (such as a laser diode), the laser already has polarized characteristics, in which case the polarizers 2 may not be needed. The light sources may be adjacent to the skin surface, the optical detector may be at a distance from the skin or may be adjacent to the skin surface, and the distance between the two light sources may be very short. A polarization direction of a polarizer 1 is perpendicular to a polarization direction of the polarizer 2. When the sensor operates, a light source 1 and a light source 2 may emit light alternately, and the optical detector may detect reflected signals when the light source 1 and the light source 2 emit light, respectively obtaining a photoelectric signal 1 and a photoelectric signal 2. Since there is no polarizer below the light source 1, the photoelectric signal 1 detected by the photodetector when the light source 1 emits light may include a parallel component of less backscattered light and a parallel component of multiple backscattered light. Since the polarization direction of the polarizer 1 is perpendicular to the polarization direction of the polarizer 2, a photoelectric signal 2 detected by the photodetector when the light source 2 emits light may not include the less backscattered light, but only include a perpendicular component of the multiple backscattered light. When the brightness of light emitted by the light source 1 is the same as the brightness of light emitted by light source 2 and passing through the polarizer 2, the multiple backscattered light generated when they emit light are equal since a distance therebetween is very short. When the photoelectric signal 1 is represented as $I_1$, the photoelectric signal 2 is represented as $I_2$, the less backscattered light is represented as $I_{BR}$, the multiple backscattered light is represented as $I_B$, and subscripts $\parallel$ and $\perp$ represent a parallel component and a perpendicular component respectively, $$I_1 = I_{1BR\|} + I_{1B\|},$$

$$I_2 = I_{2B\perp};$$

the photoelectric signal 1 may include the less backscattered light, therefore $$I_{BR} = 2I_{1BR\|};$$

a skin multiple backscattered light before passing through the polarizer when the light source 2 emits light is defined as $I_B$, since the multiple backscattered light has no polarized characteristics, therefore $$I_B = 2I_{2B\perp}.$$

Since the light source 1 and the light source 2 are at different positions, the intensity of multiple backscattered light reaching the polarizer when the light source 1 emits light is slightly different from that when the light source 2 emits light. When $$I_{1B\|} = I_{2B\perp} + \Delta_B,$$

the less backscattered light and the multiple backscattered light can be calculated by the following two equations separately:

$$I_{BR} = 2(I_1 - I_2 - \Delta_B) \text{ and}$$

$$I_B = 2I_2.$$

When $$I_s = 2I_2 \text{ and}$$

$$I_r = 2(I_1 - I_2),$$

the $I_s$ may only include the multiple backscattered light, and $I_r$ may include the less backscattered light and a very small amount of multiple backscattered light. The $I_s$ may include a motion disturbance signal and a heartbeat signal, and the $I_r$ may basically include only a motion disturbance signal.

The functions, operations, and steps of the processing module, the storage module and the output module thereafter are the same as those in the eighteenth embodiment.

Embodiment 27

Figure 23A:
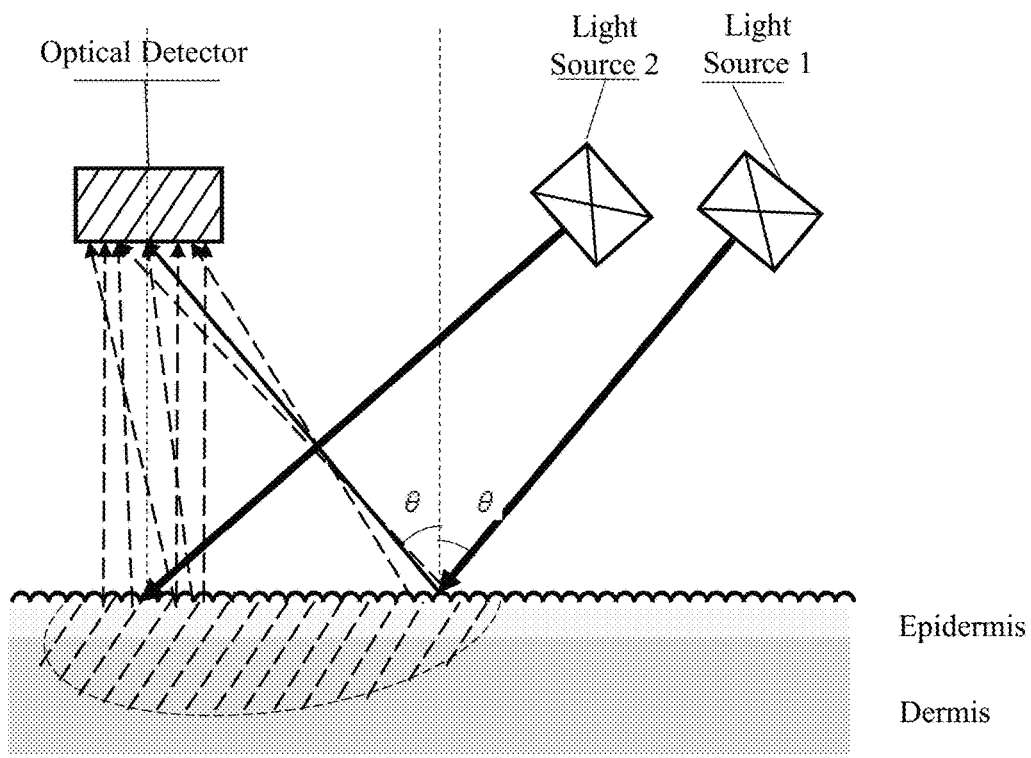

A vital signal detection device may include a detection module different from that described in Embodiment 1. The detection module may have a structure as shown in FIG. 23a, in which a sensor may include one optical detector and two light sources. The light sources and the optical detector are at a distance from the skin. The skin surface is taken as a medium interface, the incident angle of light emitted by a light source 1 is θ, the optical detector is located at a theoretical specular reflection area on a plane determined by the incident light and a normal, and the angle between the normal and a line connecting the optical detector and an incident point is also θ. An intersection of light emitted by a light source 2 and the skin is located right under the optical detector, the detector is located near a normal of a light point where the light of the light source 2 is emitted on the skin, and the closer the detector is to the normal direction, the better the signal quality is. When the sensor operates, the light source 1 and the light source 2 may emit light alternately, and the optical detector may detect reflected signals when the light source 1 and the light source 2 emit light, respectively obtaining a photoelectric signal 1 and a photoelectric signal 2. Since the optical detector is located at a direction where reflected light of the surface of the light source 1 is the strongest, the photoelectric signal 1 detected by the photodetector when the light source 1 emits light may include a large component of reflected light of the skin surface. Since the optical detector is located at a direction where backscattered light of the light emitted by the light source 2 is the strongest, the photoelectric signal 2 detected by the photodetector when the light source 2 emits light may include a large component of backscattered light. The photoelectric signal 1 is represented as $I_1$, and the photoelectric signal 2 is represented as $I_2$.

The processing module may use the $I_1$ and $I_2$ as input signals, and remove motion artifacts by the adaptive noise removal algorithm. The functions, operations, and steps of the storage module and the output module thereafter are the same as those in Embodiment 1.

Embodiment 28

Figure 23B:
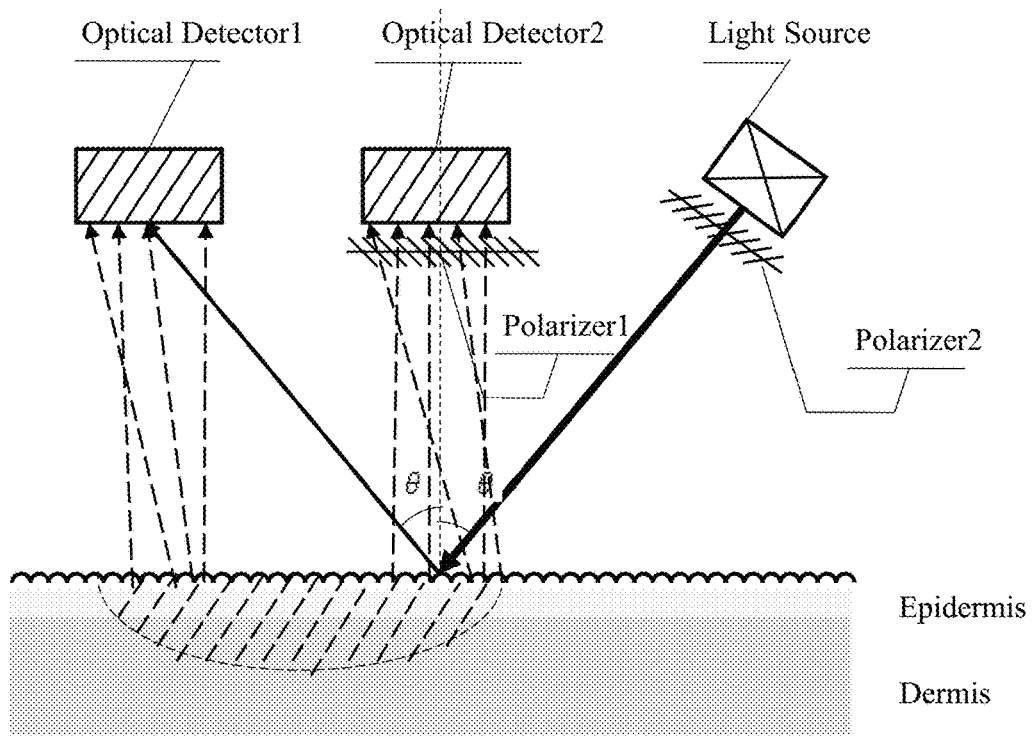

A vital signal detection device may include a detection module different from that described in Embodiment 1. The detection module may have a structure as shown in FIG. 23b, in which a sensor may include one light source, two optical detectors, and two polarizers. A polarizer 2 is used to generate a polarized light with a normal light source. If a laser is used as the light source (such as a laser diode), the laser already has polarized characteristics, in which case the polarizer 2 may not be needed. The light source and the optical detectors are at a distance from the skin. A polarization direction of a polarizer 1 is perpendicular to a polarization direction of the polarizer 2. The skin surface is taken as a medium interface, the incident angle of light emitted by the light source is θ, an optical detector 1 is located at a theoretical specular reflection area on a plane determined by the incident light and a normal, and the angle between the normal and a line connecting the optical detector and an incident point is also θ. An optical detector 2 is located in a direction near the normal. The detector 2 is located near the normal, and the closer the detector is to the normal, the better the signal quality is. For example, the degree is preferably 90°, may be in a range of 80° to 100°, or in a range of 60° to 120, and is less preferably smaller than 60° or bigger than 120°. When the sensor operates, an optical detector 1 and an optical detector 2 may detect reflected signals when the light source emits light, respectively obtaining a photoelectric signal 1 and a photoelectric signal 2. Since there is no polarizer below the optical detector 1, the photoelectric signal 1 detected by the photodetector 1 may include superficially reflected light and multiple backscattered light, and since the optical detector 1 is located at a direction where reflected light of the surface is the strongest, the photoelectric signal 1 may include a large component of superficially reflected light. Since the polarization direction of the polarizer 1 is perpendicular to the polarization direction of the polarizer 2, the photoelectric signal 2 detected by the photodetector 2 may not include the superficially reflected light, but only include a perpendicular component of the multiple backscattered light, and since the optical detector 2 is located at a direction where the backscattered light is the strongest, the photoelectric signal 2 may include a large component of the multiple backscattered light. When the photoelectric signal 1 is represented as $I_1$, the photoelectric signal 2 is represented as $I_2$, the superficially reflected light is represented as $I_R$, the multiple backscattered light is represented as $I_B$, and subscripts $\|$ and $\perp$ represent a parallel component and a perpendicular component respectively, $$I_1 = I_{1R} + I_{1B} \text{ and}$$

$I_2 = I_{2B\perp}$.

Since there is a certain distance between the optical detector 1 and the optical detector 2, components of the multiple backscattered light included in the photoelectric signal 1 and the photoelectric signal 2 are not equal. The processing module may use the $I_2$ and the $I_1$ as input signals, and remove motion artifacts by the adaptive noise removal algorithm. The functions, operations, and steps of the storage module and the output module thereafter are the same as those in Embodiment 1.

Embodiment 29

Figure 24A:
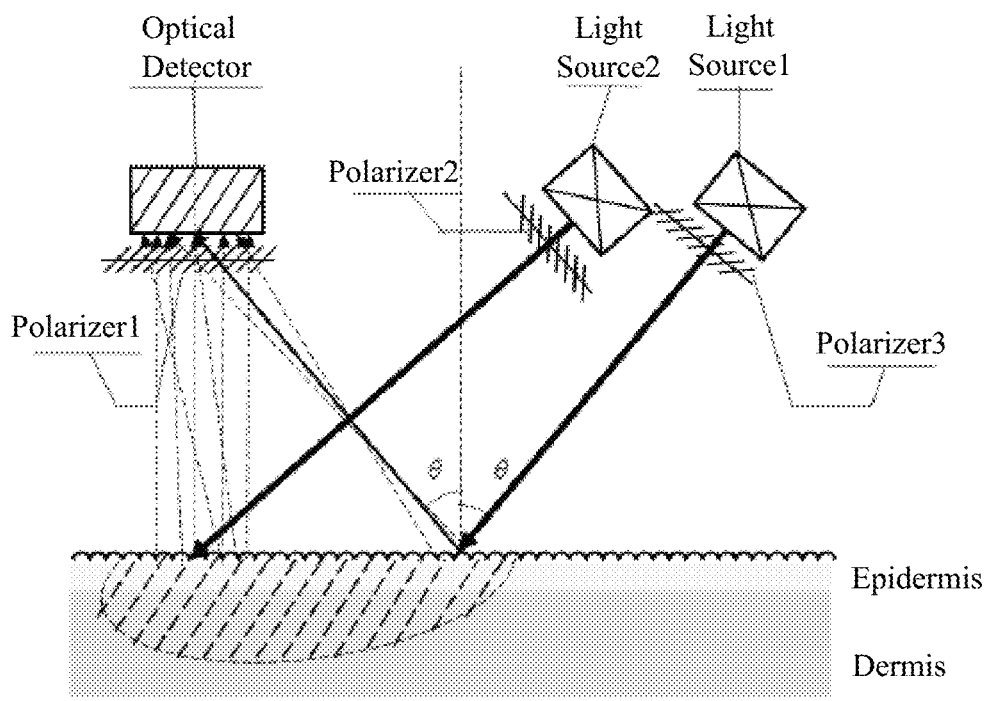

A vital signal detection device may include a detection module different from that described in Embodiment 1. The detection module may have a structure as shown in FIG. 24a, in which a sensor may include one optical detector, two light sources, and three polarizers. The light sources and the optical detector are at a distance from the skin. Polarization directions of a polarizer 1 and the polarizer 3 are the same and are perpendicular to a polarization direction of the polarizer 2. The polarizers 2 and 3 are used to generate a polarized light with a normal light source. If a laser is used as the light source (such as a laser diode), the laser already has polarized characteristics, in which case the polarizers 2 and 3 may not be needed. The skin surface is taken as a medium interface, the incident angle of light emitted by a light source 1 is θ, the optical detector is located at a theoretical specular reflection area on a plane determined by the incident light and a normal, and the angle between the normal and a line connecting the optical detector and an incident point is also θ. An intersection of light emitted by a light source 2 and the skin is located right under the optical detector. When the sensor operates, a light source 1 and a light source 2 may emit light alternately, and the optical detector may detect reflected signals when the light source 1 and the light source 2 emit light, respectively obtaining a photoelectric signal 1 and a photoelectric signal 2. Since the polarization directions of the polarizer 1 and the polarizer 3 are the same, the photoelectric signal 1 detected by the photodetector when the light source 1 emits light may include a parallel component of superficially reflected light and a parallel component of superficially reflected light and a parallel component of multiple backscattered light, and since the optical detector is located at a direction where reflected light of the surface of the light source 1 is the strongest, the photoelectric signal 1 may include a large component of reflected light of the skin surface. Since the polarization direction of the polarizer 2 is perpendicular to the polarization direction of the polarizer 3, the photoelectric signal 2 detected by the photodetector when the light source 2 emits light may not include the superficially reflected light, but only include a perpendicular component of the multiple backscattered light, and since the optical detector is located at a direction where backscattered light of light emitted by the light source 2 is the strongest, the photoelectric signal 2 may include a large component of the backscattered light. When brightness of light emitted by the light source 1 and light source 2 is the same, the backscattered light generated when they emit light are equal since a distance therebetween is very short. When the photoelectric signal 1 is represented as $I_1$, the photoelectric signal 2 is represented as $I_2$, the superficially reflected light is represented as $I_R$, the multiple backscattered light is represented as $I_B$, and subscripts ∥ and ⊥ represent a parallel component and a perpendicular component respectively, $I_1 = I_{1R\parallel} + I_{1B\parallel}$ and $I_2 = I_{2B\perp}$.

Since there is a certain distance between the optical detector 1 and the optical detector 2, components of the multiple backscattered light included in the photoelectric signal 1 and the photoelectric signal 2 are not equal. The processing module may use the $I_2$ and the $I_1$ as input signals, and remove motion artifacts by the adaptive noise removal algorithm. The functions, operations, and steps of the storage module and the output module thereafter are the same as those in Embodiment 1.

Embodiment 30

Figure 24B:
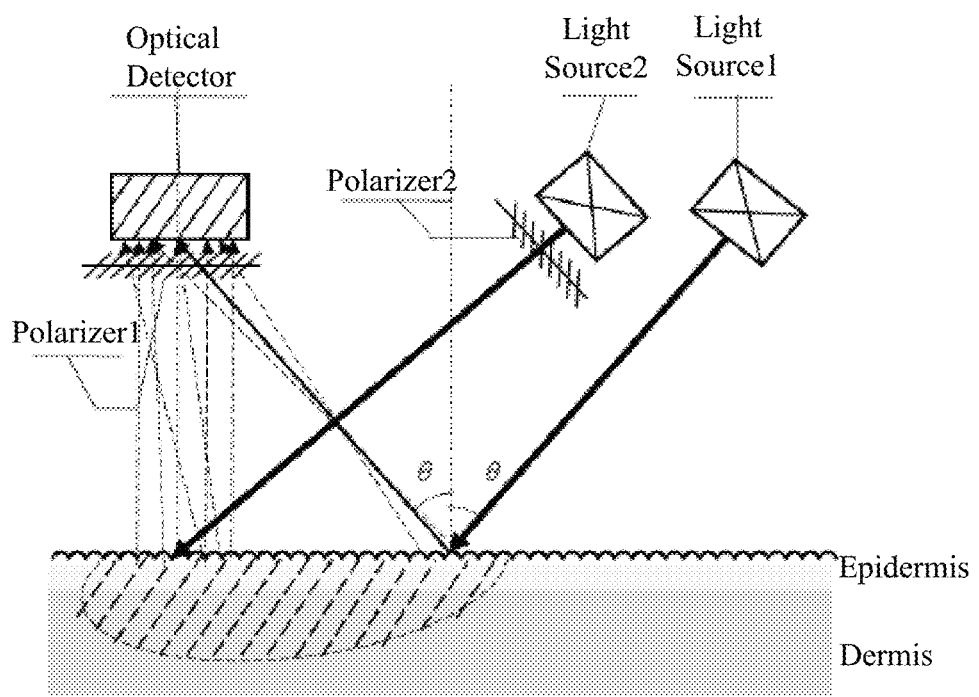

A vital signal detection device may include a detection module different from that described in Embodiment 1. The detection module may have a structure as shown in FIG. 24b, in which a sensor may include one light source, two optical detectors, and two polarizers. The light sources and the optical detector are at a distance from the skin. A polarization direction of a polarizer 1 is perpendicular to a polarization direction of the polarizer 2. A polarizer 2 is used to generate a polarized light with a normal light source. If a laser is used as the light source (such as a laser diode), the laser already has polarized characteristics, in which case the polarizer 2 may not be needed. The skin surface is taken as a medium interface, the incident angle of light emitted by a light source 1 is θ, the optical detector is located at a theoretical specular reflection area on a plane determined by the incident light and a normal, and the angle between the normal and a line connecting the optical detector and an incident point is also θ. An intersection of light emitted by a light source 2 and the skin is located right under the optical detector. When the sensor operates, a light source 1 and a light source 2 may emit light alternately, and the optical detector may detect reflected signals when the light source 1 and the light source 2 emit light, respectively obtaining a photoelectric signal 1 and a photoelectric signal 2. Since there is no polarizer below the light source 1, the photoelectric signal 1 detected by the photodetector when the light source 1 emits light may include a parallel component of superficially reflected light and a parallel component of superficially reflected light and a parallel component of multiple backscattered light, and since the optical detector is located at a direction where reflected light of the surface of the light source 1 is the strongest, the photoelectric signal 1 may include a large component of reflected light of the skin surface. Since the polarization direction of the polarizer 1 is perpendicular to the polarization direction of the polarizer 2, the photoelectric signal 2 detected by the photodetector when the light source 2 emits light may not include the superficially reflected light, but only include a perpendicular component of the multiple backscattered light, and since the optical detector is located at a direction where backscattered light of light emitted by the light source 2 is the strongest, the photoelectric signal 2 may include a large component of the multiple backscattered light. When brightness of light emitted by the light source 1 is the same as the brightness of light emitted by light source 2 and passing through the polarizer 2, the multiple backscattered light generated when they emit light are equal since a distance therebetween is very short. When the photoelectric signal 1 is represented as $I_1$, the photoelectric signal 2 is represented as $I_2$, the superficially reflected light is represented as $I_R$, the multiple backscattered light is represented as $I_B$, and subscripts ∥ and ⊥ represent a parallel component and a perpendicular component respectively, $I_1 = I_{1R\parallel} + I_{1B\parallel}$ and $I_2 = I_{2B\perp}$.

Since there is a certain distance between the optical detector 1 and the optical detector 2, components of the multiple backscattered light included in the photoelectric signal 1 and the photoelectric signal 2 are not equal. The processing module may use the $I_2$ and the $I_1$ as input signals, and remove motion artifacts by the adaptive noise removal algorithm. The functions, operations, and steps of the storage module and the output module thereafter are the same as those in Embodiment 1.

Embodiment 31

Figure 25A:
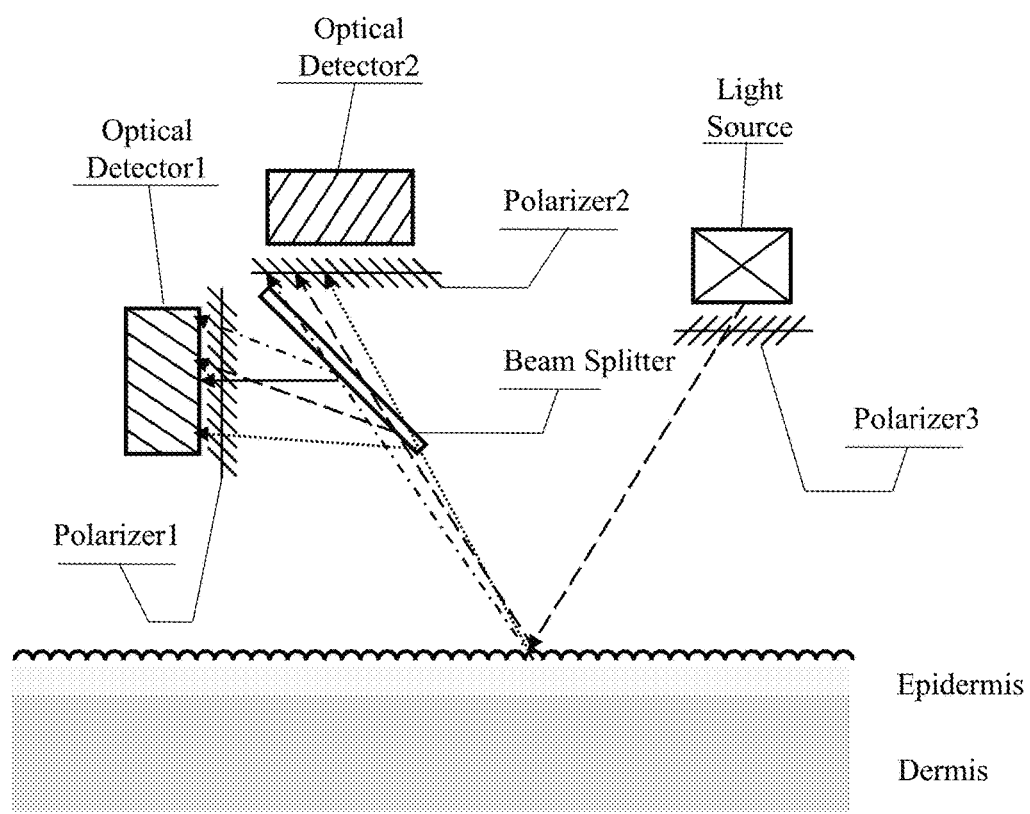

A vital signal detection device may include a detection module different from that described in Embodiment 1. The detection module may have a structure as shown in FIG. 25a, in which a sensor may include one light source, two optical detectors, three polarizers, and one beam splitter. A polarizer 3 is used to generate a polarized light with a normal light source. If a laser is used as the light source (such as a laser diode), the laser already has polarized characteristics, in which case the polarizer 3 may not be needed. The light source and the optical detectors are at a distance from the skin, and the two optical detectors and the polarizers are located at reflection and transmission directions of the beam splitter respectively. Polarization directions of a polarizer 1 and the polarizer 3 are the same and are perpendicular to a polarization direction of the polarizer 2. The reflected and transmitted components caused by the beam splitter may be the same. When the sensor operates, an optical detector 1 and an optical detector 2 may detect reflected signals when the light source emits light, respectively obtaining a photoelectric signal 1 and a photoelectric signal 2. Since the polarization directions of the polarizer 1 and the polarizer 3 are the same, the photoelectric signal 1 detected by the photodetector 1 may include a parallel component of superficially reflected light and a parallel component of multiple backscattered light. Since the polarization direction of the polarizer 2 is perpendicular to the polarization direction of the polarizer 3, a photoelectric signal 2 detected by the photodetector 2 may not include the superficially reflected light, but only include a perpendicular component of the multiple backscattered light. When the photoelectric signal 1 is represented as $I_1$, the photoelectric signal 2 is represented as $I_2$, the superficially reflected light is represented as $I_R$, the multiple backscattered light is represented as $I_B$, and subscripts ∥ and ⊥ represent a parallel component and a perpendicular component respectively, $I_1 = I_{R\parallel} + I_{B\parallel}$, $I_2 = I_{B\perp}$; and the superficially reflected light only has a parallel component and the multiple backscattered light has no polarized characteristics, therefore $I_R = I_{R\parallel}$, $I_B = 2I_{B\perp}$.

Then, the superficially reflected light and the multiple backscattered light can be calculated by the following two equations separately:

$I_R = I_1 - I_2$ and $I_B = 2I_2$.

The processing module may use the $I_R$ and $I_B$ as input signals, and remove motion artifacts by the adaptive noise removal algorithm. The functions, operations, and steps of the storage module and the output module thereafter are the same as those in Embodiment 1.

Embodiment 32

Figure 25B:
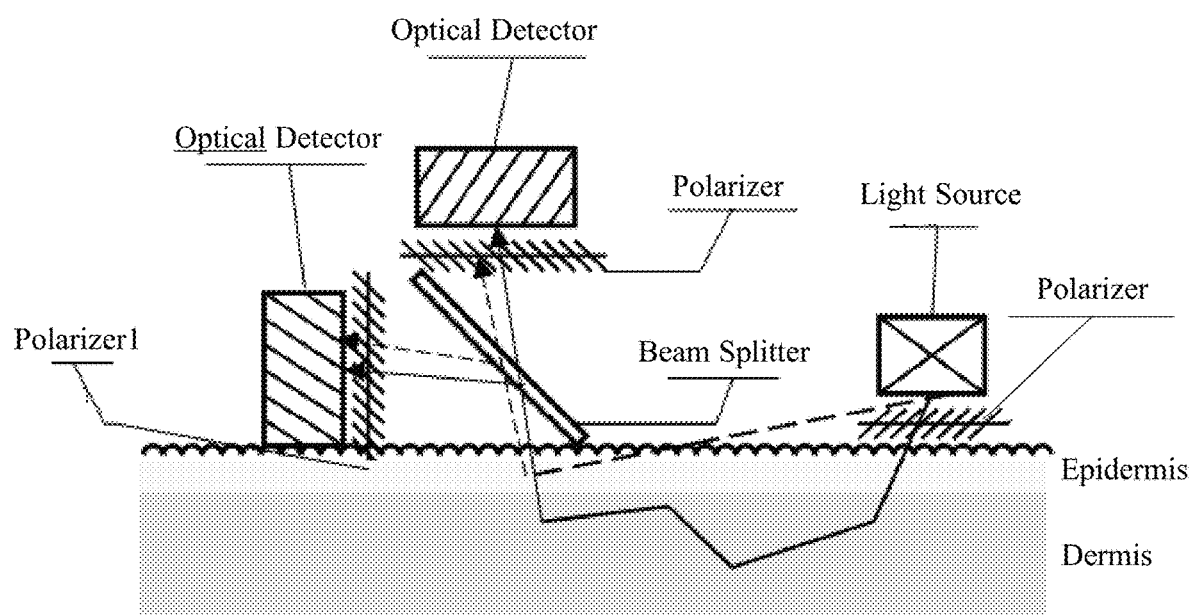

A vital signal detection device may include a detection module different from that described in Embodiment 1. The detection module may have a structure as shown in FIG. 25b, in which a sensor may include one light source, two optical detectors, three polarizers, and one beam splitter. A polarizer 3 is used to generate a polarized light with a normal light source. If a laser is used as the reflection and transmission direction (such as a laser diode), the laser already has polarized characteristics, in which case the polarizers 3 may not be needed. The light source may be adjacent to the skin surface, the two optical detectors may be at a distance from the skin or may be adjacent to the skin surface, and the two optical detectors and the polarizers are located at reflection and transmission directions of the beam splitter respectively. Polarization directions of a polarizer 1 and the polarizer 3 are the same and are perpendicular to a polarization direction of the polarizer 2. The reflected and transmitted components caused by the beam splitter may be the same.

When the sensor operates, an optical detector 1 and an optical detector 2 may detect reflected signals when the light source emits light, respectively obtaining a photoelectric signal 1 and a photoelectric signal 2. Since the polarization directions of the polarizer 1 and the polarizer 3 are the same, the photoelectric signal 1 detected by the photodetector 1 may include a parallel component of less backscattered light and a parallel component of multiple backscattered light. Since the polarization direction of the polarizer 2 is perpendicular to the polarization direction of the polarizer 3, a photoelectric signal 2 detected by the photodetector 2 may not include the less backscattered light, but only include a perpendicular component of the multiple backscattered light. When the photoelectric signal 1 is represented as $I_1$, the photoelectric signal 2 is represented as $I_2$, the less backscattered light is represented as $I_{BR}$, the multiple backscattered light is represented as $I_B$, and subscripts ∥ and ⊥ represent a parallel component and a perpendicular component respectively, $I_1 = I_{BR\parallel} + I_{B\parallel}$, $I_2 = I_{B\perp}$; and the superficially reflected light only has a parallel component and the multiple backscattered light has no polarized characteristics, therefore $I_{BR} = I_{BR\parallel}$, $I_B = 2I_{B\perp}$.

Then, the superficially reflected light and the multiple backscattered light can be calculated by the following two equations separately:

$I_{BR} = I_1 - I_2$ and $I_B = 2I_2$.

The processing module may use the $I_{BR}$ and $I_B$ as input signals, and remove motion artifacts by the adaptive noise removal algorithm. The functions, operations, and steps of the storage module and the output module thereafter are the same as those in Embodiment 1.

Embodiment 33

Figure 25C:
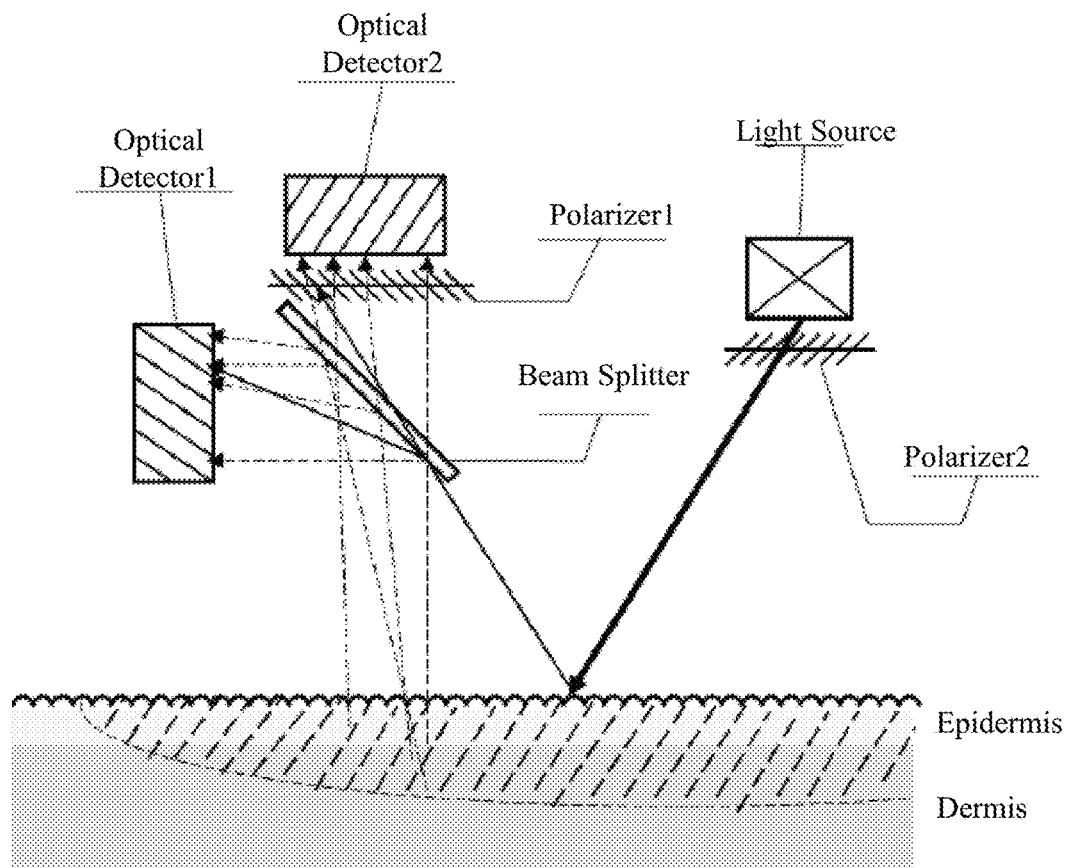

A vital signal detection device may include a detection module different from that described in Embodiment 1. The detection module may have a structure as shown in FIG. 25c, in which a sensor may include one light source, two optical detectors, two polarizers, and one beam splitter. A polarizer 2 is used to generate a polarized light with a normal light source. If a laser is used as the light source (such as a laser diode), the laser already has polarized characteristics, in which case the polarizer 2 may not be used. The light source and the optical detectors are at a distance from the skin, an optical detector 1 is located at a reflection direction of the beam splitter, and an optical detector 2 and a polarizer 1 are located at a transmission direction of the beam splitter. A polarization direction of a polarizer 1 is perpendicular to a polarization direction of the polarizer 2. The reflected and transmitted components caused by the beam splitter may be the same. When the sensor operates, an optical detector 1 and an optical detector 2 may detect reflected signals when the light source emits light, respectively obtaining a photoelectric signal 1 and a photoelectric signal 2. Since there is no polarizer below the optical detector 1, the photoelectric signal 1 detected by the photodetector 1 may include superficially reflected light and multiple backscattered light. Since the polarization direction of the polarizer 1 is perpendicular to the polarization direction of the polarizer 2, a photoelectric signal 2 detected by the sensor 2 may not include the superficially reflected light, but only include a perpendicular component of the multiple backscattered light. When the photoelectric signal 1 is represented as $I_1$, the photoelectric signal 2 is represented as $I_2$, the superficially reflected light is represented as $I_R$, the multiple backscattered light is represented as $I_B$, and subscripts $\|$ and $\perp$ represent a parallel component and a perpendicular component respectively, $$I_1 = I_R + I_B,$$

$$I_2 = I_{B\perp}; \text{ and}$$

the superficially reflected light only has a parallel component and the multiple backscattered light has no polarized characteristics, therefore $$I_R = I_{R\|},$$

$$I_B = 2I_{B\perp}.$$

Then, the superficially reflected light and the multiple backscattered light can be calculated by the following two equations separately $$I_R = I_1 - 2I_2 \text{ and}$$

$$I_B = 2I_2.$$

The processing module may use the $I_R$ and $I_B$ as input signals, and remove motion artifacts by the adaptive noise removal algorithm. The functions, operations, and steps of the storage module and the output module thereafter are the same as those in Embodiment 1.

Embodiment 34

Figure 25D:
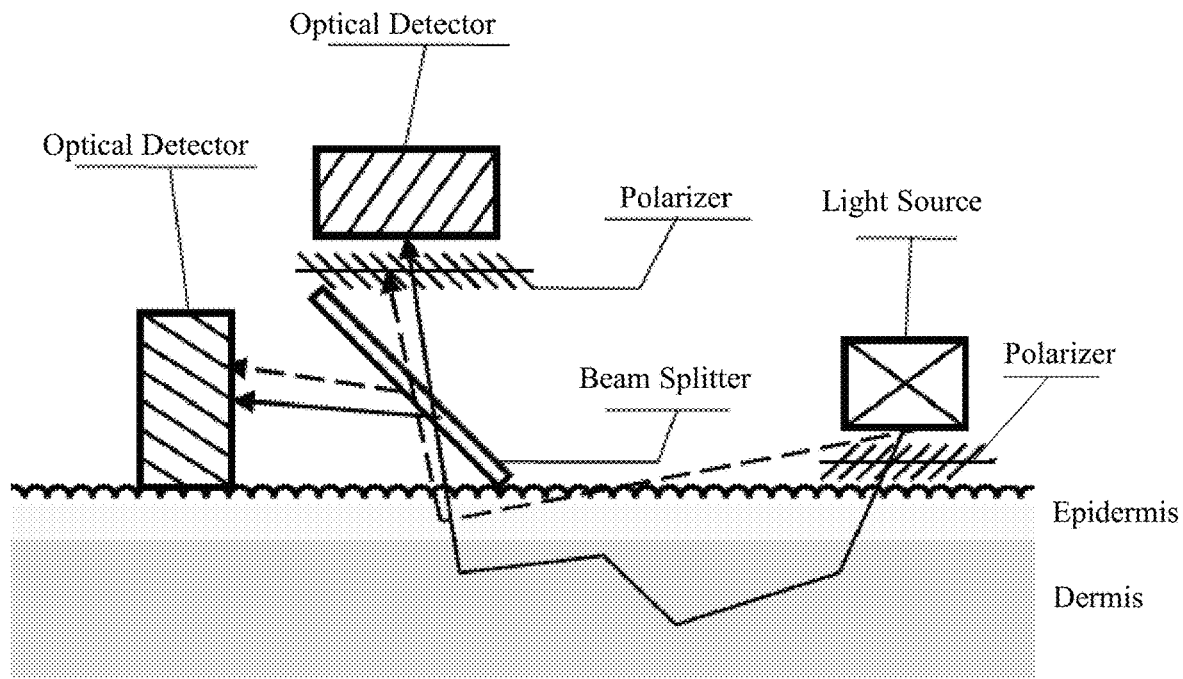

A vital signal detection device may include a detection module different from that described in Embodiment 1. The detection module may have a structure as shown in FIG. 25d, in which a sensor may include one light source, two optical detectors, two polarizers, and one beam splitter. A polarizer 2 is used to generate a polarized light with a normal light source. If a laser is used as the reflection and transmission direction (such as a laser diode), the laser already has polarized characteristics, in which case the polarizers 2 may not be needed. The light source may be adjacent to the skin surface, the two optical detectors may be at a distance from the skin or may be adjacent to the skin surface, and the two optical detectors and the polarizers are located at reflection and transmission directions of the beam splitter respectively. A polarization direction of a polarizer 1 is perpendicular to a polarization direction of the polarizer 2. The reflected and transmitted components caused by the beam splitter may be the same. When the sensor operates, an optical detector 1 and an optical detector 2 may detect reflected signals when the light source emits light, respectively obtaining a photoelectric signal 1 and a photoelectric signal 2. Since there is no polarizer below the optical detector 1, the photoelectric signal 1 detected by the photodetector 1 may include less backscattered light and multiple backscattered light. Since the polarization direction of the polarizer 1 is perpendicular to the polarization direction of the polarizer 2, the photoelectric signal 2 detected by the sensor 2 may not include the less backscattered light, but only include a perpendicular component of the multiple backscattered light. When the photoelectric signal 1 is represented as $I_1$, the photoelectric signal 2 is represented as $I_2$, the less backscattered light is represented as $I_{BR}$ the multiple backscattered light is represented as $I_B$, and subscripts $\|$ and $\perp$ represent a parallel component and a perpendicular component respectively, $$I_1 = I_{BR} + I_B,$$

$$I_2 = I_{B\perp}; \text{ and}$$

the less backscattered light only has a parallel component and the multiple backscattered light has no polarized characteristics, therefore $$I_{BR} = I_{BR\|},$$

$$I_B = 2I_{B\perp}.$$

Then, the superficially reflected light and the multiple backscattered light can be calculated by the following two equations separately $$I_{BR} = I_1 - 2I_2 \text{ and}$$

$$I_B = 2I_2.$$

The processing module may use the $I_{BR}$ and $I_B$ as input signals, and remove motion artifacts by the adaptive noise removal algorithm. The functions, operations, and steps of the storage module and the output module thereafter are the same as those in Embodiment 1.

Embodiment 35

Figure 26A:
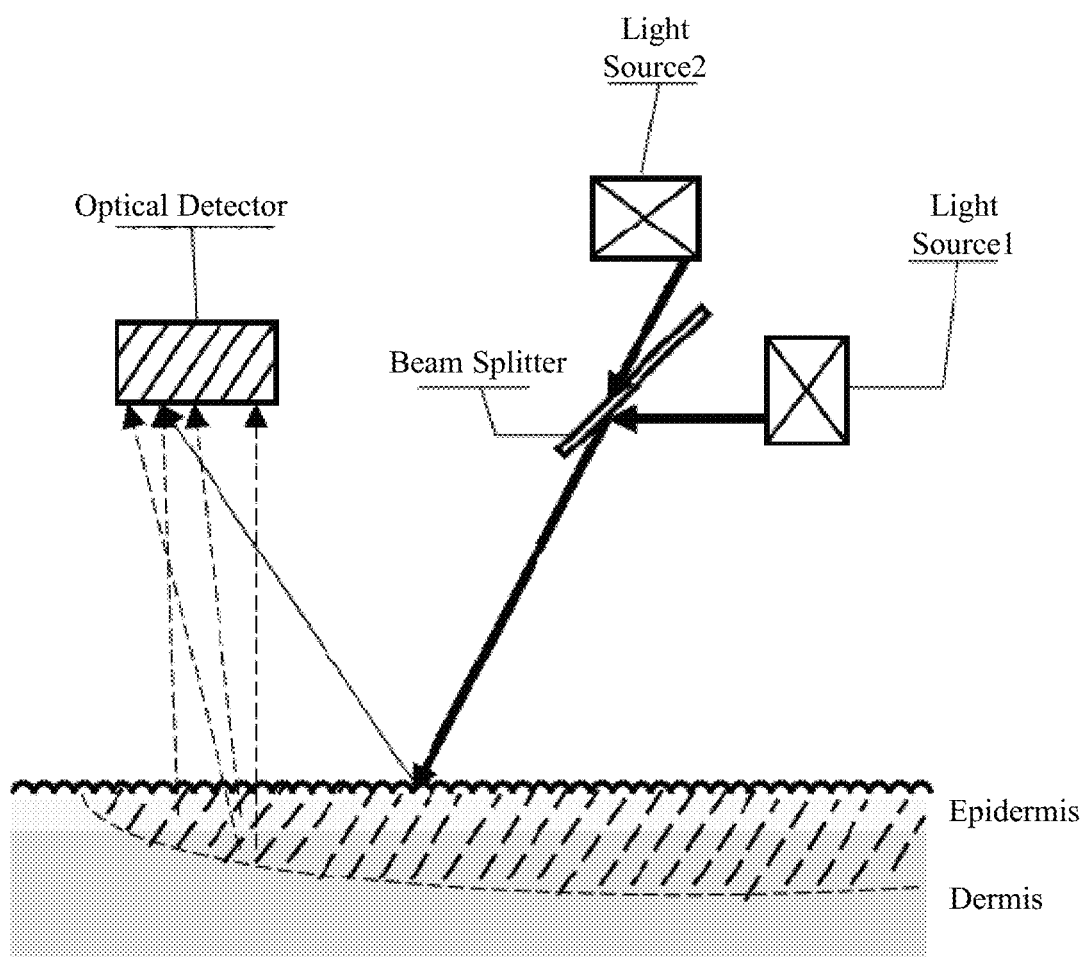

A vital signal detection device may include a detection module different from that described in Embodiment 1. The detection module may have a structure as shown in FIG. 26a, in which a sensor may include two light sources that can generate linearly polarized light, one optical detector that can detect light with different polarized characteristics, and one beam splitter. The light sources and the optical detector are at a distance from the skin, and the two light sources are located at reflection and transmission directions of the beam splitter respectively. When the sensor operates, a light source 1 and a light source 2 may emit light alternately, and the optical detector may detect reflected signals when the light source 1 and the light source 2 emit light, respectively obtaining a photoelectric signal 1 and a photoelectric signal 2. Since superficially reflected light is linearly polarized light, while multiple backscattered light is non-polarized light, the superficially reflected light component and the multiple backscattered light component included in the photoelectric signal 1 and photoelectric signal 2 may have different characteristics, and values of the intensity of the superficially reflected light and the multiple backscattered light may be calculated according to the characteristics separately.

The processing module may use the superficially reflected light and the multiple backscattered light as input signals, and remove motion artifacts by the adaptive filtering algorithm. The functions, operations, and steps of the storage module and the output module thereafter are the same as those in Embodiment 1.

Embodiment 36

Figure 26B:
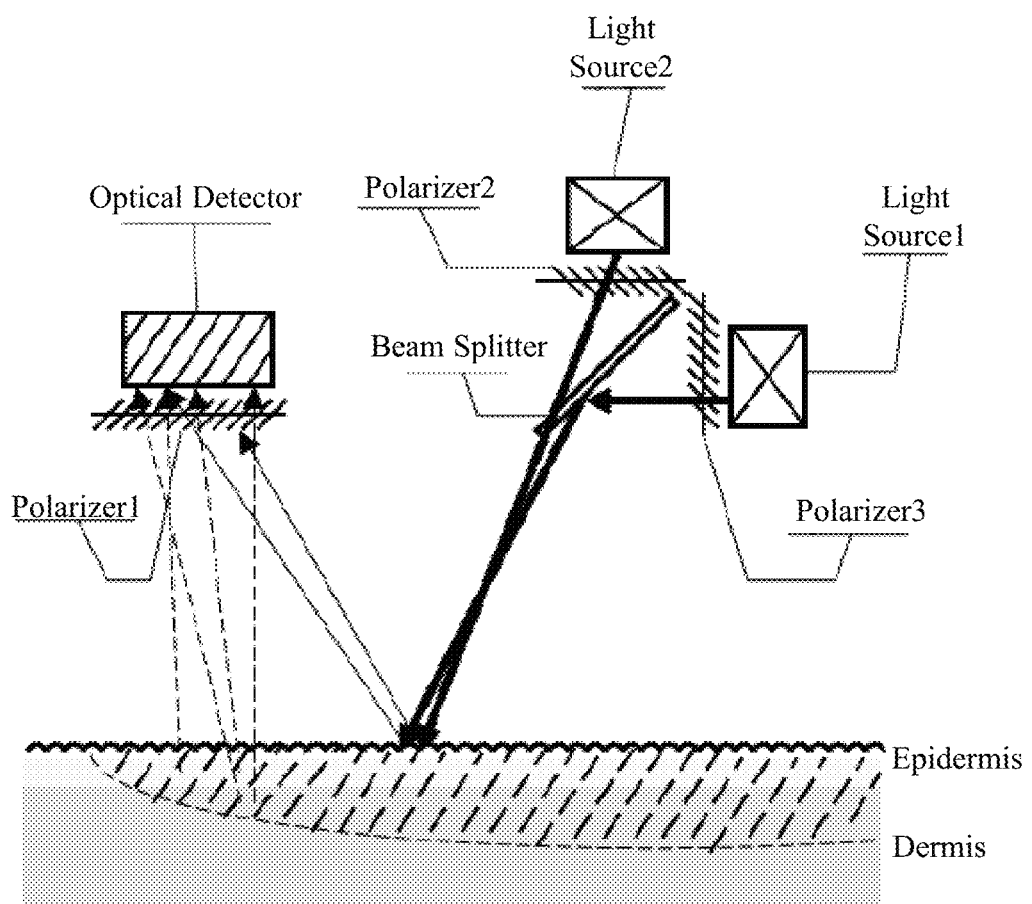

A vital signal detection device may include a detection module different from that described in Embodiment 1. The detection module may have a structure as shown in FIG. 26b, in which a sensor may include one optical detector, two light sources, three polarizers, and one beam splitter. Polarizer 2 and 3 are used to generate a polarized light with a normal light source. If a laser is used as the light source (such as a laser diode), the laser already has polarized characteristics, in which case the polarizers 2 and 3 may not be needed. The light sources and the optical detector are at a distance from the skin, and the two light sources and the polarizers are located at reflection and transmission directions of the beam splitter respectively. Polarization directions of a polarizer 1 and the polarizer 3 are the same and are perpendicular to a polarization direction of the polarizer 2. The reflected and transmitted components caused by the beam splitter may be the same. When the sensor operates, a light source 1 and a light source 2 may emit light alternately, and the optical detector may detect reflected signals when the light source 1 and the light source 2 emit light, respectively obtaining a photoelectric signal 1 and a photoelectric signal 2. Since the polarization directions of the polarizer 1 and the polarizer 3 are the same, the photoelectric signal 1 detected by the photodetector when the light source 1 emits light may include a parallel component of superficially reflected light and a parallel component of multiple backscattered light. Since the polarization direction of the polarizer 2 is perpendicular to the polarization direction of the polarizer 3, a photoelectric signal 2 detected by the photodetector when the light source 2 emits light may not include the superficially reflected light, but only include a perpendicular component of the multiple backscattered light. When the brightness of light emitted by the light source 1 and light source 2 is the same, the multiple backscattered light generated when they emit light are equal since components reflected and transmitted by the beam splitter are equal. When the photoelectric signal 1 is represented as $I_1$, the photoelectric signal 2 is represented as $I_2$, the superficially reflected light is represented as $I_R$, the multiple backscattered light is represented as $I_B$, and subscripts $\parallel$ and $\perp$ represent a parallel component and a perpendicular component respectively, $$I_1 = I_{R\parallel} + I_{B\parallel},$$

$$I_2 = I_{B\perp}; \text{ and}$$

the superficially reflected light only has a parallel component and the multiple backscattered light has no polarized characteristics, therefore $$I_R = I_{R\parallel},$$

$$I_B = 2I_{B\perp}.$$

Then, the superficially reflected light and the multiple backscattered light can be calculated by the following two equations separately:

$$I_R = I_1 - I_2 \text{ and}$$

$$I_B = 2I_2.$$

The processing module may use the $I_R$ and $I_B$ as input signals, and remove motion artifacts by the adaptive noise removal algorithm. The functions, operations, and steps of the storage module and the output module thereafter are the same as those in Embodiment 1.

Embodiment 37

Figure 26C:
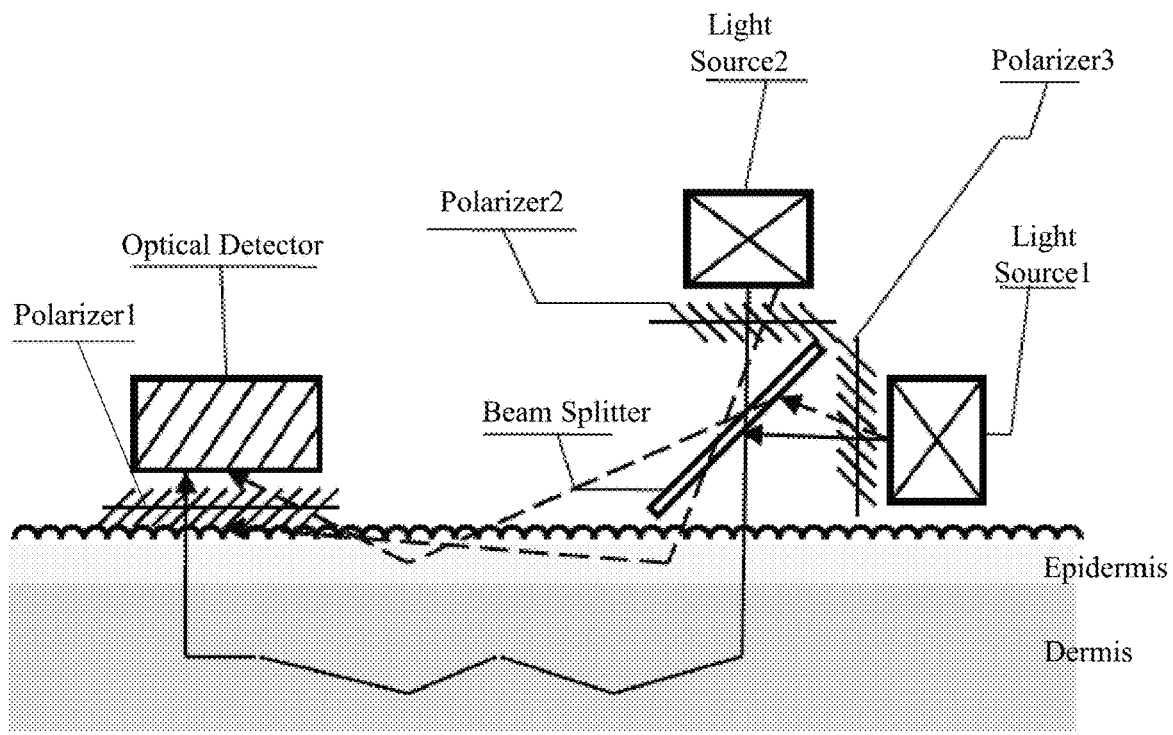

A vital signal detection device may include a detection module different from that described in Embodiment 1. The detection module may have a structure as shown in FIG. 26c, in which a sensor may include one optical detector, two light sources, three polarizers, and one beam splitter. Polarizers 2 and 3 are used to generate polarized light with a normal light source. If a laser is used as the reflection and transmission direction (such as a laser diode), the laser already has polarized characteristics, in which case the polarizers 2 and 3 may not be needed. The optical detector may be adjacent to the skin surface, the two light sources may be at a distance from the skin or may be adjacent to the skin surface, and the two light sources and the polarizers are located at reflection and transmission directions of the beam splitter respectively. Polarization directions of a polarizer 1 and the polarizer 3 are the same and are perpendicular to a polarization direction of the polarizer 2. The reflected and transmitted components caused by the beam splitter may be the same. When the sensor operates, a light source 1 and a light source 2 may emit light alternately, and the optical detector may detect reflected signals when the light source 1 and the light source 2 emit light, respectively obtaining a photoelectric signal 1 and a photoelectric signal 2. Since the polarization directions of the polarizer 1 and the polarizer 3 are the same, the photoelectric signal 1 detected by the photodetector when the light source 1 emits light may include a parallel component of less backscattered light and a parallel component of multiple backscattered light. Since the polarization direction of the polarizer 2 is perpendicular to the polarization direction of the polarizer 3, a photoelectric signal 2 detected by the photodetector when the light source 2 emits light may not include the less backscattered light, but only include a perpendicular component of the multiple backscattered light. When the brightness of light emitted by the light source 1 and light source 2 is the same, the multiple backscattered light generated when they emit light are equal since components reflected and transmitted by the beam splitter are equal. When the photoelectric signal 1 is represented as $I_1$, the photoelectric signal 2 is represented as $I_2$, the less backscattered light is represented as $I_{BR}$ the multiple backscattered light is represented as $I_B$, and subscripts $\parallel$ and $\perp$ represent a parallel component and a perpendicular component respectively, $$I_1 = I_{BR\parallel} + I_{B\parallel},$$

$I_2=I_{B\perp}$; and the less backscattered light only has a parallel component and the multiple backscattered light has no polarized characteristics, therefore $I_{BR}=I_{BR\parallel}$, $I_B=2I_{B\perp}$.

Then, the superficially reflected light and the multiple backscattered light can be calculated by the following two equations separately:

$I_{BR}=I_1-I_2$ and $I_B=2I_2$.

The processing module may use the $I_{BR}$ and $I_B$ as input signals, and remove motion artifacts by the adaptive noise removal algorithm. The functions, operations, and steps of the storage module and the output module thereafter are the same as those in Embodiment 1.

Embodiment 38

Figure 26D:
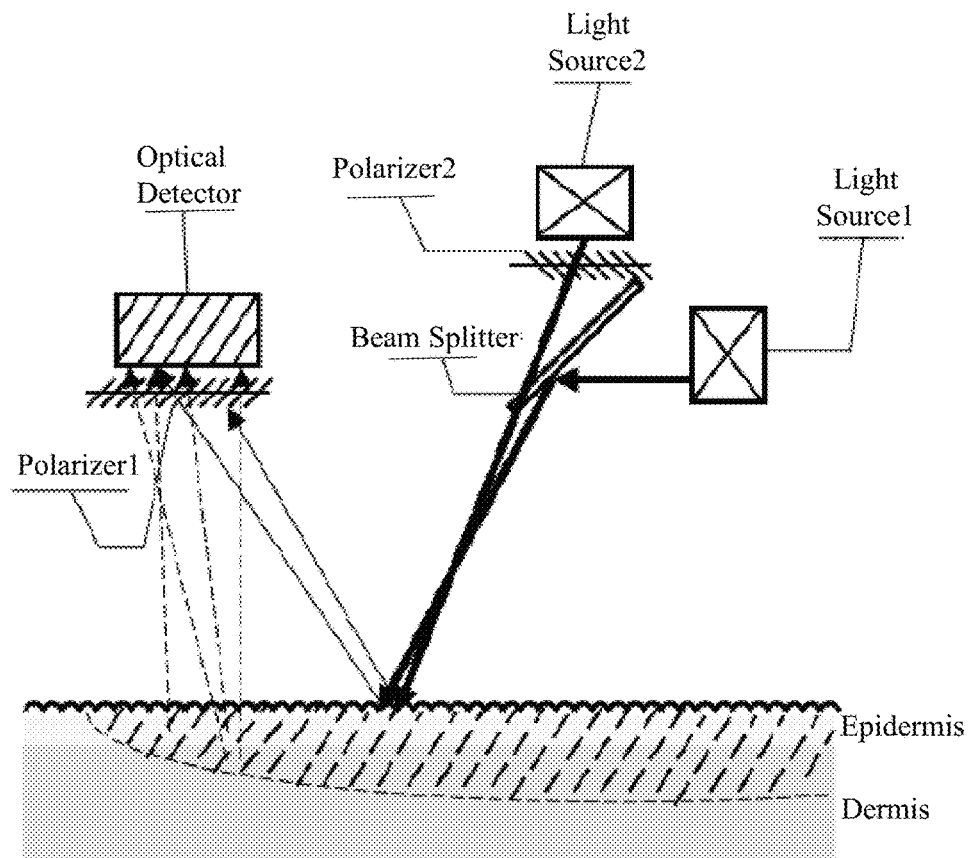

A vital signal detection device may include a detection module different from that described in Embodiment 1. The detection module may have a structure as shown in FIG. 26d, in which a sensor may include one optical detector, two light sources, two polarizers, and one beam splitter. A polarizer 2 is used to generate a polarized light with a normal light source. If a laser is used as the light source (such as a laser diode), the laser already has polarized characteristics, in which case the polarizer 2 may not be needed. The light sources and the optical detector are at a distance from the skin, a light source 1 is located at a reflection direction of the beam splitter, and a light source 2 and a polarizer 2 are located at a transmission direction of the beam splitter. A polarization direction of a polarizer 1 is perpendicular to a polarization direction of the polarizer 2. The reflected and transmitted components caused by the beam splitter may be the same. When the sensor operates, a light source 1 and a light source 2 may emit light alternately, and the optical detector may detect reflected signals when the light source 1 and the light source 2 emit light, respectively obtaining a photoelectric signal 1 and a photoelectric signal 2. Since there is no polarizer below the light source 1, the photoelectric signal 1 detected by the photodetector when the light source 1 emits light may include a parallel component of superficially reflected light and a parallel component of multiple backscattered light. Since the polarization direction of the polarizer 1 is perpendicular to the polarization direction of the polarizer 2, a photoelectric signal 2 detected by the photodetector when the light source 2 emits light may not include the superficially reflected light, but only include a perpendicular component of the multiple backscattered light. When the brightness of light emitted by the light source 1 is the same as the brightness of light emitted by light source 2 and passing through the polarizer 2, the multiple backscattered light generated when they emit light are equal since components reflected and transmitted by the beam splitter are equal. When the photoelectric signal 1 is represented as $I_1$, the photoelectric signal 2 is represented as $I_2$, the superficially reflected light is represented as $I_R$, the multiple backscattered light is represented as $I_B$, and subscripts $\parallel$ and $\perp$ represent a parallel component and a perpendicular component respectively, $I_1=I_{R\parallel}+I_{B\parallel}$ and $I_2=I_{B\perp}$.

The superficially reflected light is not polarized when the light source 1 emits light. The multiple backscattered light may not have polarized characteristics when the light source 1 and light source 2 emit light, therefore $I_R=2I_{R\parallel}$ and $I_B=2I_{B\perp}$.

Then, the superficially reflected light and the multiple backscattered light can be calculated by the following two equations separately:

$I_R=2(I_1-I_2)$ and $I_B=2I_2$.

The processing module may use the $I_R$ and $I_B$ as input signals, and remove motion artifacts by the adaptive noise removal algorithm. The functions, operations, and steps of the storage module and the output module thereafter are the same as those in Embodiment 1.

Embodiment 39

Figure 26E:
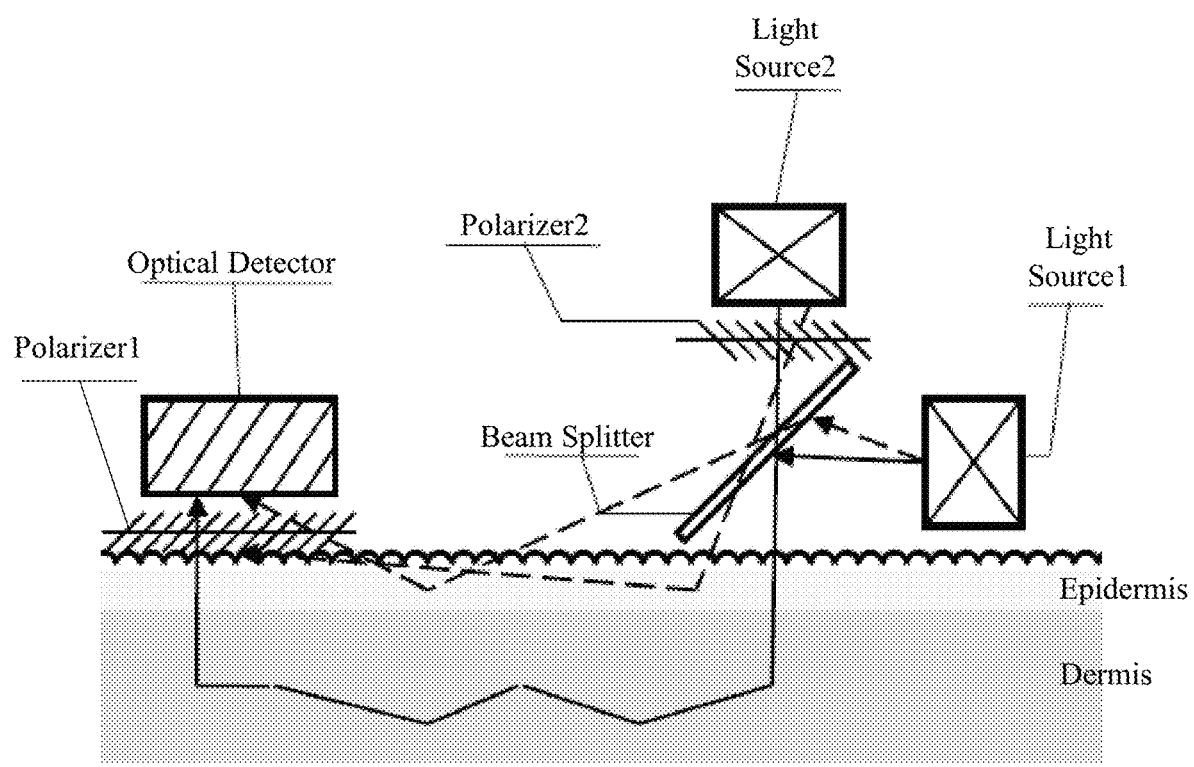

A vital signal detection device may include a detection module different from that described in Embodiment 1. The detection module may have a structure as shown in FIG. 26e, in which a sensor may include one optical detector, two light sources, two polarizers, and one beam splitter. A polarizer 2 is used to generate a polarized light with a normal light source. If a laser is used as the reflection and transmission direction (such as a laser diode), the laser already has polarized characteristics, in which case the polarizers 2 may not be needed. The optical detector may be adjacent to the skin surface, the two light sources may be at a distance from the skin or may be adjacent to the skin surface, and the two light sources and the polarizers are located at reflection and transmission directions of the beam splitter respectively. A polarization direction of a polarizer 1 is perpendicular to a polarization direction of the polarizer 2. The reflected and transmitted components caused by the beam splitter may be the same. When the sensor operates, a light source 1 and a light source 2 may emit light alternately, and the optical detector may detect reflected signals when the light source 1 and the light source 2 emit light, respectively obtaining a photoelectric signal 1 and a photoelectric signal 2. Since there is no polarizer below the light source 1, the photoelectric signal 1 detected by the photodetector when the light source 1 emits light may include a parallel component of less backscattered light and a parallel component of multiple backscattered light. Since the polarization direction of the polarizer 1 is perpendicular to the polarization direction of the polarizer 2, a photoelectric signal 2 detected by the photodetector when the light source 2 emits light may not include the less backscattered light, but only include a perpendicular component of the multiple backscattered light. When the brightness of light emitted by the light source 1 is the same as the brightness of light emitted by light source 2 and passing through the polarizer 2, the multiple backscattered light generated when they emit light are equal since components reflected and transmitted by the beam splitter are equal. When the photoelectric signal 1 is represented as $I_1$, the photoelectric signal 2 is represented as $I_2$, the less backscattered light is represented as $I_{BR}$, the multiple backscattered light is represented as $I_B$, and subscripts $\parallel$ and $\perp$ represent a parallel component and a perpendicular component respectively, $$I_1 = I_{BR\|} + I_{B\|} \text{ and}$$

$$I_2 = I_{B\perp}.$$

The less backscattered light is not polarized when the light source 1 emits light. The multiple backscattered light may not have polarized characteristics when the light source 1 and light source 2 emit light, therefore $$I_{BR} = 2I_{R\|} \text{ and}$$

$$I_B = 2I_{B\perp}.$$

Then, the less backscattered light and the multiple backscattered light can be calculated by the following two equations separately:

$$I_{BR} = 2(I_1 - I_2) \text{ and}$$

$$I_B = 2I_2.$$

The processing module may use the $I_{BR}$ and $I_B$ as input signals, and remove motion artifacts by the adaptive noise removal algorithm. The functions, operations, and steps of the storage module and the output module thereafter are the same as those in Embodiment 1.

Embodiment 40

Figure 27A:
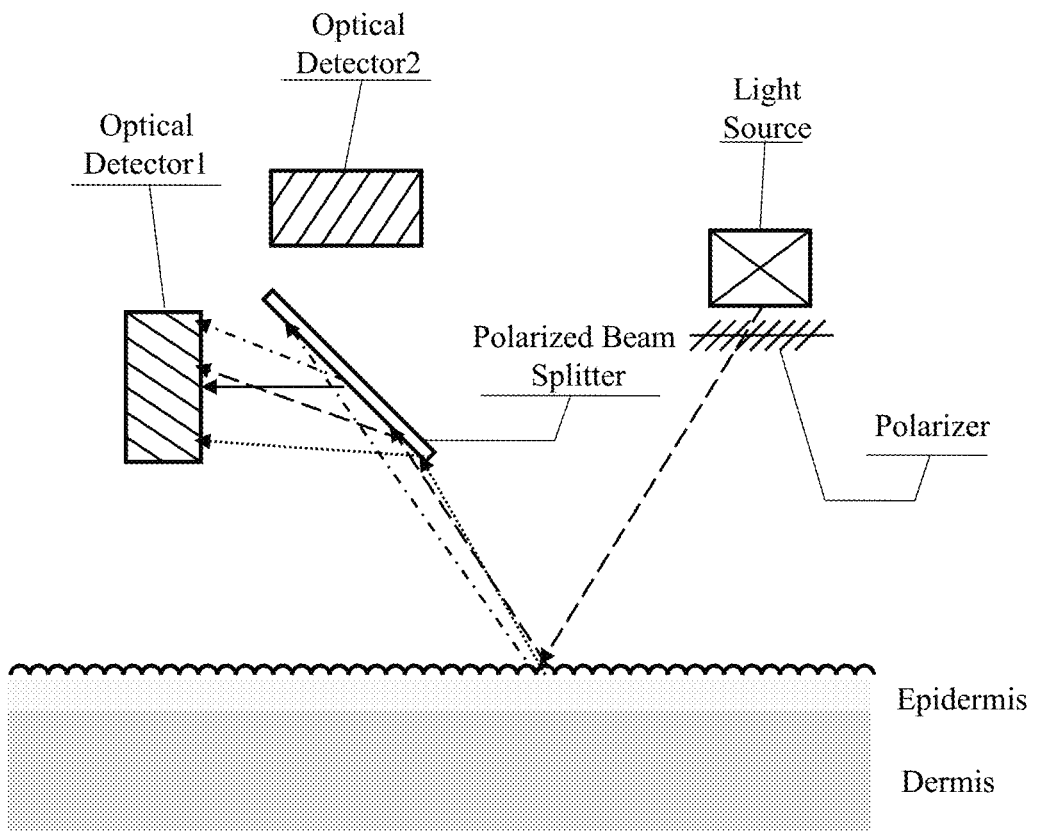

A vital signal detection device may include a detection module different from that described in Embodiment 1. The detection module may have a structure as shown in FIG. 27a, in which a sensor may include one light source, two optical detectors, one polarizer, and one polarized beam splitter. A polarizer 3 is used to generate a polarized light with a normal light source. If a laser is used as the light source (such as a laser diode), the laser already has polarized characteristics, in which case the polarizer 3 may not be needed. The light source and the optical detectors are at a distance from the skin, and the two optical detectors are located at reflection and transmission directions of the polarized beam splitter respectively. A reflected polarization direction of the polarized beam splitter is the same as that of the polarizer, a transmitted polarization direction of the polarized beam splitter is perpendicular to that of the polarizer, and the reflected and transmitted components are equal. When the sensor operates, an optical detector 1 and an optical detector 2 may detect reflected signals when the light source emits light, respectively obtaining a photoelectric signal 1 and a photoelectric signal 2. Since the reflected polarization direction of the polarized beam splitter is the same as that of the polarizer, the photoelectric signal 1 detected by the photodetector 1 may include a parallel component of superficially reflected light and a parallel component of multiple backscattered light. Since the transmitted polarization direction of the polarized beam splitter is opposite to that of the polarizer, the photoelectric signal 2 detected by the photodetector 2 may not include the superficially reflected light, but only include a perpendicular component of the multiple backscattered light. When the photoelectric signal 1 is represented as $I_1$, the photoelectric signal 2 is represented as $I_2$, the superficially reflected light is represented as $I_R$, the multiple backscattered light is represented as $I_B$, and subscripts $\|$ and $\perp$ represent a parallel component and a perpendicular component respectively, $$I_1 = I_{R\|} + I_{B\|},$$

$$I_2 = I_{B\perp}; \text{ and}$$

the superficially reflected light only has a parallel component and the multiple backscattered light has no polarized characteristics, therefore $$I_R = I_{R\|},$$

$$I_B = 2I_{B\perp}.$$

Then, the superficially reflected light and the multiple backscattered light can be calculated by the following two equations separately:

$$I_R = I_1 - I_2 \text{ and}$$

$$I_B = 2I_2.$$

The processing module may use the $I_R$ and $I_B$ as input signals, and remove motion artifacts by the adaptive noise removal algorithm. The functions, operations, and steps of the storage module and the output module thereafter are the same as those in Embodiment 1.

Embodiment 41

Figure 27B:
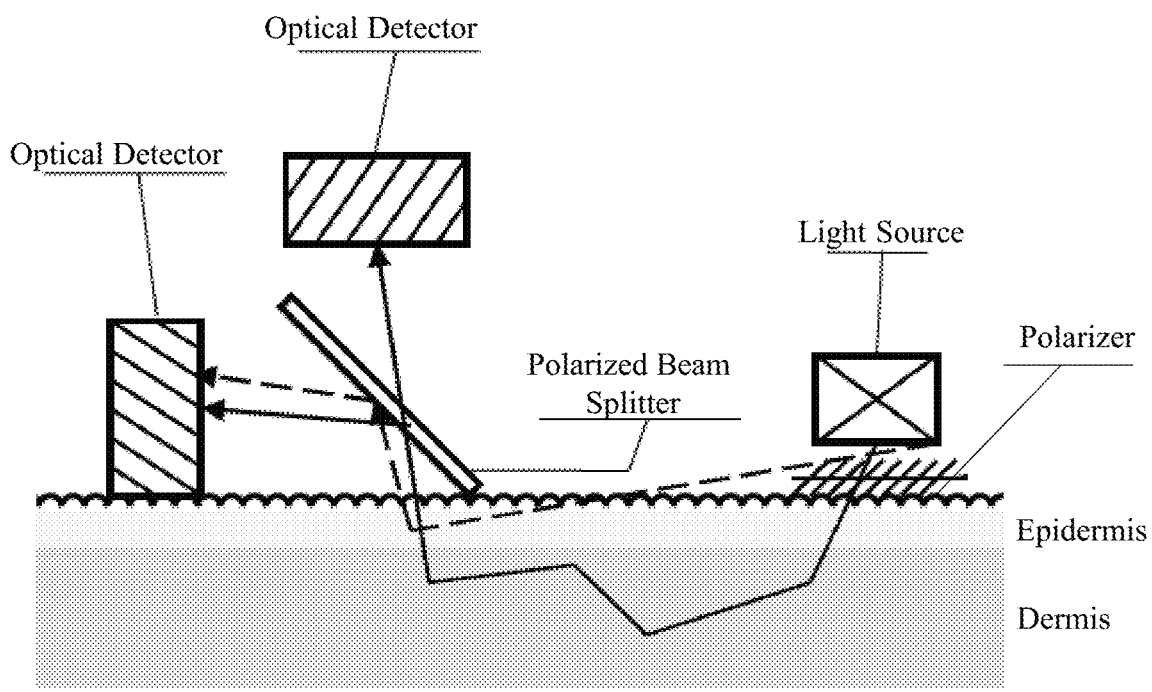

A vital signal detection device may include a detection module different from that described in Embodiment 1. The detection module may have a structure as shown in FIG. 27b, in which a sensor may include one light source, two optical detectors, one polarizer, and one polarized beam splitter. A polarizer 3 is used to generate a polarized light with a normal light source. If a laser is used as the reflection and transmission direction (such as a laser diode), the laser already has polarized characteristics, in which case the polarizers 3 may not be needed. The light source may be adjacent to the skin surface, the two optical detectors may be at a distance from the skin or may be adjacent to the skin surface, and the two optical detectors and the polarizers are located at reflection and transmission directions of the beam splitter respectively. A reflected polarization direction of the polarized beam splitter is the same as that of the polarizer, a transmitted polarization direction of the polarized beam splitter is perpendicular to that of the polarizer, and the reflected and transmitted components are equal. When the sensor operates, an optical detector 1 and an optical detector 2 may detect reflected signals when the light source emits light, respectively obtaining a photoelectric signal 1 and a photoelectric signal 2. Since the reflected polarization direction of the polarized beam splitter is the same as that of the polarizer, the photoelectric signal 1 detected by the photodetector 1 may include a parallel component of less backscattered light and a parallel component of multiple backscattered light. Since the transmitted polarization direction of the polarized beam splitter is opposite to that of the polarizer, the photoelectric signal 2 detected by the photodetector 2 may not include the less backscattered light, but only include a perpendicular component of the multiple backscattered light. When the photoelectric signal 1 is represented as $I_1$, the photoelectric signal 2 is represented as $I_2$, the less backscattered light is represented as $I_{BR}$ the multiple backscattered light is represented as $I_B$, and subscripts $\|$ and $\perp$ represent a parallel component and a perpendicular component respectively, $$I_1 = I_{BR\|} + I_{B\|},$$

$$I_2 = I_{B\perp}; \text{ and}$$

the less backscattered light only has a parallel component and the multiple backscattered light has no polarized characteristics, therefore $I_{BR}=I_{BR\|}$, $I_B=2I_{B\perp}$.

Then, the less backscattered light and the multiple backscattered light can be calculated by the following two equations separately:

$I_{BR}=I_1-I_2$ and $I_B=2I_2$.

The processing module may use the $I_{BR}$ and $I_B$ as input signals, and remove motion artifacts by the adaptive noise removal algorithm. The functions, operations, and steps of the storage module and the output module thereafter are the same as those in Embodiment 1.

Embodiment 42

Figure 27C:
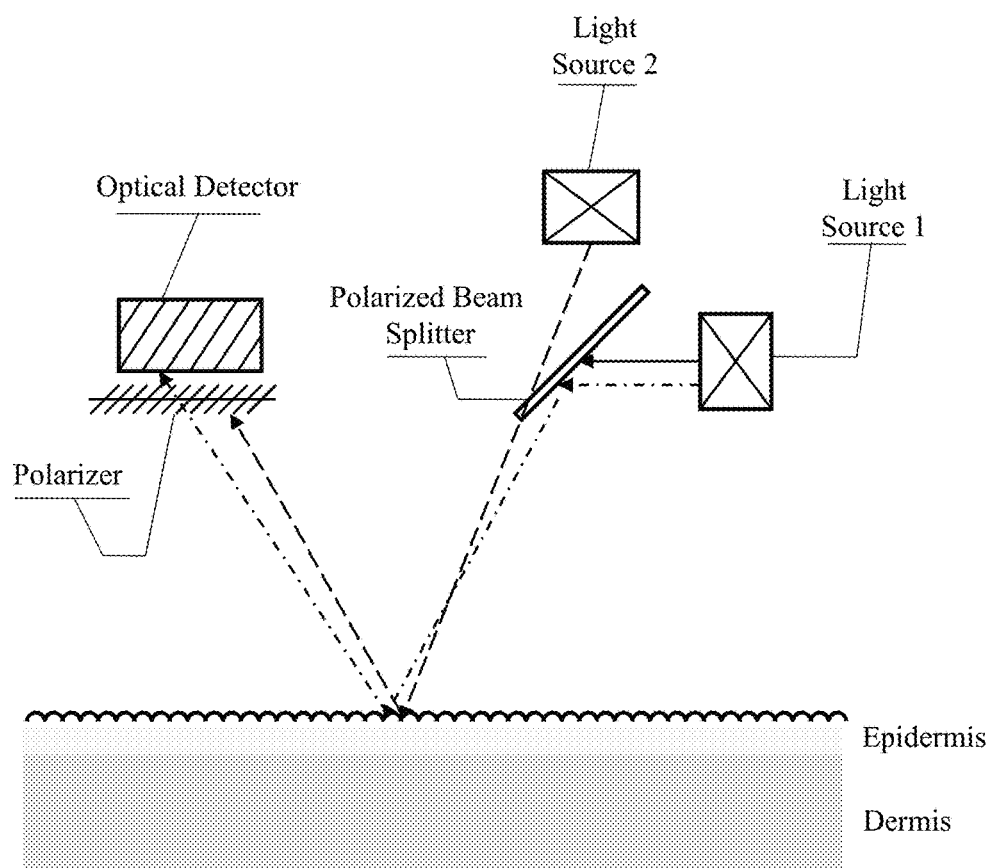

A vital signal detection device may include a detection module different from that described in Embodiment 1. The detection module may have a structure as shown in FIG. 27c, in which a sensor may include one optical detector, two light sources, one polarizer, and one polarized beam splitter. The light sources and the optical detector are at a distance from the skin, and the two light sources are located at reflection and transmission directions of the beam splitter respectively. A reflected polarization direction of the polarized beam splitter is the same as that of the polarizer, a transmitted polarization direction of the polarized beam splitter is perpendicular to that of the polarizer, and the reflected and transmitted components are equal. When the sensor operates, a light source 1 and a light source 2 may emit light alternately, and the optical detector may detect reflected signals when the light source 1 and the light source 2 emit light, respectively obtaining a photoelectric signal 1 and a photoelectric signal 2. Since the reflected polarization direction of the polarized beam splitter is the same as that of the polarizer, the photoelectric signal 1 detected by the photodetector when the light source 1 emits light may include a parallel component of superficially reflected light and a parallel component of multiple backscattered light. Since the transmitted polarization direction of the polarized beam splitter is perpendicular to that of the polarizer, the photoelectric signal 2 detected by the photodetector when the light source 2 emits light may not include the superficially reflected light, but only include a perpendicular component of the multiple backscattered light. When the brightness of light emitted by the light source 1 and light source 2 is the same, the multiple backscattered light generated when they emit light are equal since components reflected and transmitted by the polarized beam splitter are equal. When the photoelectric signal 1 is represented as $I_1$, the photoelectric signal 2 is represented as $I_2$, the superficially reflected light is represented as $I_R$, the multiple backscattered light is represented as $I_B$, and subscripts $\|$ and $\perp$ represent a parallel component and a perpendicular component respectively, $I_1=I_{R\|}+I_{B\|}$, $I_2=I_{B\perp}$; and the superficially reflected light only has a parallel component and the multiple backscattered light has no polarized characteristics, therefore $I_R=I_{R\|}$, $I_B=2I_{B\perp}$.

Then, the superficially reflected light and the multiple backscattered light can be calculated by the following two equations separately:

$I_R=I_1-I_2$ and $I_B=2I_2$.

The processing module may use the $I_R$ and $I_B$ as input signals, and remove motion artifacts by the adaptive noise removal algorithm. The functions, operations, and steps of the storage module and the output module thereafter are the same as those in Embodiment 1.

Embodiment 43

Figure 27D:
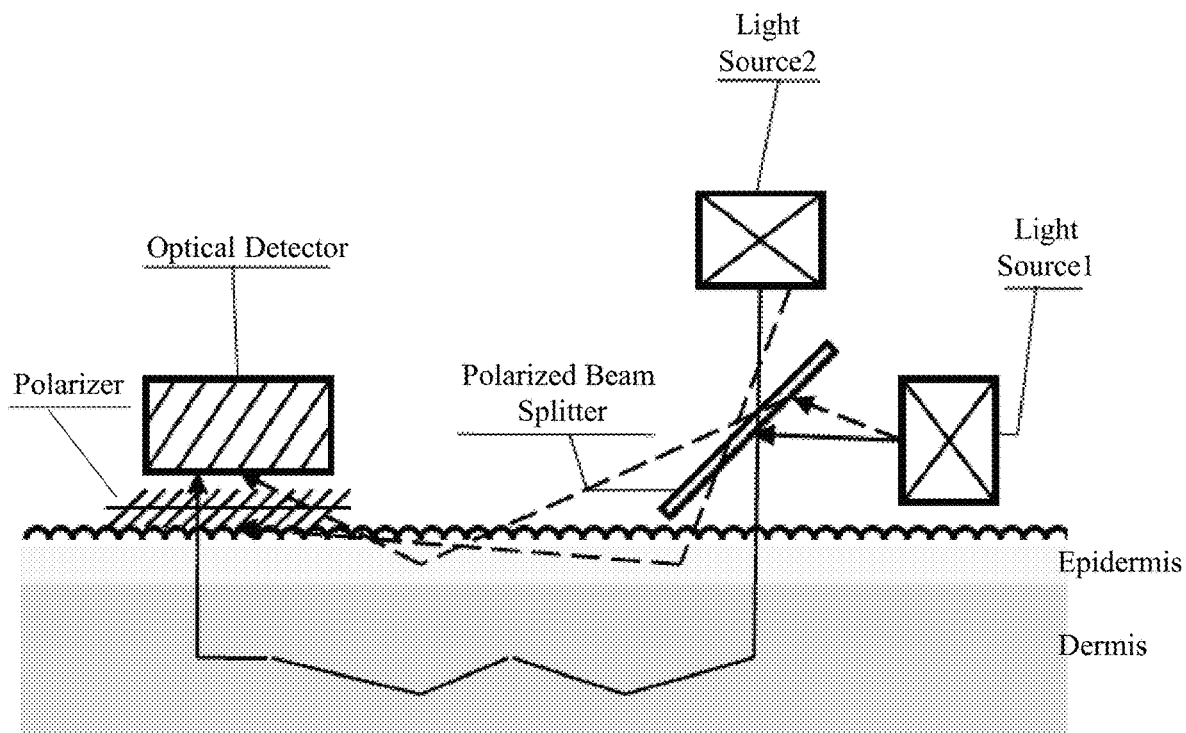

A vital signal detection device may include a detection module different from that described in Embodiment 1. The detection module may have a structure as shown in FIG. 27d, in which a sensor may include one optical detector, two light sources, one polarizer, and one polarized beam splitter. The optical detector may be adjacent to the skin surface, the two light sources may be at a distance from the skin or may be adjacent to the skin surface, and the two light sources and the polarizers are located at reflection and transmission directions of the polarized beam splitter respectively. A reflected polarization direction of the polarized beam splitter is the same as that of the polarizer, a transmitted polarization direction of the polarized beam splitter is perpendicular to that of the polarizer, and the reflected and transmitted components are equal. When the sensor operates, a light source 1 and a light source 2 may emit light alternately, and the optical detector may detect reflected signals when the light source 1 and the light source 2 emit light, respectively obtaining a photoelectric signal 1 and a photoelectric signal 2. Since the reflected polarization direction of the polarized beam splitter is the same as that of the polarizer, the photoelectric signal 1 detected by the photodetector when the light source 1 emits light may include a parallel component of less backscattered light and a parallel component of multiple backscattered light. Since the transmitted polarization direction of the polarized beam splitter is perpendicular to that of the polarizer, the photoelectric signal 2 detected by the photodetector when the light source 2 emits light may not include the less backscattered light, but only include a perpendicular component of the multiple backscattered light. When the brightness of light emitted by the light source 1 and light source 2 is the same, the multiple backscattered light generated when they emit light are equal since components reflected and transmitted by the polarized beam splitter are equal. When the photoelectric signal 1 is represented as $I_1$, the photoelectric signal 2 is represented as $I_2$, the less backscattered light is represented as $I_{BR}$, the multiple backscattered light is represented as $I_B$, and subscripts $\|$ and $\perp$ represent a parallel component and a perpendicular component respectively, $I_1=I_{BR\|}+I_{B\|}$, $I_2=I_{B\perp}$; and the less backscattered light only has a parallel component and the multiple backscattered light has no polarized characteristics, therefore $I_{BR}=I_{BR\|}$, $I_B=2I_{B\perp}$.

Then, the less backscattered light and the multiple backscattered light can be calculated by the following two equations separately:

$$I_{BR} = I_1 - I_2 \text{ and}$$

$$I_B = 2I_2.$$

The processing module may use the $I_{BR}$ and $I_B$ as input signals, and remove motion artifacts by the adaptive noise removal algorithm. The functions, operations, and steps of the storage module and the output module thereafter are the same as those in Embodiment 1.

We claim:

1. A device, comprising:
a first signal source located at a first place, wherein the first signal source is configured to emit a first light beam to a surface of a living body;
at least one beam splitter configured to split a reflected signal by the living body into two parts;
a first signal detecting device located at a second place, wherein the first signal detecting device is configured to detect a first signal which is a first part of the split two parts of the reflected signal, the first signal being associated with the first light beam;
a second signal detecting device located at a third place, wherein the second signal detecting device is configured to detect a second signal which is a second part of the split two parts of the reflected signal, the second signal being associated with the first light beam but different from the first signal, each of the first signal source, the first signal detecting device, and the second signal detecting device being at a distance above the surface of the living body, wherein
the first signal relates to the second place relative to the first place, the distance between the first place and the surface of the living body, and the distance between the second place and the surface of the living body,
the second signal relates to the third place relative to the first place, the distance between the first place and the surface of the living body, and the distance between the third place and the surface of the living body,
each of the first signal and the second signal includes a vital signal sign component and a motion component of the living body, a ratio of the vital sign component included in the first signal being larger than a ratio of the vital sign component included in the second signal, wherein the ratio of the vital sign component included in the first signal is a ratio of the vital sign component included in the first signal to a noise signal in the first signal, and the ratio of the vital sign component included in the second signal is a ratio of the vital sign component to a noise signal in the second signal; and
a processor configured to determine a vital signal of the living body by performing, based on the first signal and the second signal, correction with respect to the motion of the living body using an adaptive filter,
wherein the first light beam emitted by the first signal source to the surface of the living body is a polarized light.

2. The device of claim 1, wherein a distance between the first place and the second place is greater than a distance between the first place and the third place.

3. The device of claim 1, wherein a distance between the first place and the surface of the living body is less than a distance between the third place and the surface of the living body.

4. The device of claim 1, further comprising a second signal source located at a fourth place, wherein the second signal source is configured to emit a second light beam to the living body.

5. The device of claim 1, wherein the processor is configured to determine information of heart rate of the living body.

6. The device of claim 1, further comprising a first polarizer located between the first signal detecting device and the living body and a second polarizer located between the second signal detecting device and the living body, wherein a first polarization direction of the first polarizer is same as a polarization direction of the first light beam emitted by the first signal source to the surface of the living body, and a second polarization direction of the second polarizer is perpendicular to the polarization direction of the first light beam emitted by the first signal source to the surface of the living body.

7. A device, comprising:
a first signal source located at a first place, wherein the first signal source is configured to emit a first light beam to a surface of a living body;
a second signal source located at a second place, wherein the second signal source is configured to emit a second light beam to the surface of the living body;
a first signal detecting device located at a third place, wherein the first signal detecting device is configured to detect a first signal and a second signal reflected by the living body at different time points, wherein the first signal associates with the first light beam, the second signal associates with the second light beam, and the first signal is different from the second signal, each of the first signal source, the second signal source, and the first signal detecting device being at a distance above the surface of the living body, wherein
the first signal relates to the first place relative to the third place, the distance between the first place and the surface of the living body, and the distance between the third place and the surface of the living body,
the second signal relates to the second place relative to the third place, the distance between the second place and the surface of the living body, and the distance between the third place and the surface of the living body,
each of the first signal and the second signal includes a vital sign component and a motion component of the living body, a ratio of the vital sign component included in the first signal being larger than a ratio of the vital sign component included in the second signal, wherein the ratio of the vital sign component included in the first signal is a ratio of the vital sign component included in the first signal to a noise signal in the first signal, and the ratio of the vital sign component included in the second signal is a ratio of the vital sign component to a noise signal in the second signal;
at least one beam splitter configured to cause the first light beam and the second light beam to emit to a same region of the living body; and
a processor configured to determine a vital signal of the living body by performing, based on the first signal and the second signal, correction with respect to the motion of the living body using an adaptive filter, wherein the first light beam emitted by the first signal source to the surface of the living body is a polarized light.

8. The device of claim 7, wherein a distance between the first place and the third place is greater than a distance between the second place and the third place.

9. The device of claim 7, wherein a distance between the first place and the surface of the living body is less than a distance between the third place and the surface of the living body.

10. The device of claim 7, wherein a distance between the second place and the surface of the living body is greater than a distance between the third place and the surface of the living body.

11. The device of claim 7, wherein the processor is configured to obtain information of heart rate of the living body based on the first signal and the second signal.

12. The device of claim 7, further comprising a first polarizer located between the first signal detecting device and the living body, a second polarizer located between the second signal source and the living body, wherein a polarization direction of the first polarizer is perpendicular to a polarization direction of the first light beam emitted by the first signal source to the surface of the living body, and the polarization direction of the first polarizer is same as a polarization direction of the second light beam emitted by the second signal source to the surface of the living body.

13. A method, comprising:

emitting, from a signal source located at a first place, a first light beam to a surface of a living body, wherein at least one beam splitter configured to split a reflected signal by the living body into two parts;

detecting, using a first signal detecting device located at a second place, a first signal which is a first part of the split two parts of the reflected signal;

detecting, using a second signal detecting device located at a third place, a second signal which is a second part of the split two parts of the reflected signal, the first signal and the second signal associated with the first light beam, the second signal being different from the first signal, each of the signal source, the first signal detecting device, and the second signal detecting device being at a distance above the surface of the living body, wherein the first signal relates to the second place relative to the first place, the distance between the first place and the surface of the living body, and the distance between the second place and the surface of the living body, the second signal relates to the third place relative to the first place, the distance between the first place and the surface of the living body, and the distance between the third place and the surface of the living body, each of the first signal and the second signal includes a vital sign component and a motion component of the living body, a ratio of the vital sign component included in the first signal being larger than a ratio of the vital sign component included in the second signal, wherein the ratio of the vital sign component included in the first signal is a ratio of the vital sign component included in the first signal to a noise signal in the first signal, and the ratio of the vital sign component included in the second signal is a ratio of the vital sign component to a noise signal in the second signal; and determining a vital signal of the living body by performing, based on the first signal and the second signal, correction with respect to the motion of the living body using an adaptive filter, wherein the first light beam emitted by the first signal source to the surface of the living body is a polarized light.

14. The method of claim 13, wherein the second signal includes a superficially reflected signal of the living body.

15. The method of claim 13, wherein a transmission distance of the first signal in the living body is greater than a transmission distance of the second signal in the living body.

16. The method of claim 13, wherein an intensity of multiple backscattered light in the first signal is greater than an intensity of multiple backscattered light in the second signal.

17. The method of claim 13, further comprising:

obtaining information of heart rate of the living body based on the first signal and the second signal.

* * * * *